US011384365B2

(12) United States Patent
Koukuntla et al.

(10) Patent No.: US 11,384,365 B2
(45) Date of Patent: Jul. 12, 2022

(54) EHV WITH INACTIVATED UL18 AND/OR UL8

(71) Applicant: Boehringer Ingelheim Vetmedica GmbH, Ingelheim am Rhein (DE)

(72) Inventors: Ramesh Koukuntla, Ames, IA (US); Jana M. Larsen, Story City, IA (US); Robert Barry Mandell, Collins, IA (US); Luka N. Pelz, Ankeny, IA (US); Eric Martin Vaughn, Ames, IA (US)

( * ) Notice: Subject to any disclaimer, the term of this patent is extended or adjusted under 35 U.S.C. 154(b) by 0 days.

(21) Appl. No.: 16/358,519

(22) Filed: Mar. 19, 2019

(65) Prior Publication Data

US 2019/0284577 A1 Sep. 19, 2019

(30) Foreign Application Priority Data

Mar. 19, 2018 (EP) .................................... 18162630

(51) Int. Cl.

| | |
|---|---|
| ***C12N 15/86*** | (2006.01) |
| ***A61K 39/145*** | (2006.01) |
| ***A61K 48/00*** | (2006.01) |
| ***C12N 7/00*** | (2006.01) |
| ***A61P 31/00*** | (2006.01) |

(52) U.S. Cl.

CPC ............ *C12N 15/86* (2013.01); *A61K 39/145* (2013.01); *A61K 48/00* (2013.01); *A61P 31/00* (2018.01); *C12N 7/00* (2013.01); *C12N 2710/16021* (2013.01); *C12N 2710/16043* (2013.01); *C12N 2710/16052* (2013.01); *C12N 2710/16062* (2013.01); *C12N 2710/16734* (2013.01); *C12N 2710/16743* (2013.01); *C12N 2710/16762* (2013.01); *C12N 2760/16034* (2013.01); *C12N 2760/16071* (2013.01)

(58) Field of Classification Search

None

See application file for complete search history.

(56) References Cited

U.S. PATENT DOCUMENTS 7,141,243 B2 * 11/2006 Neubauer ............... A61P 31/22
424/229.1

FOREIGN PATENT DOCUMENTS

| | | |
|---|---|---|
| CN | 105535959 | 5/2016 |
| CN | 105641692 A1 | 6/2016 |
| WO | 9827216 A1 | 6/1998 |
| WO | 2004020644 A1 | 3/2004 |

OTHER PUBLICATIONS

Barnard et al. (Virology, 1997, p. 97-106).*
Barnard et al., Virology, 1997, vol. 237, pp. 97-106.
Zhang Yunfei et al., Virology, Nov. 21, 2013, vol. 449, pp. 25-34.
Hassan Mahmoud et al., Journal of Veterinary Medical Science, Jan. 1, 2013, vol. 75, No. 10, pp. 1317-1321.
Isabella Muylaert et al., Journal of Biological Chemistry, Sep. 28, 2012, vol. 287, No. 40, pp. 33142-33152.

* cited by examiner

*Primary Examiner* — Agnieszka Boesen
(74) *Attorney, Agent, or Firm* — Steffan Finnegan

(57) ABSTRACT

The present invention relates to the field of (vector) vaccines, and especially to novel EHV's having an inactivation of UL18 and/or UL8. The present invention further concerns related expression cassettes and vectors, which are suitable to express genes of interest, especially antigen encoding sequences. The viral vectors of the present invention are useful for producing an immunogenic composition or vaccine.

19 Claims, 18 Drawing Sheets

Specification includes a Sequence Listing.

pCEP-ORF 43(co)

Fig. 1: pCEP-ORF 43(co)

Fig.2: pCEP-ORF 54(co)

Fig.3: Cloning of mCMV-RFP-pA into EHV-1 ORF 43 site

Fig. 4: Cloning of RFP into EHV-1 ORF 43 site

Fig. 5: Modified RED recombination:

Fig. 6: Cloning of mCMV-RFP-pA into EHV-1 ORF 54 site

Fig. 7: ST cells infected with EHV-1/RacH virus

Fig. 8: rEHV-1-43-RFP virus on ST and ST-43-CO cells

Fig. 9: rEHV-1-43-mCMV-RFP virus on ST and ST-43-CO cells

Fig. 10: EHV-1-54-mCMV-RFP virus on ST and ST-54-CO cells

Fig. 13: Cloning of H3 expression cassette at ORF70 of EHV-1

Fig. 14: Expression of H3 gene in rEHV-1 RacH-SE70-455-H3 virus infected VERO cells rEHV-1 RacH-SE70-455-H3

Anti-H3 monoclonal antibody

Mean Lung Virus Titers of Animals

(TCID50/ml vs groups)

neg. ctrl. | chall. ctrl. | EHV 1x | EHV 2x | Inact 2x | neg. ctrl. | chall. ctrl. | EHV 1x | EHV 2x | Inact 2x 1 day after challenge | 3 days after challenge

Mean Lung Virus Titers of Groups

(TCID50/ml vs groups)

neg. ctrl. | chall. ctrl. | EHV 1x | EHV 2x | Inact 2x | neg. ctrl. | chall. ctrl. | EHV 1x | EHV 2x | Inact 2x 1 day after challenge | 3 days after challenge

SEQUENCE LISTING

```
<160> NUMBER OF SEQ ID NOS: 24

<210> SEQ ID NO 1
<211> LENGTH: 945
<212> TYPE: DNA
<213> ORGANISM: Equine herpesvirus 1

<400> SEQUENCE: 1

atggcgagtg ccgcctttga gattgacatc ctactgccca gtgacctatc tcccgctgac      60

ctgtcagctc ttcaaaaatg cgagggtaag cttgtgtttt tgaccgctct gcgtcgtcgc     120

gtgatgctct ccagcgtcac cctctcgtca tactatgtca acggcgcacc cccggacacg     180

ctatccctga tggcggcgtt tcgtaggcgt tttcccgcta taatacagcg cgtgctgccc     240

aacaaaatga tagccgccgc cctgggagtc gcaccgcttc ctcccggggc gttcatacag     300

aacacaggcc cgtttgacct gtgcaacggg gactctgtgt gcgcgctgcc tcccattttg     360

gacgtggagg acaagctgcg cctaggatct gtgggcgagg aaatactatt tccgctgacc     420

gttccactcg cgcaagcgcg cgaactcatc gcgcggctgg tagcgcgcgc ggtgcaggct     480

ctcaccccaa acgcccaggc ccagcgcgga gcggaggtga tgttttacaa cggacgaaag     540

tacaacgtga ccccggatct cagacaccga gacgccgtta acggcgtggc gcggtctctg     600

gtgctaaaca tgatttttgc catgaacgag ggatcgcttg tgctgctctc gctgatacca     660

aacctgctca ccctgggaac ccaggacgga tttgtgaacg ccataatcca gatgggaagc     720

gccacccgtg aggttggcca gctcgtccac cagcagcccg tgccccaacc gcaggacggc     780
```

gctcgccgct tttgtgtgta cgacgctctg atgtcatgga tcagcgttgc ctcgcgtctt 840
ggtgacgtgg tcggtgggaa acccttggtg cggatctgta cgttcgaggg ccaggctacg 900
atttcccgcg gcgagaaggc ccctgtcatt caaacgcttt tgtaa 945

<210> SEQ ID NO 2
<211> LENGTH: 2256
<212> TYPE: DNA
<213> ORGANISM: Equine herpesvirus 1

<400> SEQUENCE: 2
atggagggca gcgtcgaatg gtttaacgga catgtttgtg ctaccagtat ttactctcta 60
tggacagatc cgcaccaccc agggcatctt caggcgctcg tctacatgct gtgtcggcgc 120
ggtagcgact acaccgcaga gttttgtcac gttcccgtct cgggcgaact cttgaaacgc 180
ggagctcgcg acgcatctct ggtaacaccg gcgcgcgttg ccagcgccgc gcagaccgcg 240
gctgtgcctg ggtgctggcc cctggctccc ctgggaaacg ccatgttgtg gaaatccgtc 300
tacggtggca taacggcggc gcttaagcgc gccgtgggaa gctttgcttt ctatcaaccc 360
ctggtgttag gaattaacac gcaaactgga cttttagtta ccctccgacc cgccgcgtct 420
gcgggtgaag gcggtggcga ccacgtctct ccgcgggcgg cgatcgtaaa tgtgtcggtg 480
gaggtagact tggacccagc gggcattgaa gcgagcgcgg ctagctccac aggatcgtct 540
ctcgccaggg ccagactctg cacgcttcga gatggatatt ttctctcaaa gcgggacatt 600
gccctagaag ttgagatcgc tacaaaggag gtttcatttt acagaaagta tgactctgtg 660
caacagcctg ccaacaagcg tcgcggcgac atggcagatt tgttcgtcgt gcacgaacga 720 accctttgc tagggggatg taaacgaatg ggagttaagg ttctattgcc gcgaacgttt 780
gactgtttag ttgccagctc ccagtcagtg tcgggtttag ctgccatggc gctgtacaaa 840
cagtggcacg ctactctatt ctctgtagag ctaccagata ctgttgtgca aatttttgct 900
tacctagggc cagaattaaa cccgtgtgga gaggaagtcg actattgttg ctttgttgga 960
tttcccggac tcccgaccct caaggccagt tcgagcacca cggaggctgt gcgcgatgca 1020
atggccgcct atagactgtc cgacgggctg tggccggctc taggtatgag cgcgtttcac 1080
tttttggctc catgggaccc ggaagacagg tggcccggtg aatcggaggc aaaacgggta 1140
gagggggcgg tacacaggct tcagcttggt accgaggatg attgggggc tgggcgggta 1200 tcatgcattt tagagtcgga cgctgtaatg caggggccgt ggttcgcaaa gtttgacttt 1260
tcggcgtttt tccccacgct gtacctgttg ctgtttcccg ccaatgagcg cttggctgag 1320
gtggttagat tgagggcacg tggccaacac cccaccctta agctcgcctt ggtatccttt 1380 tttgggggc tgcagcacat caaccccgta gcctataggt ccatcatagc cctatccaac 1440
ggaatcagta agcggctgga gcacgaagtc aatcagaggg gttttgccat ctgtacatat 1500
gtcaaagatg gcttttgggg ggcagccgga aatctgccat cagactctgt atcctacgcc 1560
gacgcgctgg tttacgcaga ggagctaaga agcgccgctc agaaggcggc cctcggacac 1620
gtgtccgaga tggggtttc gctgccggag ggtgtccact tgaatttgcg gctggagggt 1680
ttgtttacag acgccatctc gtggtccacc cactgttact ggttgtacaa ccgcctcacc 1740
aagatggaag actttgtagg cttccccgcc aagagcgggg ccggcagagc cgcgaaggcg 1800
agcttgtctg ccttgctacc gctggtagcc gcggtatgcg actctagcga tatgagcacc 1860
ctccatcagt ctgtacgggg ggcctgcgaa cagctggtag ccggcgcttt tgccgagcgc 1920
aacaacccgc agttttggag taccaggacg ggatcgagt cgtctacgct actcccccg 1980

```
gcagtttaca ggaacggcag cttgctcgac agagactgtg ggcagaggga aattgtgttg   2040

actcgcaaac acgactgtga atccccatcg cccgtaccct ggacgctctt cccaccaccc   2100

ttggttttgg ggcgcattga ctgtatggtc tatcttacgt ccattttcaa aacttatcta   2160

agcatgttaa acagagcaat atctgcctcg tgcgacgcgg atgaatctat gaatgtggac   2220

tttccaatct ctgattatgc atttttattt acctaa                             2256


<210> SEQ ID NO 3
<211> LENGTH: 945
<212> TYPE: DNA
<213> ORGANISM: Equine herpesvirus 1

<400> SEQUENCE: 3

atggcatccg ccgccttcga gatagatata ctgctcccat ccgatctgtc accggctgac     60

cttagcgccc ttcaaaaatg tgaaggaaag ttggtctttc ttaccgcgtt gcgccgcagg    120

gtgatgctta gctccgttac gctgtcatct tattatgtga acggtgctcc tccagacact    180

ctcagtctga tggccgcatt tagacgacgg ttcccagcaa taatacaacg ggtgctcccg    240

aataaaatga tcgctgcggc tttgggcgtt gctccccttc cacctggagc gtttatacaa    300

aacaccggcc cattcgatct gtgcaacggc gactctgtgt gtgcgctccc gcccatactc    360

gacgttgaag acaaactgcg acttggctcc gttggagagg aaattctctt tccccttact    420

gtccccttgg cgcaagcccg agagcttata gcgcgattgg tcgcaagggc agtgcaggcg    480

ctgaccccga atgctcaagc tcagcgcggg gcagaagtga tgttttacaa cggaaggaaa    540

tacaatgtga ctcctgatct taggcaccga gatgcagtta atggggtcgc cagaagtctt    600

gttttgaata tgatcttcgc aatgaatgag gggagcttgg tcttgctcag cctgattcct    660

aatcttctga cacttggtac gcaggatggc tttgtcaatg caataattca aatgggatct    720

gctactaggg aagtcggaca gctcgtgcac cagcagcctg tgccccaacc acaagatggg    780

gcccgccgct tttgcgttta cgacgcactg atgagctgga tatcagtggc ttccagactg    840

ggtgatgtgg ttggtggtaa gccactcgtt cggatctgca ccttcgaggg gcaagctacg    900

atttcccgcg gcgaaaaggc tcctgtcata cagacacttc tctaa                    945


<210> SEQ ID NO 4
<211> LENGTH: 2256
<212> TYPE: DNA
<213> ORGANISM: Equine herpesvirus 1

<400> SEQUENCE: 4

atggaaggtt ccgtggaatg gtttaatgga cacgtctgcg ccactagcat ttactctttg     60

tggaccgatc cacaccaccc tggacacttg caggcgctgg tctacatgct gtgccgccgc    120

ggctccgact atactgctga attttgtcac gtccccgtca gtggtgaact tctgaaacgg    180

ggggcaagag atgccagctt ggttacgcct gcgcgcgttg ccagtgcggc ccaaaccgcc    240

gcagtccccg gatgctggcc tctggcacca ctcggcaacg ccatgctgtg gaagagtgtc    300

tatggaggta ttacagccgc tctcaagcgg gcagtgggct cattcgcatt ttaccaaccg    360

ttggtcctcg gcataaatac ccaaacggga ctccttgtta ctctccggcc ggctgcctca    420

gcgggcgagg gaggcggcga ccacgtttct cctagggctg cgatagtgaa cgtctccgtc    480

gaggtggacc tcgatccagc cgggatcgag gcgtccgcgg cgtcatctac cggaagctca    540

cttgcacgag cacggctttg taccttgcgc gatggctact ttctttccaa acgagatatt    600
```

```
gcgttggagg tcgagatcgc aacaaaagag gttagtttct atagaaaata tgattccgtt     660
cagcagccgg ccaataaacg gcgcggcgat atggctgatt tgtttgtggt ccatgagcga     720
acactgctcc tggggggctg taaacgaatg ggtgttaaag ttttgcttcc acggactttt     780
gactgcctcg tggcttctag tcaaagtgtc tcaggtcttg ccgcaatggc gttgtataaa     840
cagtggcacg cgacgctgtt ttcagtggag ttgccagata cagttgtgca aatctttgcg     900
tacttgggtc ctgagcttaa tccttgcgga gaggaagtgg actattgttg ttttgtcggc     960
tttccgggtt tgccgacact gaaggcttct tccagtacca cggaggctgt ccgagatgcc    1020
atggctgcat atcgacttag cgatggtctc tggcccgcac tcggcatgtc agcttttcat    1080
tttctcgccc cgtgggaccc ggaagaccgg tggccgggtg agtcagaggc caagagagtg    1140
gagggggcag ttcaccggct gcaattggga acagaggacg attggggtgc tggacgggtc    1200
tcatgtatat tggagtctga cgctgtcatg cagggaccat ggtttgcaaa attcgatttc    1260
tccgctttct ttccaacgtt gtacctgctt cttttccccg ccaacgaaag gcttgcagaa    1320
gttgttcggt tgcgggcgag gggacagcat ccgaccctga aactggcatt ggtgagcttc    1380
tttggcggct tgcagcatat taacccagtt gcgtacaggt caattattgc tctctccaat    1440
gggataagca agcggttgga gcacgaggtc aaccagagag ggtttgcaat ttgcacatac    1500
gtcaaggacg ggttttgggg agccgctgga aacctgccgt ccgatagcgt tagttatgca    1560
gacgccctcg tttacgctga ggagctgaga agcgcggcgc aaaaggctgc gttgggacac    1620
gtttccgaaa tgggcttctc tctccctgaa ggtgttcatc ttaatctcag gctggaaggg    1680
ttgttcaccg atgctattag ctggagcaca cactgctact ggttgtacaa ccgacttacc    1740
aaaatggaag actttgtggg cttccccgcg aaaagtggag ctgggagggc cgctaaggcc    1800
agcttgtctg cgttgttgcc gctcgtggca gccgtctgcg attcctcaga tatgtctacc    1860
ctccatcaaa gcgtcagagg agcctgcgag cagcttgttg ccggggcctt cgccgaaagg    1920
aacaatccgc aattttggtc cacgcggact ggtattgaat catccaccct gctccctccg    1980
gcggtgtacc ggaatggctc tctcttggac agggattgtg gccaaagaga gatcgtgctg    2040
acaaggaaac atgactgtga gagcccaagc cccgttccgt ggactctgtt tccgcccccg    2100
cttgttctcg gtcggatcga ttgtatggtt tatcttacaa gcattttcaa aacttatctt    2160
agcatgttga atcgagcaat aagcgcatct tgcgacgcgg acgagtctat gaatgtcgac    2220
tttcctatct cagactacgc ttttctcttc acttaa                              2256
```

<210> SEQ ID NO 5
<211> LENGTH: 171
<212> TYPE: DNA
<213> ORGANISM: Equine herpesvirus 1

<400> SEQUENCE: 5

```
tctgcttgag cgctagcgct ccgtctcgac ctcccagagt ggttattggt acggttggtg      60
ggtggttttg actgccttta atccctagca gactttaatc gatagaaggg gcataataag     120
gaagtttttt tggggggcg tcgctcgggt ttggggtgcc tccacgtaga g              171
```

<210> SEQ ID NO 6
<211> LENGTH: 265
<212> TYPE: DNA
<213> ORGANISM: Equine herpesvirus 1

<400> SEQUENCE: 6

```
cctcaccctc cccccaacgc ccattttaac ccccttatgc aaataaactt gacaccatgt      60
```

tatatattac atgtagtatg agtttttaat gatgtcggca aacaaaacta acacgtatcc 120
tcactgcgcg gggagactgg aaaacgcatc gctggttggc gggaggctgg acaaataaac 180
ggccatcacc agggccacca acatatcgtc cgacgcgccg ttgcgtttac cggtaaacac 240
tctagtttcg gaggttccgg taacc 265

<210> SEQ ID NO 7
<211> LENGTH: 3528
<212> TYPE: DNA
<213> ORGANISM: Artificial Sequence
<220> FEATURE:
<223> OTHER INFORMATION: mCMV promoter with RFP Gene

<400> SEQUENCE: 7
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acctcgcgaa 420
tgcatctaga tgacccaatt tcgctacctt aggaccgtta tagttaggta acctctgctt 480
gagcgctagc gctccgtctc gacctcccag agtggttatt ggtacggttg gtgggtggtt 540
ttgactgcct ttaatcccta gcagacttta atcgatagaa ggggcataat aaggaagttt 600
ttttgggggg gcgtcgctcg ggtttggggt gcctccacgt agagactagt tactgagtca 660
ttagggactt tccaatgggt tttgcccagt acataaggtc aataggggtg aatcaacagg 720
aaagtcccat tggagccaag tacactgagt caatagggac tttccattgg gttttgccca 780
gtacaaaagg tcaatagggg gtgagtcaat gggtttttcc cattattggc acgtacataa 840
ggtcaatagg ggtgagtcat tgggtttttc cagccaattt aattaaaacg ccatgtactt 900
tcccaccatt gacgtcaatg ggctattgaa actaatgcaa cgtgaccttt aaacggtact 960
ttcccatagc tgattaatgg gaaagtaccg ttctcgagcc aatacacgtc aatgggaagt 1020
gaaagggcag ccaaaacgta acaccgcccc ggttttcccc tggaaattcc atattggcac 1080
gcattctatt ggctgagctg cgttctacgt gggtataaga ggcgcgacca gcgtcggtac 1140
cgtcgcagtc ttcggtctga ccaccgtaga acgcagacgc gtggcccgaa tgcatctaga 1200
tggatccgcc gccaccatgg tgagcaaggg cgaggaggat aacatggcca tcatcaagga 1260
gttcatgcgc ttcaaggtgc acatggaggg ctccgtgaac ggccacgagt tcgagatcga 1320
gggcgagggc gagggccgcc cctacgaggg cacccagacc gccaagctga aggtgaccaa 1380
gggtggcccc ctgcccttcg cctgggacat cctgtcccct cagttcatgt acggctccaa 1440
ggcctacgtg aagcaccccg ccgacatccc cgactacttg aagctgtcct tccccgaggg 1500
cttcaagtgg gagcgcgtga tgaacttcga ggacggcggc gtggtgaccg tgacccagga 1560
ctcctccctg caggacggcg agttcatcta caaggtgaag ctgcgcggca ccaacttccc 1620
ctccgacggc cccgtaatgc agaagaagac catgggctgg gaggcctcct ccgagcggat 1680
gtaccccgag gacggcgccc tgaagggcga gatcaagcag aggctgaagc tgaaggacgg 1740
cggccactac gacgctgagg tcaagaccac ctacaaggcc aagaagcccg tgcagctgcc 1800

-continued

```
cggcgcctac aacgtcaaca tcaagttgga catcacctcc cacaacgagg actacaccat   1860

cgtggaacag tacgaacgcg ccgagggccg ccactccacc ggcggcatgg acgagctgta   1920

caagtaagtc gactatctag atgcattcga aacttaatta aggtaccctg tgccttctag   1980

ttgccagcca tctgttgttt gcccctcccc cgtgccttcc ttgaccctgg aaggtgccac   2040

tcccactgtc ctttcctaat aaaatgagga aattgcatcg cattgtctga gtaggtgtca   2100

ttctattctg gggggtgggg tggggcagga cagcaagggg gaggattggg aagacaatag   2160

caggcatgct ggggatgcgg tgggctctat ggatcctagg gataacaggg taatcgattt   2220

attcaacaaa gccacgttgt gtctcaaaat ctctgatgtt acattgcaca agataaaaat   2280

atatcatcat gaacaataaa actgtctgct tacataaaca gtaatacaag gggtgttatg   2340

agccatattc aacgggaaac gtcttgctcg aggccgcgat taaattccaa catggatgct   2400

gatttatatg ggtataaatg ggctcgcgat aatgtcgggc aatcaggtgc gacaatctat   2460

cgattgtatg ggaagcccga tgcgccagag ttgtttctga aacatggcaa aggtagcgtt   2520

gccaatgatg ttacagatga gatggtcaga ctaaactggc tgacggaatt tatgcctctt   2580

ccgaccatca agcattttat ccgtactcct gatgatgcat ggttactcac cactgcgatc   2640

cccgggaaaa cagcattcca ggtattagaa gaatatcctg attcaggtga aaatattgtt   2700

gatgcgctgg cagtgttcct gcgccggttg cattcgattc ctgtttgtaa ttgtcctttt   2760

aacagcgatc gcgtatttcg tctcgctcag gcgcaatcac gaatgaataa cggtttggtt   2820

gatgcgagtg attttgatga cgagcgtaat ggctggcctg ttgaacaagt ctggaaagaa   2880

atgcataagc ttttgccatt ctcaccggat tcagtcgtca ctcatggtga tttctcactt   2940

gataacctta tttttgacga ggggaaatta ataggttgta ttgatgttgg acgagtcgga   3000

atcgcagacc gataccagga tcttgccatc ctatggaact gcctcggtga gttttctcct   3060

tcattacaga aacggctttt tcaaaaatat ggtattgata atcctgatat gaataaattg   3120

cagtttcatt tgatgctcga tgagtttttc taaccatggc tgtgccttct agttgccagc   3180

catctgttgt ttgcccctcc cccgtgcctt ccttgaccct ggaaggtgcc actcccactg   3240

tcctttccta ataaaatgag gaaattgcat cgcattgtct gagtaggtgt cattctattc   3300

tggggggtgg ggtggggcag gacagcaagg gggaggattg ggaagacaat agcaggcatg   3360

ctggggatgc ggtgggctct atggatccga ccctccccaa acgcatgccc tcaccctccc   3420

cccaacgccc attttaaccc ccttatgcaa ataaacttga caccatgtta tatattacat   3480

gtagtatgag tttttaatga tgtcggcaaa caaaactaac acgtatcc                3528
```

<210> SEQ ID NO 8
<211> LENGTH: 1505
<212> TYPE: DNA
<213> ORGANISM: Artificial Sequence
<220> FEATURE:
<223> OTHER INFORMATION: Kanamycin gene flanked by SEQ ID NO 5 and 6

<400> SEQUENCE: 8

```
tctgcttgag cgctagcgct ccgtctcgac ctcccagagt ggttattggt acggttggtg     60

ggtggttttg actgccttta atccctagca gactttaatc gatagaaggg gcataataag    120

gaagtttttt tggggggggcg tcgctcgggt ttggggtgcc tccacgtaga gactagggat    180

aacagggtaa tcgatttatt caacaaagcc acgttgtgtc tcaaaatctc tgatgttaca    240

ttgcacaaga taaaaatata tcatcatgaa caataaaact gtctgcttac ataaacagta    300

atacaagggg tgttatgagc catattcaac gggaaacgtc ttgctcgagg ccgcgattaa    360
```

attccaacat ggatgctgat ttatatgggt ataaatgggc tcgcgataat gtcgggcaat 420
caggtgcgac aatctatcga ttgtatggga agcccgatgc gccagagttg tttctgaaac 480
atggcaaagg tagcgttgcc aatgatgtta cagatgagat ggtcagacta aactggctga 540
cggaatttat gcctcttccg accatcaagc attttatccg tactcctgat gatgcatggt 600
tactcaccac tgcgatcccc gggaaaacag cattccaggt attagaagaa tatcctgatt 660
caggtgaaaa tattgttgat gcgctggcag tgttcctgcg ccggttgcat tcgattcctg 720
tttgtaattg tccttttaac agcgatcgcg tatttcgtct cgctcaggcg caatcacgaa 780
tgaataacgg tttggttgat gcgagtgatt ttgatgacga gcgtaatggc tggcctgttg 840
aacaagtctg gaaagaaatg cataagcttt tgccattctc accggattca gtcgtcactc 900
atggtgattt ctcacttgat aaccttattt ttgacgaggg gaaattaata ggttgtattg 960
atgttggacg agtcggaatc gcagaccgat accaggatct tgccatccta tggaactgcc 1020
tcggtgagtt ttctccttca ttacagaaac ggctttttca aaaatatggt attgataatc 1080
ctgatatgaa taaattgcag tttcatttga tgctcgatga gtttttctaa ccatggctgt 1140
gccttctagt tgccagccat ctgttgtttg cccctccccc gtgccttcct tgaccctgga 1200
aggtgccact cccactgtcc tttcctaata aaatgaggaa attgcatcgc attgtctgag 1260
taggtgtcat tctattctgg ggggtggggt ggggcaggac agcaaggggg aggattggga 1320
agacaatagc aggcatgctg gggatgcggt gggctctatg gatccgaccc tccccaaacg 1380
catgccctca ccctcccccc aacgcccatt ttaacccccct tatgcaaata aacttgacac 1440
catgttatat attacatgta gtatgagttt ttaatgatgt cggcaaacaa aactaacacg 1500
tatcc 1505

<210> SEQ ID NO 9
<211> LENGTH: 161
<212> TYPE: DNA
<213> ORGANISM: Equine herpesvirus 1

<400> SEQUENCE: 9
cgctagcgct ccgtctcgac ctcccagagt ggttattggt acggttggtg ggtggttttg 60
actgccttta atccctagca gactttaatc gatagaaggg gcataataag gaagtttttt 120 tggggggcg tcgctcgggt ttggggtgcc tccacgtaga g 161

<210> SEQ ID NO 10
<211> LENGTH: 120
<212> TYPE: DNA
<213> ORGANISM: Equine herpesvirus 1

<400> SEQUENCE: 10
cctcaccctc cccccaacgc ccattttaac ccccttatgc aaataaactt gacaccatgt 60
tatatattac atgtagtatg agtttttaat gatgtcggca aacaaaacta acacgtatcc 120

<210> SEQ ID NO 11
<211> LENGTH: 200
<212> TYPE: DNA
<213> ORGANISM: Equine herpesvirus 1

<400> SEQUENCE: 11
gcaacaggaa gctgtttgcg ggacccagat ataagctgag ggcgccaaag tggagcagaa 60
acctctgttt tctagaattg gacaatactg gcacctgcaa gactccgctt gatgccgcgc 120

-continued tggcagacct agcccctagc gcgtggccac aggtttacgg agcggttgac ttcgacgcac 180
tgtaacatca accaacccac 200

<210> SEQ ID NO 12
<211> LENGTH: 200
<212> TYPE: DNA
<213> ORGANISM: Equine herpesvirus 1

<400> SEQUENCE: 12
aaataaagac cataaacgtt atttttttc agtttatttt tgttgtttgg ggtacacacg 60
gtatgggcat cataaaaccc ctccatctca ccagctagtc gtataaaaca tatattgatt 120
ccggcacagg cttttcgtcc gtagcggtcc accagctata gagagtatca gccactactt 180
tagtacatag cggcgcattg 200

<210> SEQ ID NO 13
<211> LENGTH: 3138
<212> TYPE: DNA
<213> ORGANISM: Artificial Sequence
<220> FEATURE:
<223> OTHER INFORMATION: mCMV promoter driven RFP gene

<400> SEQUENCE: 13
gcaacaggaa gctgtttgcg ggacccagat ataagctgag ggcgccaaag tggagcagaa 60
acctctgttt tctagaattg gacaatactg gcacctgcaa gactccgctt gatgccgcgc 120
tggcagacct agcccctagc gcgtggccac aggtttacgg agcggttgac ttcgacgcac 180
tgtaacatca accaacccac gctagttact gagtcattag ggactttcca atgggttttg 240
cccagtacat aaggtcaata ggggtgaatc aacaggaaag tcccattgga gccaagtaca 300
ctgagtcaat agggactttc cattgggttt tgcccagtac aaaaggtcaa taggggggtga 360 gtcaatgggt ttttcccatt attggcacgt acataaggtc aataggggtg agtcattggg 420
tttttccagc caatttaatt aaaacgccat gtactttccc accattgacg tcaatgggct 480
attgaaacta atgcaacgtg acctttaaac ggtactttcc catagctgat taatgggaaa 540
gtaccgttct cgagccaata cacgtcaatg ggaagtgaaa gggcagccaa aacgtaacac 600
cgccccggtt ttcccctgga aattccatat tggcacgcat tctattggct gagctgcgtt 660
ctacgtgggt ataagaggcg cgaccagcgt cggtaccgtc gcagtcttcg gtctgaccac 720
cgtagaacgc agacgcgtgg cccgaatgca tctagatgga tccgccgcca ccatggtgag 780
caagggcgag gaggataaca tggccatcat caaggagttc atgcgcttca aggtgcacat 840
ggagggctcc gtgaacggcc acgagttcga gatcgagggc gagggcgagg gccgccccta 900
cgagggcacc cagaccgcca agctgaaggt gaccaagggt ggccccctgc ccttcgcctg 960
ggacatcctg tcccctcagt tcatgtacgg ctccaaggcc tacgtgaagc accccgccga 1020
catccccgac tacttgaagc tgtccttccc cgagggcttc aagtgggagc gcgtgatgaa 1080
cttcgaggac ggcggcgtgg tgaccgtgac ccaggactcc tccctgcagg acggcgagtt 1140
catctacaag gtgaagctgc gcggcaccaa cttcccctcc gacggccccg taatgcagaa 1200
gaagaccatg ggctgggagg cctcctccga gcggatgtac cccgaggacg gcgccctgaa 1260
gggcgagatc aagcagaggc tgaagctgaa ggacggcggc cactacgacg ctgaggtcaa 1320
gaccacctac aaggccaaga agcccgtgca gctgcccggc gcctacaacg tcaacatcaa 1380
gttggacatc acctcccaca acgaggacta caccatcgtg gaacagtacg aacgcgccga 1440
gggccgccac tccaccggcg gcatggacga gctgtacaag taagtcgact atctagatgc 1500
attcgaaact taattaaggt accctgtgcc ttctagttgc cagccatctg ttgtttgccc 1560
ctcccccgtg ccttccttga ccctggaagg tgccactccc actgtccttt cctaataaaa 1620
tgaggaaatt gcatcgcatt gtctgagtag gtgtcattct attctggggg gtggggtggg 1680
gcaggacagc aagggggagg attgggaaga caatagcagg catgctgggg atgcggtggg 1740
ctctatggat cctagggata acagggtaat cgatttattc aacaaagcca cgttgtgtct 1800
caaaatctct gatgttacat tgcacaagat aaaaatatat catcatgaac aataaaactg 1860
tctgcttaca taaacagtaa tacaaggggt gttatgagcc atattcaacg ggaaacgtct 1920
tgctcgaggc cgcgattaaa ttccaacatg gatgctgatt tatatgggta taaatgggct 1980
cgcgataatg tcgggcaatc aggtgcgaca atctatcgat tgtatgggaa gcccgatgcg 2040
ccagagttgt ttctgaaaca tggcaaaggt agcgttgcca atgatgttac agatgagatg 2100
gtcagactaa actggctgac ggaatttatg cctcttccga ccatcaagca ttttatccgt 2160
actcctgatg atgcatggtt actcaccact gcgatccccg ggaaaacagc attccaggta 2220
ttagaagaat atcctgattc aggtgaaaat attgttgatg cgctggcagt gttcctgcgc 2280
cggttgcatt cgattcctgt ttgtaattgt ccttttaaca gcgatcgcgt atttcgtctc 2340
gctcaggcgc aatcacgaat gaataacggt ttggttgatg cgagtgattt tgatgacgag 2400
cgtaatggct ggcctgttga acaagtctgg aaagaaatgc ataagctttt gccattctca 2460
ccggattcag tcgtcactca tggtgatttc tcacttgata accttatttt tgacgagggg 2520
aaattaatag gttgtattga tgttggacga gtcggaatcg cagaccgata ccaggatctt 2580
gccatcctat ggaactgcct cggtgagttt tctccttcat tacagaaacg gctttttcaa 2640
aaatatggta ttgataatcc tgatatgaat aaattgcagt ttcatttgat gctcgatgag 2700
tttttctaac catggctgtg ccttctagtt gccagccatc tgttgtttgc ccctcccccg 2760
tgccttcctt gaccctggaa ggtgccactc ccactgtcct ttcctaataa aatgaggaaa 2820
ttgcatcgca ttgtctgagt aggtgtcatt ctattctggg gggtggggtg gggcaggaca 2880
gcaaggggga ggattgggaa gacaatagca ggcatgctgg ggatgcggtg ggctctataa 2940
ataaagacca taaacgttat ttttttttcag tttatttttg ttgtttgggg tacacacggt 3000
atgggcatca taaaacccct ccatctcacc agctagtcgt ataaaacata tattgattcc 3060
ggcacaggct tttcgtccgt agcggtccac cagctataga gagtatcagc cactacttta 3120
gtacatagcg gcgcattg 3138

<210> SEQ ID NO 14
<211> LENGTH: 1695
<212> TYPE: DNA
<213> ORGANISM: swine influenza virus

<400> SEQUENCE: 14
atgaagacca ccatcatcct gatcctgctg acccactggg cctactccca gaaccccatc 60
agcggcaaca acaccgccac cctgtgcctc ggccaccacg ctgtggccaa tggcaccctg 120
gtcaagacca tctccgacga ccagattgaa gtcacaaatg ctacagaact ggtgcagagc 180
atctccatgg gcaagatttg taataattcc tatcgcatcc tggacggaag gaactgcacc 240
ctgatcgacg ccatgctcgg cgacccccat tgtgacgcct tccagtatga aaattgggac 300
ctgttcatcg agaggagctc cgccttctcc aattgttatc cctacgacat ccccgactac 360
gccagcctca gatccattgt cgcctccagc ggcaccctgg agttcaccgc ggaaggcttc 420
acctggacag gcgtcaccca gaacggccgc tccggagctt gtaaaagagg cagcgccgat 480
tccttcttca gccgcctgaa ctggctcaca aagagcggca gctcttatcc caccctgaac 540
gtgacaatgc ccaacaacaa gaacttcgac aaactctaca tctggggcat ccaccatcct 600
tccagcaatc aggaacagac aaaactctat attcaggaaa gcggcagggt gaccgtgtcc 660
accaagagaa gccaacagac aattattcct aacatcggca gcaggccctg ggtgagaggc 720
cagagcggac ggatttccat ctactggaca attgtcaaac ctggcgacat cctgatgatt 780
aacagcaatg gcaacctggt ggctccaaga ggatacttca agctgaagac aggcaagtcc 840
tccgtgatgc ggtccgacgt gcccatcgac atctgcgtga gcgaatgtat tacacctaat 900
ggcagcatct ccaacgacaa gccctttcag aacgtgaaca aggtcaccta cggcaagtgt 960
cctaaatata ttagacagaa taccctgaag ctcgctacag gcatgaggaa cgtgcccgaa 1020
aaacagatta ggggaatttt tggagctatt gctggcttca tcgaaaatgg atgggaagga 1080
atggtggacg gatggtatgg cttcagatat cagaatagcg aaggaaccgg acaggctgct 1140
gacctgaaga gcacccaagc cgccatcgac cagatcaacg gcaagctgaa ccgcgtgatc 1200
gaacggacaa atgaaaaatt tcatcagatt gaaaaagagt tctccgaagt cgaaggccgc 1260
atccaggacc tggagaaata tgtcgaggac accaagatcg acctgtggtc ctataatgct 1320
gaactcctcg tggccctgga gaatcagcat acaatcgacc tgaccgacgc tgaaatgaac 1380
aagctctttg agaagacccg ccggcagctc agagaaaatg ccgaagatat gggcggaggc 1440
tgcttcaaga tctaccacaa gtgcgacaac gcctgcattg gctccatccg gaatggaacc 1500
tacgaccatt atatctaccg cgacgaggcc ctgaacaacc ggtttcagat caagggagtc 1560
gagctgaagt ccggatataa agattggatt ctgtggattt ccttcgccat ttcctgcttc 1620
ctgatctgcg tggtgctgtt aggcttcatc atgtgggcct gccagaaggg caacatccgc 1680
tgcaacatct gcatc 1695

<210> SEQ ID NO 15
<211> LENGTH: 5191
<212> TYPE: DNA
<213> ORGANISM: Artificial Sequence
<220> FEATURE:
<223> OTHER INFORMATION: Nucleotide sequence of transfer vector pU70-
p455-71K71

<400> SEQUENCE: 15
caataaacgc ggtatgtcta ccttcaagcc tatgatgaac ggatgtttgg tgtttgcggc 60
tattataacg ctcttgagtt ttatgctatc tctgggaaca tgcgaaaatt acaggcgtgt 120
ggttcgggat cctagggata acagggtaat cgatttattc aacaaagcca cgttgtgtct 180
caaaatctct gatgttacat tgcacaagat aaaaatatat catcatgaac aataaaactg 240
tctgcttaca taaacagtaa tacaaggggt gttatgagcc atattcaacg ggaaacgtct 300
tgctcgaggc cgcgattaaa ttccaacatg gatgctgatt tatatgggta taaatgggct 360
cgcgataatg tcgggcaatc aggtgcgaca atctatcgat tgtatgggaa gcccgatgcg 420
ccagagttgt ttctgaaaca tggcaaaggt agcgttgcca atgatgttac agatgagatg 480
gtcagactaa actggctgac ggaatttatg cctcttccga ccatcaagca ttttatccgt 540
actcctgatg atgcatggtt actcaccact gcgatccccg ggaaaacagc attccaggta 600
ttagaagaat atcctgattc aggtgaaaat attgttgatg cgctggcagt gttcctgcgc 660
cggttgcatt cgattcctgt ttgtaattgt ccttttaaca gcgatcgcgt atttcgtctc 720

-continued

```
gctcaggcgc aatcacgaat gaataacggt ttggttgatg cgagtgattt tgatgacgag    780
cgtaatggct ggcctgttga acaagtctgg aaagaaatgc ataagctttt gccattctca    840
ccggattcag tcgtcactca tggtgatttc tcacttgata accttatttt tgacgagggg    900
aaattaatag gttgtattga tgttggacga gtcggaatcg cagaccgata ccaggatctt    960
gccatcctat ggaactgcct cggtgagttt tctccttcat tacagaaacg gctttttcaa   1020
aaatatggta ttgataatcc tgatatgaat aaattgcagt ttcatttgat gctcgatgag   1080
tttttctaaa ataaacgcgg tatgtctacc ttcaagccta tgatgaacgg atgtttggtg   1140
tttgcggcta ttataacgct cttgagtttt atgctatctc tgggaacatg cgaaaattac   1200
aggcgtgtgg ttcgggatcc gaccctgttg gtgggtgcgg ttggactcag aatcttggcg   1260
caggcatgga agtttgtcgg tgacgaaaca tacgacacca tccgcgcaga agcaaagaat   1320
ttagagaccc acgtaccctc aagtgctgca gagtcgtctc tagaaaacca atcgacacag   1380
gaggagtcta acagccccga agttgcccac ctgcgaagcg tcaacagcga tgacagtaca   1440
cacacggggg gtgcgtcgaa cggcatccag gactgtgaca gtcagctcaa aactgtgtat   1500
gcctgcttgg ctctaattgg actcggcaca tgtgccatga tagggttgat agtttacatt   1560
tgtgtattaa ggtcaaaact gtcctctcgg aatttttcgc gcgcgcaaaa tgtaaaacat   1620
agaaattacc agcgacttga gtacgttgct taagcttggc gtaatcatgg tcatagctgt   1680
ttcctgtgtg aaattgttat ccgctcacaa ttccacacaa catacgagcc ggaagcataa   1740
agtgtaaagc ctggggtgcc taatgagtga gctaactcac attaattgcg ttgcgctcac   1800
tgcccgcttt ccagtcggga aacctgtcgt gccagctgca ttaatgaatc ggccaacgcg   1860
cggggagagg cggtttgcgt attgggcgct cttccgcttc ctcgctcact gactcgctgc   1920
gctcggtcgt tcggctgcgg cgagcggtat cagctcactc aaaggcggta atacggttat   1980
ccacagaatc aggggataac gcaggaaaga acatgtgagc aaaaggccag caaaaggcca   2040
ggaaccgtaa aaaggccgcg ttgctggcgt ttttccatag gctccgcccc cctgacgagc   2100
atcacaaaaa tcgacgctca agtcagaggt ggcgaaaccc gacaggacta taaagatacc   2160
aggcgtttcc ccctggaagc tccctcgtgc gctctcctgt tccgaccctg ccgcttaccg   2220
gatacctgtc cgcctttctc ccttcgggaa gcgtggcgct ttctcatagc tcacgctgta   2280
ggtatctcag ttcggtgtag gtcgttcgct ccaagctggg ctgtgtgcac gaaccccccg   2340
ttcagcccga ccgctgcgcc ttatccggta actatcgtct tgagtccaac ccggtaagac   2400
acgacttatc gccactggca gcagccactg gtaacaggat tagcagagcg aggtatgtag   2460
gcggtgctac agagttcttg aagtggtggc ctaactacgg ctacactaga aggacagtat   2520
ttggtatctg cgctctgctg aagccagtta ccttcggaaa aagagttggt agctcttgat   2580
ccggcaaaca aaccaccgct ggtagcggtg gtttttttgt ttgcaagcag cagattacgc   2640
gcagaaaaaa aggatctcaa gaagatcctt tgatcttttc tacggggtct gacgctcagt   2700
ggaacgaaaa ctcacgttaa gggattttgg tcatgagatt atcaaaaagg atcttcacct   2760
agatcctttt aaattaaaaa tgaagtttta aatcaatcta aagtatatat gagtaaactt   2820
ggtctgacag ttaccaatgc ttaatcagtg aggcacctat ctcagcgatc tgtctatttc   2880
gttcatccat agttgcctga ctccccgtcg tgtagataac tacgatacgg gagggcttac   2940
catctggccc cagtgctgca atgataccgc gagacccacg ctcaccggct ccagatttat   3000
cagcaataaa ccagccagcc ggaagggccg agcgcagaag tggtcctgca actttatccg   3060
cctccatcca gtctattaat tgttgccggg aagctagagt aagtagttcg ccagttaata   3120
```

```
gtttgcgcaa cgttgttgcc attgctacag gcatcgtggt gtcacgctcg tcgtttggta   3180

tggcttcatt cagctccggt tcccaacgat caaggcgagt tacatgatcc cccatgttgt   3240

gcaaaaaagc ggttagctcc ttcggtcctc cgatcgttgt cagaagtaag ttggccgcag   3300

tgttatcact catggttatg gcagcactgc ataattctct tactgtcatg ccatccgtaa   3360

gatgcttttc tgtgactggt gagtactcaa ccaagtcatt ctgagaatag tgtatgcggc   3420

gaccgagttg ctcttgcccg gcgtcaatac gggataatac cgcgccacat agcagaactt   3480

taaaagtgct catcattgga aaacgttctt cggggcgaaa actctcaagg atcttaccgc   3540

tgttgagatc cagttcgatg taacccactc gtgcacccaa ctgatcttca gcatctttta   3600

ctttcaccag cgtttctggg tgagcaaaaa caggaaggca aaatgccgca aaaaagggaa   3660

taagggcgac acggaaatgt tgaatactca tactcttcct ttttcaatat tattgaagca   3720

tttatcaggg ttattgtctc atgagcggat acatatttga atgtatttag aaaaataaac   3780

aaataggggt tccgcgcaca tttccccgaa aagtgccacc tgacgtctaa gaaaccatta   3840

ttatcatgac attaacctat aaaaataggc gtatcacgag gccctttcgt ctcgcgcgtt   3900

tcggtgatga cggtgaaaac ctctgacaca tgcagctccc ggagacggtc acagcttgtc   3960

tgtaagcgga tgccgggagc agacaagccc gtcagggcgc gtcagcgggt gttggcgggt   4020

gtcggggctg gcttaactat gcggcatcag agcagattgt actgagagtg caccatatgc   4080

ggtgtgaaat accgcacaga tgcgtaagga gaaaataccg catcaggcgc cattcgccat   4140

tcaggctgcg caactgttgg gaagggcgat cggtgcgggc ctcttcgcta ttacgccagc   4200

tggcgaaagg gggatgtgct gcaaggcgat taagttgggt aacgccaggg ttttcccagt   4260

cacgacgttg taaaacgacg gccagtgaat tcctccgagt accccagagg agtatgtgaa   4320

aagctgccac tcgcaactac tgaagataat ttcaacgctc aagataaatc cggaggagtt   4380

tcctcgagac cccgggtcga ggctcgtgcg cggatacatc gagtattcta gactcgagcg   4440

caagccctac acgcgctacc cctgctttca acgcgtcaac ctgcacattg acggggagtt   4500

tctggttcac aagatgctag cgttcaatgc cgcgatgcgc ccatcggccg aggagctgct   4560

gtcataccca atgtttgctc aactttagga tgactaacct gtttctggga ggagacagcg   4620

tgggcgacgg tgtataaagt tggtctgctt tcaagccctg ccactgcgct acagtgccac   4680

caactgtaaa gcggtagtaa gctgcagtgg tcgactggtg gtagcatata ctaccttatt   4740

tatacgctcc gagctgtttt tcagcatgct agcacccaac gccgagcgag agtatataac   4800

tcccatcatt gcccacaagc ttatgccact tattagcgtc cgctctgccg tttgcttagt   4860

cataatatct accgccgttt acgcagcaga cgctatctgc gacacaattg gatttgcgat   4920

accgcgcatg tggatgtgta ttttaatgag atcaacctcc atgaagcgta actagggggc   4980

ctcccactga ggcactaccg gcttagcagc tgactaacac agtataaaac gtgagaagaa   5040

atcagtctca tgcgccatta gcgctaggct agttagcgtg gaggaccgga gcgctaccgc   5100

cagcagtttc atccgcctgg ttacgggttt gttaacacct accggtgttt taccgctacc   5160

ataggatccg atccatgggc ggccgcggta c                                  5191
```

<210> SEQ ID NO 16
<211> LENGTH: 6892
<212> TYPE: DNA
<213> ORGANISM: Artificial Sequence
<220> FEATURE:
<223> OTHER INFORMATION: Nucleotide sequence of transfer plasmid pU70-
p455-H3-71K71

<400> SEQUENCE: 16
caataaacgc ggtatgtcta ccttcaagcc tatgatgaac ggatgtttgg tgtttgcggc 60
tattataacg ctcttgagtt ttatgctatc tctgggaaca tgcgaaaatt acaggcgtgt 120
ggttcgggat cctagggata acagggtaat cgatttattc aacaaagcca cgttgtgtct 180
caaaatctct gatgttacat tgcacaagat aaaaatatat catcatgaac aataaaactg 240
tctgcttaca taaacagtaa tacaaggggt gttatgagcc atattcaacg ggaaacgtct 300
tgctcgaggc cgcgattaaa ttccaacatg gatgctgatt tatatgggta taaatgggct 360
cgcgataatg tcgggcaatc aggtgcgaca atctatcgat tgtatgggaa gcccgatgcg 420
ccagagttgt ttctgaaaca tggcaaaggt agcgttgcca atgatgttac agatgagatg 480
gtcagactaa actggctgac ggaatttatg cctcttccga ccatcaagca ttttatccgt 540
actcctgatg atgcatggtt actcaccact gcgatccccg ggaaaacagc attccaggta 600
ttagaagaat atcctgattc aggtgaaaat attgttgatg cgctggcagt gttcctgcgc 660
cggttgcatt cgattcctgt ttgtaattgt ccttttaaca gcgatcgcgt atttcgtctc 720
gctcaggcgc aatcacgaat gaataacggt ttggttgatg cgagtgattt tgatgacgag 780
cgtaatggct ggcctgttga acaagtctgg aaagaaatgc ataagctttt gccattctca 840
ccggattcag tcgtcactca tggtgatttc tcacttgata accttatttt tgacgagggg 900
aaattaatag gttgtattga tgttggacga gtcggaatcg cagaccgata ccaggatctt 960
gccatcctat ggaactgcct cggtgagttt tctccttcat tacagaaacg gctttttcaa 1020
aaatatggta ttgataatcc tgatatgaat aaattgcagt ttcatttgat gctcgatgag 1080
tttttctaaa ataaacgcgg tatgtctacc ttcaagccta tgatgaacgg atgtttggtg 1140
tttgcggcta ttataacgct cttgagtttt atgctatctc tgggaacatg cgaaaattac 1200
aggcgtgtgg ttcgggatcc gaccctgttg gtgggtgcgg ttggactcag aatcttggcg 1260
caggcatgga agtttgtcgg tgacgaaaca tacgacacca tccgcgcaga agcaaagaat 1320
ttagagaccc acgtaccctc aagtgctgca gagtcgtctc tagaaaacca atcgacacag 1380
gaggagtcta acagccccga agttgcccac ctgcgaagcg tcaacagcga tgacagtaca 1440
cacacggggg gtgcgtcgaa cggcatccag gactgtgaca gtcagctcaa aactgtgtat 1500
gcctgcttgg ctctaattgg actcggcaca tgtgccatga tagggttgat agtttacatt 1560
tgtgtattaa ggtcaaaact gtcctctcgg aatttttcgc gcgcgcaaaa tgtaaaacat 1620
agaaattacc agcgacttga gtacgttgct taagcttggc gtaatcatgg tcatagctgt 1680
ttcctgtgtg aaattgttat ccgctcacaa ttccacacaa catacgagcc ggaagcataa 1740
agtgtaaagc ctggggtgcc taatgagtga gctaactcac attaattgcg ttgcgctcac 1800
tgcccgcttt ccagtcggga aacctgtcgt gccagctgca ttaatgaatc ggccaacgcg 1860
cggggagagg cggtttgcgt attgggcgct cttccgcttc ctcgctcact gactcgctgc 1920
gctcggtcgt tcggctgcgg cgagcggtat cagctcactc aaaggcggta atacggttat 1980
ccacagaatc aggggataac gcaggaaaga acatgtgagc aaaaggccag caaaaggcca 2040
ggaaccgtaa aaaggccgcg ttgctggcgt ttttccatag gctccgcccc cctgacgagc 2100
atcacaaaaa tcgacgctca agtcagaggt ggcgaaaccc gacaggacta taaagatacc 2160
aggcgtttcc ccctggaagc tccctcgtgc gctctcctgt tccgaccctg ccgcttaccg 2220
gatacctgtc cgcctttctc ccttcgggaa gcgtggcgct ttctcatagc tcacgctgta 2280

```
ggtatctcag ttcggtgtag gtcgttcgct ccaagctggg ctgtgtgcac gaaccccccg   2340
ttcagcccga ccgctgcgcc ttatccggta actatcgtct tgagtccaac ccggtaagac   2400
acgacttatc gccactggca gcagccactg gtaacaggat tagcagagcg aggtatgtag   2460
gcggtgctac agagttcttg aagtggtggc ctaactacgg ctacactaga aggacagtat   2520
ttggtatctg cgctctgctg aagccagtta ccttcggaaa aagagttggt agctcttgat   2580
ccggcaaaca aaccaccgct ggtagcggtg gtttttttgt ttgcaagcag cagattacgc   2640
gcagaaaaaa aggatctcaa gaagatcctt tgatcttttc tacggggtct gacgctcagt   2700
ggaacgaaaa ctcacgttaa gggattttgg tcatgagatt atcaaaaagg atcttcacct   2760
agatcctttt aaattaaaaa tgaagtttta aatcaatcta aagtatatat gagtaaactt   2820
ggtctgacag ttaccaatgc ttaatcagtg aggcacctat ctcagcgatc tgtctatttc   2880
gttcatccat agttgcctga ctccccgtcg tgtagataac tacgatacgg gagggcttac   2940
catctggccc cagtgctgca atgataccgc gagacccacg ctcaccggct ccagatttat   3000
cagcaataaa ccagccagcc ggaagggccg agcgcagaag tggtcctgca actttatccg   3060
cctccatcca gtctattaat tgttgccggg aagctagagt aagtagttcg ccagttaata   3120
gtttgcgcaa cgttgttgcc attgctacag gcatcgtggt gtcacgctcg tcgtttggta   3180
tggcttcatt cagctccggt tcccaacgat caaggcgagt tacatgatcc cccatgttgt   3240
gcaaaaaagc ggttagctcc ttcggtcctc cgatcgttgt cagaagtaag ttggccgcag   3300
tgttatcact catggttatg gcagcactgc ataattctct tactgtcatg ccatccgtaa   3360
gatgcttttc tgtgactggt gagtactcaa ccaagtcatt ctgagaatag tgtatgcggc   3420
gaccgagttg ctcttgcccg gcgtcaatac gggataatac cgcgccacat agcagaactt   3480
taaaagtgct catcattgga aaacgttctt cggggcgaaa actctcaagg atcttaccgc   3540
tgttgagatc cagttcgatg taacccactc gtgcacccaa ctgatcttca gcatctttta   3600
ctttcaccag cgtttctggg tgagcaaaaa caggaaggca aaatgccgca aaaaagggaa   3660
taagggcgac acggaaatgt tgaatactca tactcttcct ttttcaatat tattgaagca   3720
tttatcaggg ttattgtctc atgagcggat acatatttga atgtatttag aaaaataaac   3780
aaataggggt tccgcgcaca tttccccgaa aagtgccacc tgacgtctaa gaaaccatta   3840
ttatcatgac attaacctat aaaaataggc gtatcacgag gccctttcgt ctcgcgcgtt   3900
tcggtgatga cggtgaaaac ctctgacaca tgcagctccc ggagacggtc acagcttgtc   3960
tgtaagcgga tgccgggagc agacaagccc gtcagggcgc gtcagcgggt gttggcgggt   4020
gtcggggctg gcttaactat gcggcatcag agcagattgt actgagagtg caccatatgc   4080
ggtgtgaaat accgcacaga tgcgtaagga gaaaataccg catcaggcgc cattcgccat   4140
tcaggctgcg caactgttgg gaagggcgat cggtgcgggc ctcttcgcta ttacgccagc   4200
tggcgaaagg gggatgtgct gcaaggcgat taagttgggt aacgccaggg ttttcccagt   4260
cacgacgttg taaaacgacg gccagtgaat tcctccgagt accccagagg agtatgtgaa   4320
aagctgccac tcgcaactac tgaagataat ttcaacgctc aagataaatc cggaggagtt   4380
tcctcgagac cccgggtcga ggctcgtgcg cggatacatc gagtattcta gactcgagcg   4440
caagccctac acgcgctacc cctgctttca acgcgtcaac ctgcacattg acggggagtt   4500
tctggttcac aagatgctag cgttcaatgc cgcgatgcgc ccatcggccg aggagctgct   4560
gtcataccca atgtttgctc aactttagga tgactaacct gtttctggga ggagacagcg   4620
tgggcgacgg tgtataaagt tggtctgctt tcaagccctg ccactgcgct acagtgccac   4680
```

```
caactgtaaa gcggtagtaa gctgcagtgg tcgactggtg gtagcatata ctaccttatt   4740
tatacgctcc gagctgtttt tcagcatgct agcacccaac gccgagcgag agtatataac   4800
tcccatcatt gcccacaagc ttatgccact tattagcgtc cgctctgccg tttgcttagt   4860
cataatatct accgccgttt acgcagcaga cgctatctgc gacacaattg gatttgcgat   4920
accgcgcatg tggatgtgta ttttaatgag atcaacctcc atgaagcgta actagggggc   4980
ctcccactga ggcactaccg gcttagcagc tgactaacac agtataaaac gtgagaagaa   5040
atcagtctca tgcgccatta gcgctaggct agttagcgtg gaggaccgga gcgctaccgc   5100
cagcagtttc atccgcctgg ttacgggttt gttaacacct accggtgttt taccgctacc   5160
ataggatccg atccatgggc ggccgcatga agaccgtgat cgccctgagt tacatcttct   5220
gcctggtgtt tgggcaggac ctccctggta aaggcaacaa cacggccacg ctgtgccttg   5280
ggcaccacgc cgtgccgaac ggcacccttg tgaaaactat taccgacgat cagatcgagg   5340
tgaccaacgc caccgaactg gttcagaatt ttagcatggg caaaatttgc aataacccgc   5400
accgcattct ggacggggcc aactgcacgc tgatcgattc attgctgggt gatccccact   5460
gcgatggctt tcaaaacgaa aagtgggact tgttcatcga acgcagcaag gcattcagca   5520
actgctaccc atacgacgtg cccgaataca ccagcctgcg aagcctgatc gcgagctctg   5580
ggaccctgga gttcaccaat gagaacttca attggaccgg agtgacccaa aacggtggct   5640
ccagcgcctg taaaagggga cccaataaca gcttctttag caagttgaat tggctttaca   5700
agagcggcaa tacttacccg atgttgaatg tgaccatgcc caacagtgac gactttgata   5760
aactgtacat atggggcgtg caccatccca gcacggaccg cgaacagata aacctgtacg   5820
tgcaggccag cgggaagata atcgtgagca ccaagcgcag ccagcagacc atcattccca   5880
acattggcag ccgaccgtgg gtgcgcggtc tgagctcccg catcagcata tactggacca   5940
ttgtcaagcc gggagacatc ctgatcatca actctaatgg caatcttatc gccccacgcg   6000
gctacttcaa gatgcagacc ggcaaaagca gtgtgatgag gagcgacgcc cccatcgaca   6060
cctgcaatag cgaatgcatc acccccaatg gcagcatccc caacgacaag cctttccaga   6120
acgtgaataa gatcacctac ggcgcgtgcc ccaagtacat caagcagaac accctgaagc   6180
tggccaccgg catgcgcaac atccccgagc gacagacacg gggcattttt ggcgcaatcg   6240
cagggttcat tgagaatggc tgggagggaa tggttaacgg ctggtacggc ttccgccatc   6300
agaactctga aggaatcggc caagctgcgg atctgaagtc cacgcaagca gccatcaacc   6360
agatcaacgg caagcttaac cgcgtgattg aaaagacgaa cgagaaattc caccaaatag   6420
agaaagaatt cagcgaggtg gagggccgca tccaagacct cgagcgctac gtggaggaca   6480
ccaagatcga cctgtggagc tacaatgccg agctcctggt cgccttggaa aaccaacaca   6540
ccattgacct gaccgacagc gagatgaata aactcttcga gaagacccgg aagcaactcc   6600
gagagaacgc cgaagacatg ggtaatgggt gttttaagat ctaccacaag tgcgacaata   6660
gctgcatgga gagcatccga aacggaacct acgaccacaa cgagtaccgc gatgaggcag   6720
ttaataaccg cttccaaatc aaaagcgtgg aactgaagag tggctataag gactggatac   6780
tgtggatcag ctttgccata agctgcttcc tgctgtgcgc cgtttggttg ggtttcatca   6840
tgtgggcctg tcaaaagggc aatattcgct gtaacatctg catttgaggt ac            6892
```

<210> SEQ ID NO 17
<211> LENGTH: 417
<212> TYPE: DNA

<213> ORGANISM: Equine herpesvirus 1

<400> SEQUENCE: 17
ctccgagtac cccagaggag tatgtgaaaa gctgccactc gcaactactg aagataattt 60
caacgctcaa gataaatccg gaggagtttc ctcgagaccc cgggtcgagg ctcgtgcgcg 120
gatacatcga gtattctaga ctcgagcgca agccctacac gcgctacccc tgctttcaac 180
gcgtcaacct gcacattgac ggggagtttc tggttcacaa gatgctagcg ttcaatgccg 240
cgatgcgccc atcggccgag gagctgctgt catacccaat gtttgctcaa ctttaggatg 300
actaacctgt ttctgggagg agacagcgtg ggcgacggtg tataaagttg gtctgctttc 360
aagccctgcc actgcgctac agtgccacca actgtaaagc ggtagtaagc tgcagtg 417

<210> SEQ ID NO 18
<211> LENGTH: 431
<212> TYPE: DNA
<213> ORGANISM: Equine herpesvirus 1

<400> SEQUENCE: 18
gaccctgttg gtgggtgcgg ttggactcag aatcttggcg caggcatgga agtttgtcgg 60
tgacgaaaca tacgacacca tccgcgcaga agcaaagaat ttagagaccc acgtaccctc 120
aagtgctgca gagtcgtctc tagaaaacca atcgacacag gaggagtcta acagccccga 180
agttgcccac ctgcgaagcg tcaacagcga tgacagtaca cacacggggg gtgcgtcgaa 240
cggcatccag gactgtgaca gtcagctcaa aactgtgtat gcctgcttgg ctctaattgg 300
actcggcaca tgtgccatga tagggttgat agtttacatt tgtgtattaa ggtcaaaact 360
gtcctctcgg aatttttcgc gcgcgcaaaa tgtaaaacat agaaattacc agcgacttga 420
gtacgttgct t 431

<210> SEQ ID NO 19
<211> LENGTH: 417
<212> TYPE: DNA
<213> ORGANISM: Equine herpesvirus 1

<400> SEQUENCE: 19
ctccgagtac cccagaggag tatgtgaaaa gctgccactc gcaactactg aagataattt 60
caacgctcaa gataaatccg gaggagtttc ctcgagaccc cgggtcgagg ctcgtgcgcg 120
gatacatcga gtattctaga ctcgagcgca agccctacac gcgctacccc tgctttcaac 180
gcgtcaacct gcacattgac ggggagtttc tggttcacaa gatgctagcg ttcaatgccg 240
cgatgcgccc atcggccgag gagctgctgt catacccaat gtttgcacaa ctttaggatg 300
actaacctgt ttctgggagg agacagcgtg ggcgacggtg tataaagttg gtctgctttc 360
aagccctgcc actgcgctac agtgccacca actgtaaagc ggtagtaagc tgcagtg 417

<210> SEQ ID NO 20
<211> LENGTH: 431
<212> TYPE: DNA
<213> ORGANISM: Equine herpesvirus 1

<400> SEQUENCE: 20
gaccctgttg gtgggtgcgg ttggactcag aatcttggcg caggcatgga agtttgtcgg 60
tgacgaaaca tacgacacca tccgcgcaga agcaaagaat ttagagaccc acgtaccctc 120
aagtgctgca gagtcgtctc tagaaaacca atcgacacag gaggagtcta acagccccga 180
agttgcccac ctgcgaagcg tcaacagcga tgacagtaca cacacggggg gtgcgtcgaa 240
cggcatccag gactgtgaca gtcagctcaa aactgtgtat gcctgcttgg ctctaattgg 300
actcggcaca tgtgccatga tagggttgat agtttacatt tgtgtattaa ggtcaaaact 360
gtcctctcgg aatttttcgc gcgcgcaaaa tgtaaaacat agaaattacc agcgacttga 420
gtacgttgct t 431

<210> SEQ ID NO 21
<211> LENGTH: 283
<212> TYPE: DNA
<213> ORGANISM: Equine herpesvirus 1

<400> SEQUENCE: 21
tctagactcg agcgcaagcc ctacacgcgc taccccctgct ttcaacgcgt caacctgcac 60
attgacgggg agtttctggt tcacaagatg ctagcgttca atgccgcgat gcgcccatcg 120
gccgaggagc tgctgtcata cccaatgttt gctcaacttt aggatgacta acctgtttct 180
gggaggagac agcgtgggcg acggtgtata aagttggtct gctttcaagc cctgccactg 240
cgctacagtg ccaccaactg taaagcggta gtaagctgca gtg 283

<210> SEQ ID NO 22
<211> LENGTH: 144
<212> TYPE: DNA
<213> ORGANISM: Equine herpesvirus 1

<400> SEQUENCE: 22
gaccctgttg gtgggtgcgg ttggactcag aatcttggcg caggcatgga agtttgtcgg 60
tgacgaaaca tacgacacca tccgcgcaga agcaaagaat ttagagaccc acgtaccctc 120
aagtgctgca gagtcgtctc taga 144

<210> SEQ ID NO 23
<211> LENGTH: 801
<212> TYPE: DNA
<213> ORGANISM: Equine herpesvirus 1

<400> SEQUENCE: 23
atgttgactg tcttagcagc cctgagtctg ctcagcttgc ttacgagcgc aaccggacgg 60
ctcgccccag atgaactctg ttatgccgaa ccccgcagaa ctggcagccc accaaacacc 120
cagcccgaac gcccacccgt aatatttgag cccccaacaa ttgcgattaa agctgaatcc 180
aagggttgtg agctaatttt attagatcca cccatagatg taagctatcg cagagaagat 240
aaggtgaatg cgtccattgc ttggtttttt gactttggcg cttgccggat gcccatcgca 300
tacagagagt attacggttg tattggcaat gctgttccct ccccagagac ttgtgatgcg 360
tactcattta cccttattag gaccgagggt atcgtggagt ttaccatcgt aaacatgagc 420
ctcctgtttc agcctggaat atacgatagt ggcaatttta tctacagcgt tctcctggac 480
taccacatat ttacaggacg tgtaacgttg gaagtggaaa aggacacaaa ctatccctgt 540
ggcatgattc atggactcac tgcttacgga aacatcaacg tagatgaaac catggacaac 600
gccagcccac acccgcgtgc cgtggggtgc tttcccgagc ccatcgacaa cgaagcgtgg 660
gcaaacgtta catttactga attggggata ccagacccaa actcatttct cgatgacgag 720
ggtgattacc cgaatatatc agactgtcac tcgtgggagt catacaccta cccaaatacg 780
ctgaggcagg ccacaggacc c 801

<210> SEQ ID NO 24

-continued

```
<211> LENGTH: 801
<212> TYPE: DNA
<213> ORGANISM: Equine herpesvirus 1

<400> SEQUENCE: 24

atgttgactg tcttagcagc tctgagtctg ctcagcttgc ttacgagcgc aaccggacgg      60

ctcgccccag atgaactctg ttatgccgaa ccccgcagaa ctggcagccc accaaacacc     120

cagcccgaac gcccacccgt aatatttgag cccccaacaa ttgcgattaa agctgaatcc     180

aagggttgtg agctaatttt attagatcca cccatagatg taagctatcg cagagaagat     240

aaggtgaatg cgtccattgc ttggtttttt gactttggcg cttgccggat gcccatcgca     300

tacagagagt attacggttg tattggcaat gctgttccct ccccagagac ttgtgatgcg     360

tactcattta cccttattag gaccgagggt atcgtggagt ttaccatcgt aaacatgagc     420

ctcctgtttc agcctggaat atacgatagt ggcaatttta tctacagcgt tctcctggac     480

taccacatat ttacaggacg tgtaacgttg gaagtggaaa aggacacaaa ctatccctgt     540

ggcatgattc atggactcac tgcttacgga aacatcaacg tagatgaaac catggacaac     600

gccagcccac acccgcgtgc cgtggggtgc tttcccgagc ccatcgacaa cgaagcgtgg     660

gcaaacgtta catttactga attggggata ccagacccaa actcatttct cgatgacgag     720

ggtgattacc cgaatatatc agactgtcac tcgtgggagt catacaccta cccaaatacg     780

ctgaggcagg ccacaggacc c                                               801
```

EHV WITH INACTIVATED UL18 AND/OR UL8

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

A. Field of the Invention

The present invention relates to the field of (vector) vaccines, and especially to the inactivation of UL18 and/or UL8 in EHV. The present invention further relates to replication deficient EHV's having an inactivation of UL18 and/or UL8. The present invention further concerns related expression cassettes and vectors, which are suitable to express genes of interest, especially antigen encoding sequences. The viral vectors of the present invention are useful for producing an immunogenic composition or vaccine.

B. Background and Description of the Related Art

The horse pathogen Equid Alphaherpesvirus 1 (Equine abortion virus, EHV-1) belongs to the genus *Varicellovirus* in the subfamily Alphaherpesvirinae in the family Herpesviridae in the order Herpesvirales. It is a large, enveloped virus with a double-stranded DNA genome of approximately 150,000 base pairs. Other important members of the subgenus *Varicellovirus* are the Human Alphaherpesvirus 3 (Varicella Zoster Virus), Suid Alphaherpesvirus 1 (Pseudorabies virus), Bovine Alphaherpesvirus 1 (Infectious Bronchitis Virus), and Equid Alphaherpesvirus 4 (Equine Rhinopneumitis Virus, EHV-4) (Virus Taxonomy: 2015 Release EC 47, London, UK, July 2015; Email ratification 2016 (MSL #30)). EHV-1 and EHV-4 are endemic and affecting horses throughout the world. While EHV-4 causes a mostly mild infection of the upper respiratory tract, EHV-1 can cause systemic infection with a range of diseases from respiratory symptoms to abortion and lethal myeloencephalopathy depending on the strain and the immunological status of the host. Two licensed modified live vaccines (MLV) against EHV-1 are currently available in the USA and Europe, respectively, Rhinomune® (Boehringer Ingelheim) and Prevaccinol® (MSD). Both contain the classically attenuated EHV-1 RacH strain, which was passaged 256 times in porcine epithelial cells for attenuation (Ma et al. 2013). The mechanism of attenuation has been investigated on the molecular level. Osterrieder et al. (1996) showed that RacH lacks the two genomic copies of orf67 (IR6) and that restoration of one copy was sufficient to restore virulence. In addition, RacH carries a 1283 bp deletion removing more than 90% of the coding sequence of orf1 (UL56) which encodes an immunosuppressive viral protein. Other mutations might also influence attenuation, but have not been investigated in detail, so far. All this makes RacH a very safe vaccine strain as a reversion to virulence by passaging in vaccinated animals is highly unlikely, if possible at all.

Two variants of an *E. coli* bacterial artificial chromosome (BAC) harboring the entire genome of the Equid Alphaherpes Virus 1 (EHV-1) vaccine strain RacH: pRacH and pRacH-SE are known as a platform for vector vaccine development. The BAC pRacH-SE was created on the basis of pRacH, a BAC originally cloned in the lab of Klaus Osterrieder, FU Berlin. pRacH has a deletion of orf71 (US5) encoding glycoprotein II (gpII; Wellington et al., 1996). In its place the BAC-vector sequences and a GFP-expression cassette were introduced. In order to rescue unmodified EHV-1 RacH from pRacH, it had to be co-transfected with a plasmid containing the entire orf71 (US5) plus flanking regions, so that during the course of viral replication the BAC-vector sequence portions and the GFP-expression cassette were replaced by orf71 (US5) through homologous recombination so that the original RacH genome would be restored. pRacH was modified in the present invention so that the BAC-vector sequences/GFP-expression cassette became self-excisable (SE) upon transfection in cell cultures (Tischer et al., 2007). This improved BAC was designated pRacH-SE. pRacH and pRacH-SE can both serve as platforms for vector vaccine development, with the only difference that pRacH-SE facilitates rescue of orf71 (US5)-repaired virus significantly.

It has been shown that EHV-1 RacH-based vector vaccines are able to elicit immunity in several mammalian species including pigs, cattle, and dogs (Rosas et al. 2007, Rosas et al. 2008, Trapp et al. 2005, Said et al. 2013). Genes coding for antigenic proteins of pathogens can be expressed by recombinant EHV-1 RacH. The EHV-1-RacH genome is manipulated in its BAC form in *E. coli* and tailored to express additional proteins usually by inserting transgene expression cassettes (Tischer et al., 2010). Upon transfection of pRacH-SE DNA in cultured permissive cells, EHV-1 replication is initiated by cellular transcription factors. Activity of the viral DNA polymerase leads to deletion of all BAC-vector related sequences and restoration of the EHV-1 RacH genome to its original state. Infectious virus is generated which is indistinguishable from RacH.

When pRacH-SE is manipulated in *E. coli* e.g. by insertion of transgene expression cassettes, virus reconstituted after transfection in permissive cells will carry the modification and will express the additional gene. The recombinant EHV-1 RacH can be used as a vector vaccine.

Wild-type EHV-1 strains possess three open reading frames (orf) called orf1 (UL56), orf 2 and orf3 at one end of the long unique segment of their genome (sequence coordinates 1298-3614; FIG. 1). Orf1 (UL56) and orf3 are serially arranged on one strand of the DNA while orf 2 is encoded by the complementary strand. The vaccine strain RacH has a 1283 bp deletion in that region affecting orfs 1 and 2 indicating that these genes are non-essential for viral replication. For this reason the site serves as a transgene insertion site. This insertion site is called ORF1/3 (UL56).

However, the size and number of transgenes that may be inserted into the ORF1/3 (UL56) insertion site is usually limited. Thus, in order to augment the capabilities of the EHV vector there is an unmet need for new and alternative ways to insert and express transgenes from the EHV vector, especially the recombinant EHV-1 RacH vector.

It may be beneficial to have a replication-deficient EHV vectored vaccine. Such a replication-deficient EHV vectored vaccine cannot replicate in the host animal and does not spread from one animal to another animal and, therefore, is advantageous for safety or regulatory reasons.

Barnard et al 1997 (Virology; 237, 97-106) describes that some mutants of UL8 in Herpes Simplex Virus Type 1 show some inhibition of replication. Further, Muylaert et al 2012 (Journal of Biological Chemistry; VOL. 287, NO. 40, pp. 33142-33152) describes some mutants of UL8 in Herpes Simplex Virus Type 1 having defects in DNA Synthesis. In addition, some mutations were introduced into EHV and similar phenotypes were observed when the corresponding mutations were introduced into EHV-1 UL8.

CN 105641692 A describes the complete deletion (knock out) of UL18 in the Herpes Simplex Virus Type 1 (HSV-1). However, CN 105641692 A describes that the plaque inhibition rate is reduced for said HSV-1 UL18 knock out by about 80%, but the replication was not completely abolished. Further, CN 105535959 also studies the phenotype of the HSV-1 UL18 knock out and describes that replication and infection was significantly lower and that almost no infection was observed. Thus, in regard to replication, CN 105535959 describes a similar phenotype as CN 105641692 A (a reduction, but not complete abolishment of replication). Further, CN 105535959 describes almost no infection for the HSV-1 UL18 knock out which is problematic for a vectored vaccine (such as a recombinant EHV vaccine) because the vectored vaccines have to infect the host cells for providing an adequate immune response. In particular, infectivity and transgene expression in infected cells are essential for vectored vaccines expressing foreign antigens to be efficacious. Thus, there is an unmet need for replication-deficient (but infective) EHV vector systems.

SUMMARY OF THE INVENTION

In order to augment the capabilities of the EHV vector, the present invention provides ways to produce replication deficient EHV's and to insert and express transgenes from the EHV vector backbone.

The present invention concerns replication deficient EHV's comprising an inactivation of UL18 and/or UL8 and new, alternative transgene insertion sites UL18 and/or UL8 that can be used to insert transgenic sequences and express transgenic proteins from an EHV vector.

The inactivation of UL8 and/or UL18 is a complete or partial deletion, a complete or partial truncation, a complete or partial substitution, a complete or partial inversion, an insertion.

The present invention further concerns mammalian host cells comprising a replication deficient EHV vector of the present invention.

The present invention further concerns cell lines expressing UL8 and/or UL18 of EHV or functional parts thereof for culturing the replication deficient EHV vector of the present invention.

The present invention further concerns cell lines comprising a plasmid comprising an expression cassette comprising UL8 and/or UL18 of EHV or functional parts thereof, wherein the cell line is expressing UL8 and/or UL18 or functional parts thereof.

The present invention further concerns methods for producing a replication deficient Equid Alphaherpesvirus (EHV) comprising inactivating UL18 and/or UL8 according to the present invention.

The present invention further concerns methods for producing a replication deficient Equid Alphaherpesvirus (EHV) comprising the steps of:

a) providing a wild-type EHV or an attenuated EHV;
b) inactivating UL18 and/or UL8 of the EHV of step a) and selecting for EHV clones which are not carrying complete or functional part of UL18 and/or UL 8;
c) providing a complementing cell line expressing UL18 and/or UL8 or functional parts thereof;
d) obtaining the replication deficient Equid Alphaherpesvirus (EHV) by cultivating the EHV from step b) with the complementing cell line from step c).

The present invention further concerns immunogenic compositions comprising one or more EHV vectors of the present invention.

The present invention further concerns methods for immunizing a subject comprising administering to such subject an immunogenic composition of the present invention.

The present invention further concerns methods of treating or preventing clinical signs caused by a pathogen in a subject of need, the method comprising administering to the subject a therapeutically effective amount of an immunogenic composition of the present invention.

Thus, the solution to the above described technical problem is achieved by the description and the embodiments characterized in the claims and the invention in its different aspects is implemented according to the claims.

These properties allow creation of recombinant vector vaccines based on EHV being replication deficient by inactivating of UL18 and/or UL8. Further, antigens can be inserted into said EHV vector. At least one antigen from another insertion site ORF1/3 (UL56) and/or US4 (ORF70) or at least two different antigens in parallel with similar efficiency can be expressed from ORF1/3 (UL56) and/or US4 (ORF70). Further, at least one antigen from the newly described UL18 and/or UL8 insertion site or at least two different antigens in parallel with similar efficiency from the newly described UL18 and/or UL8 can be expressed. Furthermore, antigens from both the newly described UL18 and/or UL8 insertion site and said other insertion site ORF1/3 (UL56) and/or US4 (ORF70) can be expressed. The replication deficient EHV vector vaccine is advantegous for safety and regulatory reasons. Further, if a vaccine target consists of two or more different pathogens/antigens the application of the new UL18 and/or UL8 insertion site in parallel with an established insertion site like ORF1/3 (UL56) and/or US4 (ORF70) can reduce cost of goods significantly and represents a clear advantage over a vector expressing only one antigenic component.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

$U_L$=long unique segment
$U_S$=short unique segment
IR=inner inverted repeat
TR=terminal inverted repeat
orf=open reading frame
bp=base pairs

$U_L$=long unique segment
$U_S$=short unique segment
IR=inner inverted repeat
TR=terminal inverted repeat
orf=open reading frame
bp=base pairs

DETAILED DESCRIPTION OF THE INVENTION

Figure 1:
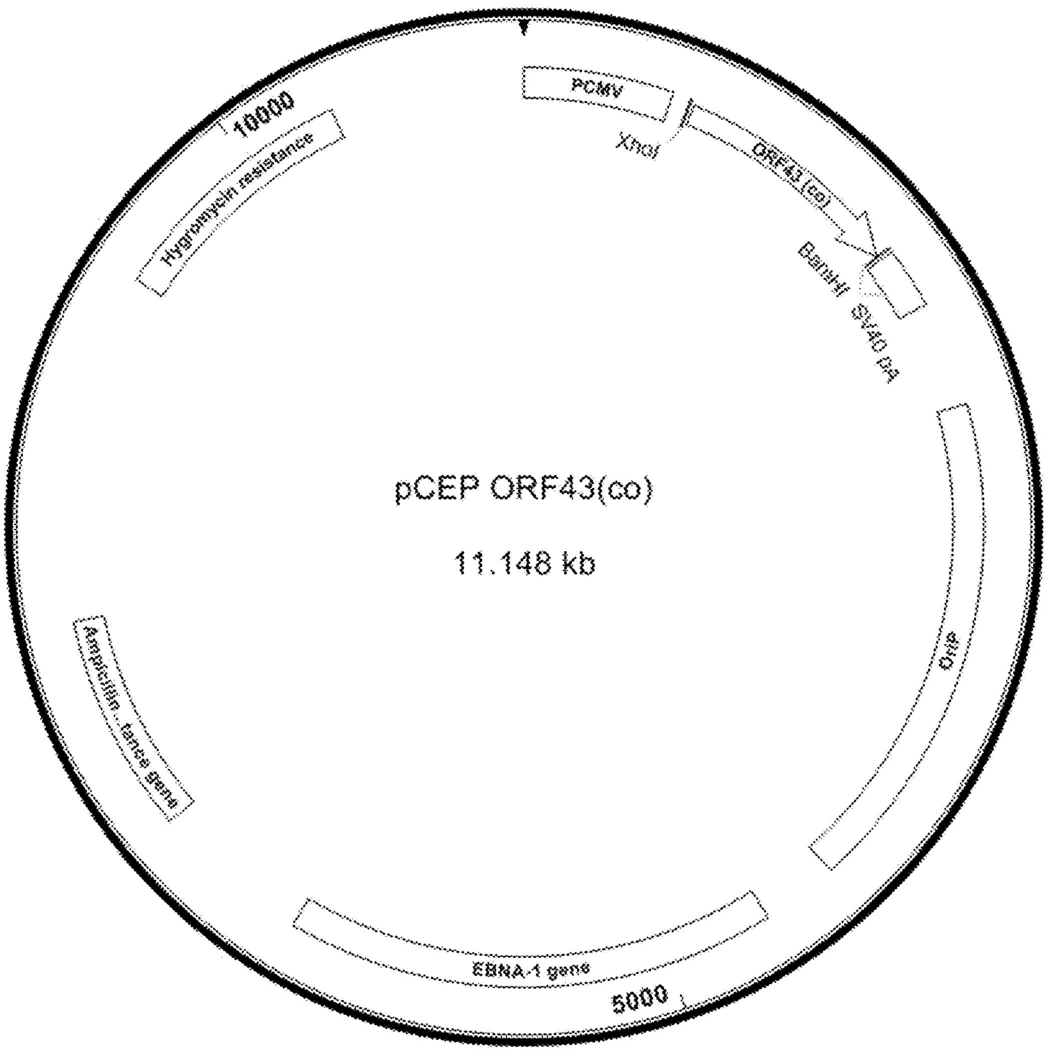
FIG. 1: Plasmid map of the expression plasmid, pCEP-ORF43(CO). This vector expresses a codon-optimized EHV-1 ORF43 gene through a CMV promoter and was used to generate one of the stable cell lines.

The present invention solves the problems inherent in the prior art and provides a distinct advance in the state of the art.

The present invention further concerns an Equid herpesvirus (EHV), specifically an Equid Alphaherpesvirus such as EHV-1, EHV-3, EHV-4, EHV-8 and EHV-9, more specifically an Equid Alphaherpesvirus 1 (EHV-1) vector, most specifically strain RacH, comprising an inactivation of UL18 and/or UL8.

Generally, the present invention provides a replication deficient Equid Alphaherpesvirus (EHV) vector, preferably strain RacH, comprising an inactivation of UL18 and/or UL8.

Advantagously, the EHV vectors as described herein have a replication deficient phenotype. Such replication-deficient EHV vector vaccine does not replicate in the host animal and does not spread from one animal to another animal and, therefore, is advantegous for safety or regulatory reasons.

In one aspect of the vector of the present invention UL18 is inactivated.

In another aspect of the vector of the present invention UL8 is inactivated.

In another aspect of the vector of the present invention UL18 and UL8 are inactivated.

Inactivation UL18 and UL8

In another aspect of the vector of the present invention the inactivation of UL18 is a complete or partial deletion, a complete or partial truncation, a complete or partial substitution, a complete or partial inversion, an insertion.

In another aspect of the vector of the present invention the inactivation of UL8 is a complete or partial deletion, a complete or partial truncation, a complete or partial substitution, a complete or partial inversion, an insertion.

In another aspect of the vector of the present invention the start codon of UL18 (ATG, nucleotides 1-3 of SEQ ID NO:1) is inactivated.

In another aspect of the vector of the present invention said inactivation of the start codon (ATG) of UL18 is a deletion, substitution, inversion or insertion.

In another aspect of the vector of the present invention the start codon of UL8 (ATG, nucleotides 1-3 of SEQ ID NO:2) is inactivated.

In another aspect of the vector of the present invention said inactivation of the start codon (ATG) of UL8 is a deletion, substitution, inversion or insertion.

Inactivation UL18

In another aspect of the vector of the present invention at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 925 nucleotides, at least 940 nucleotides from the 5'-Terminus of the start codon (ATG, nucleotides 1-3 of SEQ ID NO:1) of the UL18 are deleted, substituted or inverted.

In another aspect of the vector of the present invention at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 925 nucleotides, at least 940 nucleotides from the A, T, or G of the start codon (ATG, nucleotides 1-3 of SEQ ID NO:1) of the UL18 are deleted, substituted or inverted.

In another aspect of the vector of the present invention at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 925 nucleotides, at least 940 nucleotides are deleted, substituted, or inverted within the UL18.

In another aspect of the vector of the present invention a DNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the DNA sequence as set forth in SEQ ID NO:1 is deleted, substituted, or inverted within the UL18.

In another aspect of the vector of the present invention at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 300 nucleotides, at least 500 nucleotides, at least 800 nucleotides, at least 1000 nucleotides are inserted within the UL18.

Inactivation UL8

In another aspect of the vector of the present invention wherein at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 1000 nucleotides, at least 1250 nucleotides, at least 1500, nucleotides, at least 1750 nucleotides, at least 2000 nucleotides, at least 2225 nucleotides from the 5'-Terminus of the start codon (ATG, nucleotides 1-3 of SEQ ID NO:2) of the UL8 are deleted, substituted or inverted.

In another aspect of the vector of the present invention at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 1000 nucleotides, at least 1250 nucleotides, at least 1500, nucleotides, at least 1750 nucleotides, at least 2000 nucleotides, at least 2225 nucleotides from the A, T, or G of the start codon (ATG, nucleotides 1-3 of SEQ ID NO:2) of the UL8 are deleted, substituted or inverted.

In another aspect of the vector of the present invention at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 1000 nucleotides, at least 1250 nucleotides, at least 1500, nucleotides, at least 1750 nucleotides, at least 2000 nucleotides, at least 2225 nucleotides are deleted, substituted, or inverted within the UL8.

In another aspect of the vector of the present invention a DNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the DNA sequence as set forth in SEQ ID NO:2 is deleted, substituted, or inverted within the UL8.

In another aspect of the vector of the present invention at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 300 nucleotides, at least 500 nucleotides, at least 800 nucleotides, at least 1000 nucleotides are inserted within the UL8.

Expression Cassette

In another aspect of the vector of the present invention the EHV vector comprises an expression cassette comprising:

(i) at least one exogenous nucleotide sequence of interest, preferably a gene of interest, more preferably an antigen encoding sequence, wherein said nucleotide sequence of interest, preferably a gene of interest, more preferably an antigen encoding sequence, is operably linked to a promoter sequence, and (ii) at least one upstream UL18 flanking region selected from the group consisting of: SEQ ID NO:5 and a 70%, 80%, 85%, 90%, 91%, 92%, 93%, 94%, 95%, 96%, 97%, 98%, 99% homologous and/or identical sequence thereof, SEQ ID NO:9 and a 70%, 80%, 85%, 90%, 91%, 92%, 93%, 94%, 95%, 96%, 97%, 98%, 99% homologous and/or identical sequence thereof, and (iii) at least one downstream UL18 flanking region selected from the group consisting of: SEQ ID NO.: 6 and a 70%, 80%, 85%, 90%, 91%, 92%, 93%, 94%, 95%, 96%, 97%, 98%, 99% homologous and/or identical sequence thereof, SEQ ID NO:10 and a 70%, 80%, 85%, 90%, 91%, 92%, 93%, 94%, 95%, 96%, 97%, 98%, 99% homologous and/or identical sequence thereof.

In another aspect of the vector of the present invention the EHV vector comprises an expression cassette comprising:

(i) at least one exogenous nucleotide sequence of interest, preferably a gene of interest, more preferably an antigen encoding sequence, wherein said nucleotide sequence of interest, preferably a gene of interest, more preferably an antigen encoding sequence, and (ii) at least one upstream UL18 flanking region selected from the group consisting of: SEQ ID NO:5 and a 70%, 80%, 85%, 90%, 91%, 92%, 93%, 94%, 95%, 96%, 97%, 98%, 99% homologous and/or identical sequence thereof, SEQ ID NO.: 9 and a 70%, 80%, 85%, 90%, 91%, 92%, 93%, 94%, 95%, 96%, 97%, 98%, 99% homologous and/or identical sequence thereof, and (iii) at least one downstream UL18 flanking region selected from the group consisting of: SEQ ID NO:6 and a 70%, 80%, 85%, 90%, 91%, 92%, 93%, 94%, 95%, 96%, 97%, 98%, 99% homologous and/or identical sequence thereof, SEQ ID NO:10 and a 70%, 80%, 85%, 90%, 91%, 92%, 93%, 94%, 95%, 96%, 97%, 98%, 99% homologous and/or identical sequence thereof.

In another aspect of the vector of the present invention the EHV vector comprises an expression cassette comprising:

(i) at least one exogenous nucleotide sequence of interest, preferably a gene of interest, more preferably an antigen encoding sequence, wherein said nucleotide sequence of interest, preferably a gene of interest, more preferably an antigen encoding sequence is operably linked to a promoter sequence, and (ii) at least one upstream UL8 flanking region selected from the group consisting of: SEQ ID NO:11 and a 70%, 80%, 85%, 90%, 91%, 92%, 93%, 94%, 95%, 96%, 97%, 98%, 99% homologous and/or identical sequence thereof, and (iii) at least one downstream UL8 flanking region selected from the group consisting of: SEQ ID NO: 12 and a 70%, 80%, 85%, 90%, 91%, 92%, 93%, 94%, 95%, 96%, 97%, 98%, 99% homologous and/or identical sequence thereof.

In another aspect of the vector of the present invention the EHV vector comprises an expression cassette comprising:

(i) at least one exogenous nucleotide sequence of interest, preferably a gene of interest, more preferably an antigen encoding sequence, wherein said nucleotide sequence of interest, preferably a gene of interest, more preferably an antigen encoding sequence, and (ii) at least one upstream UL8 flanking region selected from the group consisting of: SEQ ID NO:11 and a 70%, 80%, 85%, 90%, 91%, 92%, 93%, 94%, 95%, 96%, 97%, 98%, 99% homologous and/or identical sequence thereof, and (iii) at least one downstream UL8 flanking region selected from the group consisting of: SEQ ID NO:12 and a 70%, 80%, 85%, 90%, 91%, 92%, 93%, 94%, 95%, 96%, 97%, 98%, 99% homologous and/or identical sequence thereof.

In another aspect of the vector of the present invention the insertion of the expression cassette inactivates UL18 and/or UL8.

Deletion by Inserting Expression Cassette into UL18

In another aspect of the vector of the present invention the insertion of the expression cassette into UL18 is characterized by a deletion of an approximately 945 bp portion within UL18 for RacH (SEQ ID NO:1) or a 70%, 80%, 85%, 90%, 91%, 92%, 93%, 94%, 95%, 96%, 97%, 98%, 99% homologous and/or identical sequence thereof.

Deletion by Inserting Expression Cassette into UL8

In another aspect of the vector of the present invention the insertion of the expression cassette into UL8 is characterized by a deletion of an approximately 2256 bp portion within UL8 for RacH (SEQ ID NO:2) or a 70%, 80%, 85%, 90%, 91%, 92%, 93%, 94%, 95%, 96%, 97%, 98%, 99% homologous and/or identical sequence thereof.

Flanking Regions for UL18

In another aspect of the vector of the present invention the EHV comprises at least one flanking region selected from the group consisting of: SEQ ID NO:5, SEQ ID NO:6, SEQ ID NO:9, SEQ ID NO:10, and a 70%, 80%, 85%, 90%, 91%, 92%, 93%, 94%, 95%, 96%, 97%, 98%, 99% homologous and/or identical sequence of any one of these sequences.

In another aspect of the vector of the present invention the EHV comprises (i) at least one upstream UL18 flanking region selected from the group consisting of: SEQ ID NO:5 and SEQ ID NO:9, and (ii) at least one downstream UL18 flanking region selected from the group consisting of: SEQ ID NO:6 and SEQ ID NO:10.

Flanking Regions for UL8

In another aspect of the vector of the present invention the EHV comprises at least one flanking region selected from the group consisting of: SEQ ID NO:11 and SEQ ID NO:12 and a 70%, 80%, 85%, 90%, 91%, 92%, 93%, 94%, 95%, 96%, 97%, 98%, 99% homologous and/or identical sequence of any one of these sequences.

In another aspect of the vector of the present invention the EHV comprises (i) at least one upstream UL8 flanking region selected from the group consisting of: SEQ ID NO:11 and (ii) at least one downstream UL8 flanking region selected from the group consisting of: SEQ ID NO:12.

The present invention further concerns a plasmid comprising the flanking regions for homologous recombination or RED-mediated recombination (see both described above) into a specific target site in the viral vector genome, preferably into the UL18 and/or UL8 site of the EHV vector, specifically the EHV-1, more specifically the RacH vector.

Recombinant EHV

In another aspect of the vector of the present invention said EHV vector is a non-naturally and/or recombinant EHV.

Functional Definition for Replication Deficient

In another aspect of the vector of the present invention replication deficient means that the replication rate is reduced at least by 90%.

In another aspect of the vector of the present invention replication deficient means that the replication rate is reduced at least by 95%.

In another aspect of the vector of the present invention replication deficient means that the replication rate is reduced at least by 99%.

In another aspect of the vector of the present invention replication deficient means that the replication rate is reduced at least by 99.5%.

In another aspect of the vector of the present invention replication deficient means that the replication rate is reduced at least by 99.75%.

In another aspect of the vector of the present invention replication deficient means that the replication rate is abolished completely.

In another aspect of the vector of the present invention the replication rate is measured by a $TCID_{50}$ assay.

In another aspect of the vector of the present invention the replication deficient EHV vector is still infective.

Advantagously, the EHV vector of as described herein has a replication deficient phenotype, but still is infective. An infectivity is necessary because the virus vaccine has to infect the host cells for providing adequate immune response. In particular, infectivity is needed for virus vector vaccines expressing foreign antigens.

In another aspect of the vector of the present invention the EHV is still infective, can replicate in infected eukaryotic cell lines, but only be packaged as a replication-competent virus in complementing cell lines. Advantagously, virus DNA and virus protein are still produced in the host and, thus, the replication defective EHV of the present invention still induces an immune response and/or protective immunity. Advantagously, the data of the present invention show that protein expression (marker protein expression) still occurs in the replication defective EHV virus of the present invention.

Insertion into UL56 or US4

In a further specific aspect of the vector of the present invention said EHV vector further comprises at least one further nucleotide sequence of interest, preferably another gene of interest, more preferably an antigen encoding sequence. In one aspect at least one further nucleotide sequence of interest, preferably another gene of interest, more preferably an antigen encoding sequence, is inserted into the same insertion site UL18 and/or UL8, e.g. via IRES/2a peptide(s). In another aspect said vector or expression cassette comprise at least one further nucleotide sequence of interest, preferably another gene of interest, more preferably an antigen encoding sequence, is inserted into another insertion site, preferably into UL56 and/or US4.

In another aspect of the vector of the present invention the EHV vector comprises at least one nucleotide sequence of interest, preferably a gene of interest, more preferably an antigen encoding sequence, inserted into an insertion site, preferably UL56 and/or US4.

In another aspect of the vector of the present invention the EHV vector comprises an inactivation of UL18 and/or UL8 and at least one nucleotide sequence of interest, preferably a gene of interest, more preferably an antigen encoding sequence inserted into UL56 and/or US4.

In another aspect of the vector of the present invention the EHV vector comprises an inactivation of UL18 and at least one nucleotide sequence of interest, preferably a gene of interest, more preferably an antigen encoding sequence inserted into UL56 (monovalent vaccine).

In another aspect of the vector of the present invention the EHV vector comprises an inactivation of UL18 and at least one nucleotide sequence of interest, preferably a gene of interest, more preferably an antigen encoding sequence inserted into US4 (monovalent vaccine).

In another aspect of the vector of the present invention the EHV vector comprises an inactivation of UL8 and at least one nucleotide sequence of interest, preferably a gene of interest, more preferably an antigen encoding sequence inserted into UL56 (monovalent vaccine).

In another aspect of the vector of the present invention the EHV vector comprises an inactivation of UL8 and at least one nucleotide sequence of interest, preferably a gene of interest, more preferably an antigen encoding sequence inserted into US4 (monovalent vaccine).

In another aspect of the vector of the present invention the EHV vector comprises an inactivation of UL18 and at least one nucleotide sequence of interest, preferably a gene of interest, more preferably an antigen encoding sequence inserted into UL56 and US4 (bivalent vaccine).

In another aspect of the vector of the present invention the EHV vector comprises an inactivation of UL8 and at least one nucleotide sequence of interest, preferably a gene of interest, more preferably an antigen encoding sequence inserted into UL56 and US4 (bivalent vaccine).

The present invention further concerns an Equid herpesvirus (EHV), specifically an Equid Alphaherpesvirus such as EHV-1, EHV-3, EHV-4, EHV-8 and EHV-9, more specifically an Equid Alphaherpesvirus 1 (EHV-1) vector, most specifically strain RacH, comprising a first nucleotide sequence or gene of interest, preferably an antigen encoding sequence, inserted into UL18 and/or UL8 and at least one further nucleotide sequence or gene of interest, preferably another antigen encoding sequence, inserted into a at least one further insertion site, preferably UL56 (ORF1/3) and/or US4 (ORF70). In a specific aspect of said EHV vector of the present invention the at least two genes of interest are operably linked to regulatory sequences, preferably promoter sequences.

In another aspect of the vector of the present invention the EHV vector comprises two or more nucleotide sequences of interest, preferably genes of interest, more preferably antigen encoding sequences inserted into two or more insertion sites.

In another aspect of the vector of the present invention the EHV vector comprises an inactivation of UL18 and/or UL8 by inserting at least one nucleotide sequence of interest, preferably a gene of interest, more preferably an antigen encoding sequence inserted and at least one further nucleotide sequence of interest, preferably a gene of interest, more preferably an antigen encoding sequence (or an expression cassette comprising the same) and at least one further nucleotide sequence of interest, preferably a gene of interest, more preferably an antigen encoding sequence inserted into UL56 and/or US4.

In another aspect of the vector of the present invention the EHV vector comprises an inactivation of UL18 by inserting at least one nucleotide sequence of interest, preferably a gene of interest, more preferably an antigen encoding sequence inserted and at least one further nucleotide sequence of interest, preferably a gene of interest, more preferably an antigen encoding sequence (or an expression cassette comprising the same) and at least one further nucleotide sequence of interest, preferably a gene of interest, more preferably an antigen encoding sequence inserted into UL56.

In another aspect of the vector of the present invention the EHV vector comprises an inactivation of UL18 by inserting at least one nucleotide sequence of interest, preferably a gene of interest, more preferably an antigen encoding sequence inserted and at least one further nucleotide sequence of interest, preferably a gene of interest, more preferably an antigen encoding sequence (or an expression cassette comprising the same) and at least one further nucleotide sequence of interest, preferably a gene of interest, more preferably an antigen encoding sequence inserted into US4.

In another aspect of the vector of the present invention the EHV vector comprises an inactivation of UL18 by inserting at least one nucleotide sequence of interest, preferably a gene of interest, more preferably an antigen encoding sequence inserted and at least one further nucleotide sequence of interest, preferably a gene of interest, more preferably an antigen encoding sequence (or an expression cassette comprising the same) and at least one further nucleotide sequence of interest, preferably a gene of interest, more preferably an antigen encoding sequence inserted into UL56 and US4.

In another aspect of the vector of the present invention the EHV vector comprises an inactivation of UL8 by inserting at least one nucleotide sequence of interest, preferably a gene of interest, more preferably an antigen encoding sequence inserted and at least one further nucleotide sequence of interest, preferably a gene of interest, more preferably an antigen encoding sequence (or an expression cassette comprising the same) and at least one further nucleotide sequence of interest, preferably a gene of interest, more preferably an antigen encoding sequence inserted into UL56.

In another aspect of the vector of the present invention the EHV vector comprises an inactivation of UL8 by inserting at least one nucleotide sequence of interest, preferably a gene of interest, more preferably an antigen encoding sequence inserted and at least one further nucleotide sequence of interest, preferably a gene of interest, more preferably an antigen encoding sequence (or an expression cassette comprising the same) and at least one further nucleotide sequence of interest, preferably a gene of interest, more preferably an antigen encoding sequence inserted into US4.

In another aspect of the vector of the present invention the EHV vector comprises an inactivation of UL8 by inserting at least one nucleotide sequence of interest, preferably a gene of interest, more preferably an antigen encoding sequence inserted and at least one further nucleotide sequence of interest, preferably a gene of interest, more preferably an antigen encoding sequence (or an expression cassette comprising the same) and at least one further nucleotide sequence of interest, preferably a gene of interest, more preferably an antigen encoding sequence inserted into UL56 and US4.

In another aspect of the vector of the present invention the EHV vector comprises an inactivation of UL18 and UL8 by inserting at least one nucleotide sequence of interest, preferably a gene of interest, more preferably an antigen encoding sequence inserted and at least one further nucleotide sequence of interest, preferably a gene of interest, more preferably an antigen encoding sequence (or an expression cassette comprising the same) and at least one further nucleotide sequence of interest, preferably a gene of interest, more preferably an antigen encoding sequence inserted into UL56.

In another aspect of the vector of the present invention the EHV vector comprises an inactivation of UL18 and UL8 by inserting at least one nucleotide sequence of interest, preferably a gene of interest, more preferably an antigen encoding sequence inserted and at least one further nucleotide sequence of interest, preferably a gene of interest, more preferably an antigen encoding sequence (or an expression cassette comprising the same) and at least one further nucleotide sequence of interest, preferably a gene of interest, more preferably an antigen encoding sequence inserted into US4.

In another aspect of the vector of the present invention the EHV vector comprises an inactivation of UL18 and UL8 by inserting at least one nucleotide sequence of interest, preferably a gene of interest, more preferably an antigen encoding sequence inserted and at least one further nucleotide sequence of interest, preferably a gene of interest, more preferably an antigen encoding sequence (or an expression cassette comprising the same) and at least one further nucleotide sequence of interest, preferably a gene of interest, more preferably an antigen encoding sequence inserted into UL56 and US4.

US4 (ORF70)

In another aspect of the vector of the present invention the insertion into US4 is characterized by a partial deletion, truncation, substitution, modification or the like in US4, wherein US5 remains functional.

In another aspect of the vector of the present invention the insertion into US4 is characterized by the deletion of an approximately 801 bp portion within US4 for RacH (SEQ ID NO:24) or a 70%, 80%, 85%, 90%, 91%, 92%, 93%, 94%, 95%, 96%, 97%, 98%, 99% homologous and/or identical sequence thereof.

In a specific aspect of the vector of the present invention the insertion into US4 (ORF70) is characterized by a partial deletion, truncation, substitution, modification or the like in US4 (ORF70), whereby US5 (ORF71) remains functional.

In another aspect of the vector of the present invention the EHV vector comprises at least one flanking region selected from the group consisting of: SEQ ID NO:17, SEQ ID NO:18, SEQ ID NO:19, SEQ ID NO:20, SEQ ID NO:21, and SEQ ID NO:22 and a 70%, 80%, 85%, 90%, 91%, 92%, 93%, 94%, 95%, 96%, 97%, 98%, 99% homologous and/or identical sequence of any one of these sequences.

In another aspect of the vector of the present invention the EHV vector comprises (i) at least one left US4 flanking region selected from the group consisting of: SEQ ID NO:17, SEQ ID NO:19, and SEQ ID NO:21, and (ii) at least one right US4 flanking region selected from the group consisting of: SEQ ID NO:18, SEQ ID NO:20, and SEQ ID NO:22.

Nucleotide Sequences and Pathogens

In another aspect of the vector of the present invention said nucleotide sequence of interest is recombinant and/or heterologous and/or exogenous.

In another aspect of the vector of the present invention said antigen encoding sequence relates to a pathogen infecting a food producing animal such as swine, cattle or poultry or companion animals such as cat, Equine or dog.

In another aspect of the vector of the present invention the antigen encoding sequence is from a pathogen selected, but not limited to, from the list: Schmallenberg virus, Influenza A Virus, Porcine Respiratory and Reproductive Syndrome Virus, Porcine Circovirus, Classical Swine Fever Virus, African Swine Fever Virus, Hepatitis E Virus, Bovine Viral Diarrhea Virus, Rabies Virus, Feline Morbillivirus, *Clostridium tetani, Mycobacterium tuberculosis, Actinobacillus Pleuropneumoniae.*

In a specific aspect of the vector or the expression cassette of the present invention said antigen encoding sequence relates to a pathogen infecting swine. In a further specific aspect said pathogen is Swine Influenza A virus (IAV). In a further specific aspect said antigen is hemagglutinin (HA) antigen, especially said hemagglutinin antigen is derived from an Influenza A virus. For example the Influenza A virus is Influenza A virus (A/swine/Italy/116114/2010(H1N2)), Influenza A virus (A/swine/Italy/7680/2001(H3N2)), Influenza A virus (A/swine/Gent/132/2005(H1N1)), and/or Influenza A virus (A/swine/Italy/4675/2003(H1N2)). In a further specific aspect said antigen comprises or consists of a sequence encoded by the SEQ ID NO SEQ ID NO:14. In another specific aspect said antigen comprises or consists of a sequence encoding an amino acid sequence with at least 70%, at least 75%, at least 80%, at least 85%, at least 90%, least 91%, at least 92%, at least 93%, at least 94%, at least 95%, at least 96%, at least 97%, at least 98% or at least 99% identity to the amino acid sequence as set forth in SEQ ID NO:14.

Regulatory Sequences and Promoters

In another aspect of the vector of the present invention the gene of interest is operably linked to a regulatory sequence, preferably a promoter sequence.

In another aspect of the vector of the present invention the promoter sequence(s) operably linked to the sequence or gene of interest are selected from, but not limited to, the group consisting of: SV40 large T, HCMV and MCMV immediate early gene 1, human elongation factor alpha promoter, baculovirus polyhedrin promoter, a Polymerase II promoter, a functional fragment.

In another aspect of the vector of the present invention the promoter sequence operably linked to at least one gene of interest is MCMV or a functional fragment thereof or the complementary nucleotide sequences thereof.

In another aspect of the vector of the present invention the promoter sequence operably linked to at least one gene of interest is the endogenous promoter of UL8 or UL18.

In another aspect of the vector of the present invention the EHV vector is selected from the group consisting of EHV-1, EHV-3, EHV-4, EHV-8 and EHV-9.

In another aspect of the vector of the present invention the EHV vector is EHV-1, preferably RacH.

The present invention further concerns an EHV vector according to the present invention comprising:

a. a first nucleotide sequence of interest, preferably a gene of interest, such as an antigen encoding sequence, inserted into UL18 and/or UL8,
b. said first nucleotide sequence of interest is optionally operably linked with a regulatory nucleic acid sequence/promoter sequence,
c. said first nucleotide sequence of interest is optionally operably linked with a (further) regulatory nucleic acid, e.g. a polyadenylation sequence, preferably 71pA or BGHpA.

In a specific aspect the EHV vector further comprises a. second nucleotide sequence of interest, preferably a second gene of interest such as an antigen encoding sequence, into a second insertion site, preferably UL56 and/or US4,
b. said second nucleotide sequence of interest is optionally operably linked with a regulatory nucleic acid sequence/promoter sequence,
c. said second nucleotide sequence of interest is optionally operably linked with a regulatory nucleic acid, e.g. a polyadenylation sequence, preferably 71pA or BGHpA.

The present invention further concerns an EHV vector according to the present invention comprising:

a. an inactivated UL18 and/or UL8;
b. a first nucleotide sequence of interest, preferably a gene of interest, such as an antigen encoding sequence, inserted into UL56 and/or US4,
c. said first nucleotide sequence of interest is optionally operably linked with a regulatory nucleic acid sequence/promoter sequence,
d. said first nucleotide sequence of interest is optionally operably linked with a (further) regulatory nucleic acid, e.g. a polyadenylation sequence, preferably 71pA or BGHpA.

Host Cell

Further, the present invention provides a mammalian host cell characterized in that it comprises a replication deficient EHV vector as described herein.

The present invention also concerns a mammalian host cell characterized in that it comprises a vector according to the present invention.

The present invention further concerns a method of preparing a host cell, characterized by the following steps:

a. infecting the mammalian host cell according to the present invention with the vector according to the present invention,
b. cultivating the infected cells under suitable conditions,
c. optionally harvesting said host cell.

The invention further concerns the use of the vector according to the present invention or the mammalian host cell according to the present invention for the manufacture of an immunogenic composition or vaccine.

Complementing Cell Line

Further, the present invention provides a cell line expressing UL8 and/or UL18 of EHV or functional parts thereof for culturing the replication deficient EHV vector as described herein.

Furthermore, the present invention provides a cell line comprising a plasmid comprising an expression cassette comprising UL8 and/or UL18 of EHV or functional parts thereof, wherein the cell line is expressing UL8 and/or UL18 or functional parts thereof.

In another aspect of the cell line of the present invention the cell line is selected, but not limited to, from the group of: Vero cells, RK-13 (rabbit kidney), ST (Swine testicular), MDCK (Madin-Darby Canine Kidney), MDBK (Madin-Darby Bovine Kidney) and Equine dermal cells (NBL-6).

In another aspect of the cell line of the present invention the cell line is an ST cell line.

Method of Producing

Further, the present invention provides a method for producing a replication deficient Equid Alphaherpesvirus (EHV) comprising inactivating UL18 and/or UL8 as described herein.

Furthermore, the present invention provides a method for producing a replication deficient Equid Alphaherpesvirus (EHV) comprising the steps of:

a) providing a wild-type EHV or an attenuated EHV;
b) inactivating UL18 and/or UL8 of the EHV of step a) and selecting for EHV clones which are not carrying complete or functional part of UL18 and/or UL 8;
c) providing a complementing cell line expressing UL18 and/or UL8 or functional parts thereof;
d) obtaining the replication deficient Equid Alphaherpesvirus (EHV) by cultivating the EHV from step b) with the complementing cell line from step c).

The present invention further concerns a method of producing the vector according to the present invention comprising:

a. Inserting a first nucleotide sequence of interest, preferably a gene of interest, such as an antigen encoding sequence, into UL18 and/or UL8,
b. Optionally operably linking said first nucleotide sequence of interest with a regulatory nucleic acid sequence/promoter sequence,
c. Optionally operably linking said first nucleotide sequence of interest with a (further) regulatory nucleic acid, e.g. a polyadenylation sequence, preferably 71pA or BGHpA.

In a specific aspect the method further comprises a. Inserting a second nucleotide sequence of interest, preferably a second gene of interest, such as an antigen encoding sequence, into a second insertion site, preferably UL56 and/or US4, b. Optionally operably linking said second nucleotide sequence of interest with a regulatory nucleic acid sequence/promoter sequence, c. Optionally operably linking said second nucleotide sequence of interest with a regulatory nucleic acid, e.g. a polyadenylation sequence, preferably 71pA or BGHpA.

The present invention further concerns a method of producing the vector according to the present invention comprising:

a. inactivating UL18 and/or UL8 of the EHV;

b. Inserting a first nucleotide sequence of interest, preferably a gene of interest, such as an antigen encoding sequence, into UL56 and/or US4, c. Optionally operably linking said first nucleotide sequence of interest with a regulatory nucleic acid sequence/promoter sequence, d. Optionally operably linking said first nucleotide sequence of interest with a (further) regulatory nucleic acid, e.g. a polyadenylation sequence, preferably 71pA or BGHpA.

The invention further concerns a method for the preparation of an immunogenic composition or a vaccine for reducing the incidence or the severity of one or more clinical signs associated with or caused by an infection, comprising the following steps:

a. Infecting the complementing cell line according to the present invention with the vector according to the present invention, b. cultivating the infected cells under suitable conditions, c. collecting infected cell cultures, d. optionally purifying the collected infected cell cultures of step c)

e. optionally mixing said collected infected cell culture with a pharmaceutically acceptable carrier.

Vaccine

Further, the present invention provides an immunogenic composition comprising one or more EHV vectors as described herein.

In another aspect of the immunogenic composition of the present invention said immunogenic composition further comprises a pharmaceutically acceptable carrier.

In another aspect of the immunogenic composition of the present invention said immunogenic composition is a vaccine.

Thus, the invention further concerns an immunogenic composition comprising a. the vector according to the present invention, and/or b. a polypeptide expressed by the vector according to the present invention, such as a virus, a modified live virus, a virus like particle (VLP) or the like, and c. optionally a pharmaceutical- or veterinary-acceptable carrier or excipient, preferably said carrier is suitable for oral, intradermal, intramuscular or intranasal application, preferably said immunogenic composition comprises a virus. In a specific aspect said virus is an infectious virus.

The invention further concerns a vaccine or pharmaceutical composition comprising a. the vector according to the present invention, and/or b. a polypeptide expressed by the vector according to the present invention, such as a modified live virus, a virus like particle (VLP) or the like, and c. a pharmaceutical- or veterinary-acceptable carrier or excipient, preferably said carrier is suitable for oral, intradermal, intramuscular or intranasal application, d. optionally said vaccine further comprises an adjuvant.

Method of Treatment and Uses

Further, the present invention provides a method for immunizing a subject comprising administering to such subject an immunogenic composition as described herein.

Furthermore, the present invention provides a method of treating or preventing clinical signs caused by a pathogen in a subject of need, the method comprising administering to the subject a therapeutically effective amount of an immunogenic composition as described herein.

The present invention provides the immunogenic composition as described herein for use in a method for immunizing a subject comprising administering said immunogenic composition to such subject.

The present invention provides the immunogenic composition as described herein for use in a method of treating or preventing clinical signs caused by a pathogen in a subject of need, the method comprising administering to the subject a therapeutically effective amount of said immunogenic composition.

In another aspect of the method or use of the present invention said subject is selected from the list consisting of swine, cattle, poultry, cat, equine and dog.

In another aspect of the method or use of the present invention the immunogenic composition is administered once.

In another aspect of the method or use of the present invention the immunogenic composition is administered at two or more doses.

The invention also concerns a kit for vaccinating an animal, preferably a food producing animal such as swine or cattle or a companion animals such as cat, Equine or dog, against a disease associated with and/or reducing the incidence or the severity of one or more clinical signs associated with or caused by a pathogen in an animal comprising:

a) a dispenser capable of administering a vaccine to said animal; and b) the immunogenic composition or the vaccine according to the present invention, and c) optionally an instruction leaflet.

The present invention further concerns a kit consisting of a vector according to the present invention, optionally transfection reagent(s), and an instruction leavelet.

Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

The practice of the present invention will employ, unless otherwise indicated, conventional techniques of virology, molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

Molecular Biology Definitions

The term "vector" as it is known in the art refers to a polynucleotide construct, typically a plasmid or a bacterial artificial chromosome, used to transmit genetic material to a host cell. Vectors can be, for example, bacteria, viruses, phages, bacterial artificial chromosomes, cosmids, or plasmids. A vector as used herein can be composed of or contain either DNA or RNA. In some embodiments, a vector is composed of DNA. In some embodiments a vector is an infectious virus. Such a viral vector contains a viral genome which was manipulated in a way that it carries a foreign gene which has no function in the replication of the viral vector neither in cell culture nor in a host animal. According to specific aspects of the present disclosure a vector may be used for various aspects such as mere transmission of genetic material, for the transfection of host cells or organisms, for use as vaccines, e.g. DNA vaccines or for gene expression purposes. Gene expression is a term describing the biosynthesis of a protein in a cell as directed by a specific polynucleotide sequence called gene. In a specific aspect a vector may be an "expression vector", which is a vector that is capable of directing the expression of a protein encoded by one or more genes carried by the vector when it is present in the appropriate environment.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018; Paoletti, "Applications of pox virus vectors to vaccination: An update, "PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector, "Molecular and Cellular Biology March 1984, Vol. 4, No. 3, p. 406; EPA0 370 573; U.S. application Ser. No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589, 466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbachet al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

The term "viral vector" describes a genetically modified virus which was manipulated by recombinant DNA technique in a way so that its entry into a host cell results in a specific biological activity, e.g. the expression of a transgene carried by the vector. In a specific aspect the transgene is an antigen. A viral vector may or may not be replication competent in the target cell, tissue, or organism.

Generation of a viral vector can be accomplished using any suitable genetic engineering techniques well known in the art, including, without limitation, the standard techniques of restriction endonuclease digestion, ligation, transformation, plasmid purification, DNA sequencing, transfection in cell cultures, for example as described in Sambrook et al. (Molecular Cloning: A Laboratory Manual. Cold Spring Harbor Laboratory Press, N.Y. (1989)) or K. Maramorosch and H. Koprowski (Methods in Virology Volume VIII, Academic Press Inc. London, UK (2014)).

A viral vector can incorporate sequences from the genome of any known organism. The sequences can be incorporated in their native form or can be modified in any way to obtain a desired activity. For example, the sequences can comprise insertions, deletions or substitutions.

A viral vector can include coding regions for two or more proteins of interest. For example, the viral vector can include the coding region for a first protein of interest and the coding region for a second protein of interest. The first protein of interest and the second protein of interest can be the same or different. In some embodiments, the viral vector can include the coding region(s) for a third or a fourth protein of interest. The third and the fourth protein of interest can be the same or different. The total length of the two or more proteins of interest encoded by one viral vector can vary. For example, the total length of the two or more proteins can be at least about 200 amino acids. At least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer.

Preferred viral vectors include herpes virus vectors such as derived from EHV-1 or EHV-4 or other varicelloviruses like PrV (Pseudorabies virus) or BHV-1 (Bovine Herpesvirus 1).

According to specific aspects of the present disclosure, the term "viral vector" or alternatively "viral construct" refers to a recombinant viral construct derived from a virus, which is selected from the families of Herpesviridae such as EHV-1, EHV-4. Preferred viral vectors include herpes virus vectors such as derived from EHV-1 or EHV-4

The terms "viral vector" and "viral construct" can be used interchangeably.

The term "construct," as used herein, refers to a recombinant nucleic acid such as a plasmid, a BAC, or a recombinant virus that has been artificially generated.

The term "plasmid" refers to cytoplasmic DNA that replicates independently of the bacterial chromosome within a bacterial host cell. In a specific aspect of the present invention the term "plasmid" and/or "transfer plasmid" refers to an element of recombinant DNA technology useful for construction of e.g. an expression cassette for insertion into a viral vector. In another specific aspect the term "plasmid" may be used to specify a plasmid useful for DNA vaccination purposes.

As used herein, the terms "nucleic acid" and "polynucleotide" are interchangeable and refer to any nucleic acid.

The term "nucleic acid", "nucleic acid sequence", "nucleotide sequence", "polynucleotide", "polynucleotide sequence", "RNA sequence" or "DNA sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The nucleic acid sequences of the present invention can be prepared using standard techniques well known to one of skill in the art.

The terms "nucleic acid" and "polynucleotide" also specifically include nucleic acids composed of bases other than the five biologically occurring bases (adenine, guanine, thymine, cytosine and uracil).

The terms "regulatory nucleic acid", "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, promoter sequences, core elements required for basic interaction of RNA polymerase and transcription factors, upstream elements, enhancers, and response elements. Exemplary regulatory elements in prokaryotes include promoters, operator sequences and ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry sites (IRES), picornaviridal 2A sequences, and the like, that provide for and/or regulate expression of a coding sequence and/or production of an encoded polypeptide in a host cell.

An "internal ribosome entry site" or "IRES" describes a sequence which functionally promotes translation initiation independent from the gene 5' of the IRES and allows two cistrons (open reading frames) to be translated from a single transcript in an animal cell. The IRES provides an independent ribosome entry site for translation of the open reading frame immediately downstream of it. Unlike bacterial mRNA which can be polycistronic, i.e., encode several different polypeptides that are translated sequentially from the mRNAs, most mRNAs of animal cells are monocistronic and code for the synthesis of only one polypeptide. With a polycistronic transcript in a eukaryotic cell, translation would initiate from the 5' most translation initiation site, terminate at the first stop codon, and the transcript would be released from the ribosome, resulting in the translation of only the first encoded polypeptide in the mRNA. In a eukaryotic cell, a polycistronic transcript having an IRES operably linked to the second or subsequent open reading frame in the transcript allows the sequential translation of that downstream open reading frame to produce the two or more polypeptides encoded by the same transcript. The IRES can be of varying length and from various sources, e.g. Encephalomyocarditis virus (EMCV), picornaviruses (e.g. Foot-and-mouth disease virus, FMDV or Polio virus (PV), or Hepatitis C virus (HCV). Various IRES sequences and their use in vector construction have been described and are well known in the art. The downstream coding sequence is operably linked to the 3' end of the IRES at any distance that will not negatively affect the expression of the downstream gene. The optimum or permissible distance between the IRES and the start of the downstream gene can be readily determined by varying the distance and measuring expression as a function of the distance.

The term "2a" or "2a peptide" means short oligopeptide sequences, described as 2a and '2a-like', that serve as linkers which are able to mediate a co-translational cleavage between proteins by a process defined as ribosomal-skipping. Such 2a and '2a-like' sequences (from Picornaviridae and other viruses or cellular sequences) can be used to concatenate multiple gene sequences into a single gene, ensuring their co-expression within the same cell (see Luke and Ryan, 2013).

As used herein, the term "promoter" or "promoter sequence" means a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and animals such as mammals (including horses, pigs, cattle and humans), birds or insects. A promoter can be inducible, repressible, and/or constitutive.

Inducible promoters initiate increased levels of transcription from DNA under their control in response to some change in culture conditions, such as a change in temperature (Ptashne, 2014). Examples of promoters well known to the person skilled in the art are for example SV40 large T, HCMV and MCMV immediate early gene 1, human elongation factor alpha promoter, baculovirus polyhedrin promoter, Polymerase II promoter.

The term "enhancer" denotes a polynucleotide sequence which in the cis location acts on the activity of a promoter and thus stimulates the transcription of a gene or coding sequence functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

The term "complementary nucleotide sequences" describes one strand of the two paired strands of polynucleotides such as DNA or RNA. The nucleotide sequence of the complementary strand mirrors the nucleotide sequence of its paired strand so that for each adenosin it contains a thymin (or uracil for RNA), for each guanine a cytosin, and vice versa. The complementary nucleotide sequence of e.g. 5'-GCATAC-3' is 3'-CGTATG-5' or for RNA 3'-CGUAUG-5'.

The terms "gene", "gene of interest", as used herein have the same meaning and refer to a polynucleotide sequence of any length that encodes a product of interest. The gene may further comprise regulatory sequences preceding (5' non-coding or untranslated sequences) and following (3' non-coding or untranslated sequences) the coding sequence. The selected sequence can be full length or truncated, a fusion or tagged gene, and can be a cDNA, a genomic DNA, or a DNA fragment. It is generally understood that genomic DNA encoding for a polypeptide or RNA may include non-coding regions (i.e. introns) that are spliced from mature messenger RNA (mRNA) and are therefore not present in cDNA encoding for the same polypeptide or RNA. It can be the native sequence, i.e. naturally occurring form(s), or can be mutated, or comprising sequences derived from different sources or otherwise modified as desired. These modifications include codon optimizations to optimize codon usage in the selected host cell or tagging. Furthermore they can include removal or additions of cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples. The selected sequence can encode a secreted, cytoplasmic, nuclear, membrane bound or cell surface polypeptide.

The term "nucleotide sequence of interest" as used herein is a more general term than gene of interest as it does not necessarily comprise a gene but may comprise elements or parts of a gene or other genetic information, e.g. ori (origin of replication). A nucleotide sequence of interest may be any DNA or RNA sequence independently of whether it comprises a coding sequence or not.

"Open reading frame" or "ORF" refers to a length of nucleic acid sequence, either DNA or RNA, that comprises a translation start signal or initiation codon, such as an ATG or AUG, and a termination codon and can be potentially translated into a polypeptide sequence.

The term "UL (unique long)" is an abbreviation to describe the unique long segment of the EHV genome, preferably the EHV-1 genome.

The term "US (unique short)" is an abbreviation to describe the unique short segment of the EHV-1 genome, preferably the EHV-1 genome.

The term "transcription" describes the biosynthesis of mRNA in a cell.

The term "expression" as used herein refers to transcription and/or translation of a nucleic acid sequence within a host cell. According to specific aspects of the present invention the term "expression" refers to transcription and/or translation of a heterologous and/or exogenous nucleic acid sequence within a host cell. The level of expression of a desired product in a host cell may be determined on the basis of either the amount of corresponding RNA or mRNA that is present in the cell, or the amount of the desired polypeptide encoded by the selected sequence. For example, mRNA transcribed from a selected sequence can be quantitated by Northern blot hybridization, ribonuclease RNA protection, in situ hybridization to cellular RNA or by RTqPCR (reverse transcription followed by quantitative PCR). Proteins expressed from a selected sequence can be quantitated by various methods, e.g. by ELISA, by Western blotting, by radioimmunoassays, by immunoprecipitation, by assaying for the biological activity of the protein, or by immunostaining of the protein followed by FACS analysis.

The term "expression cassette" or "transcription unit" or "expression unit" defines a region within a vector, construct or polynucleotide sequence that contains one or more genes to be transcribed, wherein the nucleotide sequences encoding the transcribed gene(s) as well as the polynucleotide sequences containing the regulatory elements contained within an expression cassette are operably linked to each other. They are transcribed from a promoter and transcription is terminated by at least one polyadenylation signal. In one specific aspect, they are transcribed from one single promoter. As a result, the different genes are at least transcriptionally linked. More than one protein or product can be transcribed and expressed from each transcription unit (multicistronic transcription unit). Each transcription unit will comprise the regulatory elements necessary for the transcription and translation of any of the selected sequences that are contained within the unit. And each transcription unit may contain the same or different regulatory elements. For example, each transcription unit may contain the same terminator, IRES element or introns may be used for the functional linking of the genes within a transcription unit. A vector or polynucleotide sequence may contain more than one transcription unit.

By the term "increased expression", "increased titer or productivity" or "improved expression or productivity" is meant the increase in expression, synthesis or secretion of a heterologous and/or exogenous sequence introduced into a host cell, for example of a gene coding for a therapeutic protein, by comparison with a suitable control, for example a protein encoded by a cDNA versus a protein encoded by an intron-containing gene. There is increased titer or productivity if a cell according to the invention is cultivated according to a method according to the invention described here, and if this cell has at least a 1.2-fold, a 1.5-fold, a two-fold, a three-fold, a four-fold or a five-fold increase in specific productivity or titer. There is also increased titer or productivity if a cell according to the invention is cultivated according to a method according to the invention described here, and if this cell has at least a 1.2-fold or at least a 1.5-fold or at least a two-fold or at least a three-fold increase in specific productivity or titer. There is also in particular increased titer or productivity if a cell according to the invention is cultivated according to a method according to the invention described here, and if this cell has at least a 1.2-fold to five-fold, preferably a 1.5-fold to five-fold, more preferably two-fold to five-fold particularly preferably a three-fold to five-fold increase in specific productivity or titer. “Increased expression” may mean as well that more cells are actually expressing the gene/sequence of interest. For example increased expression may mean that the new promoters of the present invention are active for a longer period of time during the viral replication cycle relative to other promoters.

An increased expression, titer or productivity may be obtained by using a heterologous vector according to the invention. This may be combined with other approaches such as a FACS-assisted selection of recombinant host cells which contain, as additional selectable marker, one or more fluorescent proteins (e.g. GFP) or a cell surface marker. Other methods of obtaining increased expression, and a combination of different methods may also be used, are based for example on the use of cis-active elements for manipulating the chromatin structure (e.g. LCR, UCOE, EASE, isolators, S/MARs, STAR elements), on the use of (artificial) transcription factors, treatment of the cells with natural or synthetic agents for up-regulating endogenous or heterologous and/or exogenous gene expression, improving the stability (half-life) of mRNA or the protein, improving the initiation of mRNA translation, increasing the gene dose by the use of episomal plasmids (based on the use of viral sequences as replication origins, e.g. SV40, polyoma, adenovirus, EBV or BPV), the use of amplification-promoting sequences or in vitro amplification systems based on DNA concatemers.

The term “obtained” may comprise an isolation and/or purification step known to the person skilled in the art, preferably using precipitation, columns ect.

An assay to measure “increased expression” is LC-MS/MS-based protein measurements such as multiple reaction monitoring (MRM); antibody-based detection methods such as Western blot, dot blot, or Immunodiffusion, and flow cytometry; and measures of biological activity by hemagglutination assay.

“Promoter activity” is measured indirectly by quantification of mRNA transcribed under control of the respective promoter. mRNA is quantified by RTqPCR relative to an endogenous standard.

The term “viral titre” is a measure of infectious units per volume of a virus preparation. Viral titre is an endpoint in a biological procedure and is defined as the dilution at which a certain proportion of tests carried out in parallel show an effect (Reed and Muench, 1938). Specifically the tissue culture infectious dose fifty per milliliter (TCID50/ml) gives the dilution of a virus preparation at which 50% of a number of cell cultures inoculated in parallel with that dilution are infected.

“Transcription-regulatory elements” normally comprise a promoter upstream of the gene sequence to be expressed, transcription initiation and termination sites and a polyadenylation signal.

The term “transcription initiation site” refers to a nucleic acid in the construct corresponding to the first nucleic acid incorporated into the primary transcript, i.e. the mRNA precursor. The transcription initiation site may overlap with the promoter sequences.

The “termination signal” or “terminator” or “polyadenylation signal” or “polyA” or transcription termination site” or “transcription termination element” is a signal sequence which causes cleavage at a specific site at the 3' end of the eukaryotic mRNA and post-transcriptional incorporation of a sequence of about 100-200 adenine nucleotides (polyA tail) at the cleaved 3' end, and thus causes RNA polymerase to terminate transcription. The polyadenylation signal comprises the sequence AATAAA about 10-30 nucleotides upstream of the cleavage site and a sequence located downstream. Various polyadenylation elements are known such as tk polyA, SV40 late and early polyA, BGH polyA (described for example in U.S. Pat. No. 5,122,458) or hamster growth hormone polyA (WO02010010107).

“Translation regulatory elements” comprise a translation initiation site (AUG), a stop codon and a polyA signal for each individual polypeptide to be expressed. An internal ribosome entry site (IRES) may be included in some constructs. In order to optimize expression it may be advisable to remove, add or alter 5'- and/or 3'-untranslated regions of the nucleic acid sequence to be expressed to eliminate any potentially extra inappropriate alternative translation initiation codons or other sequences that may interfere with or reduce expression, either at the level of transcription or translation. Consensus ribosome binding sites (Kozak sequence) can be inserted immediately upstream of the start codon to enhance translation and thus expression. Increased A/U contents around this ribosome binding site further a more efficient ribosome binding.

By definition, every polynucleotide sequence or every gene inserted in a host cell and the respective protein or RNA encoded thereby is referred to as “exogenous”, “exogenous sequence”, “exogenous gene”, “exogenous coding sequence”, with respect to the host cell, when it comes from a different (virus) species. Accordingly, an EHV-4 based promoter is exogenous in view of an EHV-1 viral vector. As used herein in respect to a sequence or gene of interest such as an antigen the term “exogenous” means that said sequence or gene of interest, specifically said antigen is expressed out of its natural species context. Accordingly, the HA antigen from swine IAV is one example of an exogenous antigen in respect to the EHV-1 vector. Any sequence derived from a different pathogen than EHV-1 is therefore an exogenous sequence or gene of interest or antigen according to a specific aspect of the present invention.

By definition, every polynucleotide sequence or every gene inserted in a host cell and the respective protein or RNA encoded thereby is referred to as “heterologous, “heterologous sequence”, “heterologous gene”, “heterologous coding sequence”, “transgene” or “heterologous protein” with respect to the host cell. This applies even if the sequence to be introduced or the gene to be introduced is identical to an endogenous sequence or an endogenous gene of the host cell. For example, an EHV-4 promoter sequence introduced into an EHV-4 viral vector at a different site or in modified form than in the EHV-4 wild type virus is by definition a heterologous sequence. As used herein in respect to a sequence or gene of interest such as an antigen, the term "heterologous" means that said sequence or gene of interest, specifically said antigen, is expressed out of its natural subspecies context. Accordingly, any non-EHV-1 specific sequence or gene of interest such as an antigen, for example an antigen from any Equid alphaherpesvirus except EHV-1, e.g. EHV-3, EHV-8, is therefore a heterologous sequence or gene of interest or antigen according to a specific aspect of the present invention.

The term "non-naturally occurring" means any sequence or gene of interest such as an antigen, which is not occurring in this context naturally, such as a hybrid sequence or a sequence or gene of interest such as an antigen from a different species, or sequence or gene of interest such as an antigen, which is not a product of nature due to artificial mutation, insertion, deletion or the like.

The term "recombinant" is used exchangeably with the terms "non-naturally occurring", "heterologous" and "exogenous" throughout the specification of this present invention. Thus, a "recombinant" protein is a protein expressed from a either a heterologous or an exogenous polynucleotide sequence. The term recombinant as used with respect to a virus, means a virus produced by artificial manipulation of the viral genome. A virus comprising a heterologous or an exogenous sequence such as an exogenous antigen encoding sequence is a recombinant virus. The term recombinant virus and the term non-naturally occurring virus are used interchangeably.

Thus, the term "heterologous vector" means a vector that comprises a heterologous or an exogenous polynucleotide sequence. The term "recombinant vector" means a vector that comprises a heterologous or a recombinant polynucleotide sequence.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

Furthermore, within the scope of the present description the terms "functional linking", "functionally linked" or "operably linked" means that two or more nucleic acid sequences or sequence elements are positioned in a way that permits them to function in their intended manner. For example, a promoter/enhancer or terminator is functionally linked to a coding gene sequence if it is able to control or modulate the transcription of the linked gene sequence in the cis position. Generally, but not necessarily, the DNA sequences that are functionally linked are contiguous and, where necessary to join two polypeptide coding regions or in the case of a secretion signal peptide, contiguous and in reading frame. However, although an operably linked promoter is generally located upstream or an operably linked terminator is generally located downstream of the coding sequence, it is not necessarily contiguous with it. Enhancers do not have to be contiguous as long as they increase the transcription of the coding sequence. For this they can be located upstream or downstream of the coding sequence and even at some distance. A polyadenylation site is operably linked to a coding sequence if it is located at the 3 ' end of the coding sequence in a way that transcription proceeds through the coding sequence into the polyadenylation signal. Linking is accomplished by recombinant methods known in the art, e.g. by ligation at suitable restriction sites or blunt ends or by using fusion PCR methodology. Synthetic oligonucleotide linkers or adapters can be used in accord with conventional practice if suitable restriction sites are not present.

Accordingly, the term "functional fragment" or "functional derivative" of a promoter sequence means that the fragment or derivative still effects promoter activity. Functional assays of how to assess promoter activity are well known to one of ordinary skill in the art (Bustin 2000, Nolan et al. 2006). An exemplary embodiment of such a functional assay includes e.g. a promoter kinetics experiment. Cells infected with vector viruses carrying expression cassettes where a promoter or fragment thereof directs transcription of a reporter transgene are incubated for different times. Total RNA is prepared from samples collected at different times after infection. After destruction of contaminating DNA by DNAse I digestion, the RNA is reverse transcribed. One replicate sample is processed with addition of reverse transcriptase (RT), the second replicate is processed without addition of RT in order to demonstrate successful removal of contaminating DNA from the RNA preparation. The resulting cDNA is purified and used as template in a conventional PCR. Only the samples processed with the addition of RT shall produce a PCR product. These cDNAs can then be used for qPCR with primers for the reporter transgene and in parallel with primers for an essential gene of the viral vector (internal standard gene), the transcription of which provides an internal standard for the efficiency of infection and replication. qPCR values of the reporter are normalized between the different constructs and times after infection using the qPCR values of the internal standard gene. This allows an interpretation of promoter activities of different promoters and fragments thereof.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology.

In other words, to obtain a comparable polypeptide or polynucleotide having 95% sequence homology with a reference sequence, 85%, preferably 90%, 91%, 92%, 93%, 94%, even more preferably 95%, 96%, 97%, 98%, 99%, 99.9% of the amino acid residues or nucleotides in the reference sequence must match or comprise a conservative substitution with another amino acid or nucleotide. Alternatively, a number of amino acids or nucleotides up to 15%, preferably up to 10%, 9%, 8%, 7%, 6%, even more preferably up to 5%, 4%, 3%, 2%, 1%, 0.1% of the total amino acid residues or nucleotides, not including conservative substitutions, in the reference sequence may be inserted into the reference sequence. Preferably the homolog sequence comprises at least a stretch of 50, even more preferred of 100, even more preferred of 250, even more preferred of 500 nucleotides.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, MD 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, 91%, 92%, 93%, 94%, even more preferably 95%, 96%, 97%, 98%, 99%, 99.9% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, 91%, 92%, 93%, 94%, even more preferably 95%, 96%, 97%, 98%, 99%, 99.9% identity relative to the reference nucleotide sequence, up to 15%, preferably 10%, 9%, 8%, 7%, 6%, even more preferably 5%, 4%, 3%, 2%, 1%, 0.1% of the nucleotides in the reference sequence may be deleted or substituted with another nucleotide, or a number of nucleotides up to 15%, preferably 10%, 9%, 8%, 7%, 6%, even more preferably 5%, 4%, 3%, 2%, 1%, 0.1% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, 91%, 92%, 93%, 94%, even more preferably 95%, 96%, 97%, 98%, 99% sequence identity to a reference amino acid sequence, it is intended that the given amino acid sequence of the polypeptide is identical to the reference sequence except that the given polypeptide sequence may include up to 15, preferably up to 10, 9, 8, 7, 6, even more preferably up to 5, 4, 3, 2, 1 amino acid alterations per each 100 amino acids of the reference amino acid sequence. In other words, to obtain a given polypeptide sequence having at least 85%, preferably 90%, 91%, 92%, 93%, 94%, even more preferably 95%, 96%, 97%, 98%, 99% sequence identity with a reference amino acid sequence, up to 15%, preferably up to 10%, 9%, 8%, 7%, even more preferably up to 5%, 4%, 3%, 2%, 1% of the amino acid residues in the reference sequence may be deleted or substituted with another amino acid, or a number of amino acids up to 15%, preferably up to 10%, 9%, 8%, 7%, even more preferably up to 5%, 4%, 3%, 2%, 1% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "sequence identity" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package, using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information.

EHV-1 and EHV-4/Recombinant Vector Technology Definitions

The term "equid" or "equine" or "equin" means of or belonging to the family Equidae, which includes the horses, asses, and zebras, preferably horses. In addition, the term "equid" or "equine" or "equin" encompasses also hybrids of members of the family Equidae (e.g. mules, hinnies, etc.).

A "Herpes virus" or "Herpes virus vector" refers to a species in the family Herpesviridae in the order Herpesvirales.

The term "Equid herpes virus vector" or "Equid herpes virus" or "EHV" means a member of the family Herpesviridae affecting horses. To date eight different species of equid herpesviruses have been identified, five belonging to the subfamily Alphaherpesvirinae (EHV-1, EHV-3, EHV-4, EHV-8 and EHV-9) and three to the Gammaherpesvirinae. (Virus Taxonomy: 2015 Release EC 47, London, UK, July 2015; Email ratification 2016 (MSL #30)).

The term "EHV-1" means Equid Alphaherpesvirus 1, a member of the subgenus *Varicellovirus* in the genus *Alphaherpesvirinae* in the family Herpesviridae. A non-limiting reference sequence for EHV-1 would be for example the wild-type EHV-1 strain ab4 (Genbank accession number AY665713.1) or the RacH (Hübert 1996).

The term EHV-4 means Equid Alphaherpesvirus 4, a member of the subgenus *Varicellovirus* in the genus *Alphaherpesvirinae* in the family Herpesviridae.

The term "inserted into UL18" or "inserted into ORF43" means that a DNA fragment was inserted into the genomic DNA at a location encoding the Equid Alphaherpesvirus 1 open reading frame 43 (UL18). In a specific aspect of the present invention the insertion referred to resulted in a complete deletion (945 bp) of ORF43 (UL18).

The term "inserted into UL8" or "inserted into ORF54" means that a DNA fragment was inserted into the genomic DNA at a location encoding the Equid Alphaherpesvirus 1 open reading frame 54 (UL8). In a specific aspect of the present invention the insertion referred to resulted in a deletion of (2256 bp) of ORF 54 (UL8).

The term "inserted into ORF70" or "inserted into US4" means that a DNA fragment was inserted into the genomic DNA at a location encoding the Equid Alphaherpesvirus 1 open reading frame 70 (US4). In a specific aspect of the present invention the insertion referred to resulted in a deletion of the 801 5' basepairs of ORF70 (US4) leaving the remaining 423 bp of the 3' end intact but abolishing expression of the orf70 (US4) gene product glycoprotein G. The glycoprotein G of several Alphaherpesviruses including EHV-1 was shown to be secreted from infected cells and function as an immunomodulatory protein by binding pro-inflammatory cytokines. Abolishment of its expression in the viral vector should increase the immunogenicity of the viral infection as compared to a wild-type EHV-1 with intact glycoprotein G expression.

The term "inserted into ORF1/3" or "inserted into UL56" means that a DNA fragment was inserted in the viral genome at a position where by accidental deletion over passaging during the attenuation procedure of the vaccine strain EHV-1 RacH a 1283 bp fragment comprising 90% of ORF1 and the entire ORF2 were lost. This insertion site was chosen because the likelyhood that expression of a transgene from this location would interfere with viral replication was expected to be extremely low.

The term "inactivation" refers to a mutation within the UL8 (ORF54) and/or UL18 (ORF43). The term mutation comprises modifications in the viral DNA encoding said proteins leading to an alteration of said encoded protein. The term mutation relates to, but is not limited to, substitutions (replacement of one or several nucleotides/base pairs), deletions (removal of one, several or all nucleotides/base pairs), and/or insertions (addition of one or several nucleotides/base pairs). Thus, the term mutation comprises mutations including, but not limited to point mutations (single nucleotide mutations) or larger mutations wherein e.g. parts of the encoding (and/or non-encoding) nucleotides/base pairs are deleted (partial deletion) or all the encoding (and/or non-encoding) nucleotides/base pairs are deleted (complete deletion), substituted and/or additional coding (and/or non-encoding) nucleotides/base pairs are inserted. It is to be understood that the term mutation comprises mutations within the coding nucleotides/base pairs, mutations within the non-encoding nucleotides/base pairs such as within the regulatory nucleotides/base pairs and mutations within both the encoding nucleotides/base pairs and non-encoding nucleotides/base pairs. Further, the term mutation also comprises the inversion of nucleotides/base pairs (encoding and/or non-encoding) such as inversion of a part or all encoding nucleotides/base pairs or inversion of a part or all non-encoding nucleotides/base pairs or a combination thereof. Furthermore, the term mutation also comprises the relocation of nucleotides/base pairs (encoding and/or non-encoding) such as relocation of a part or all encoding nucleotides/base pairs or relocation of a part or all non-encoding nucleotides/base pairs or a combination thereof. As used herein, mutation may be a single mutation or several mutations, therefore, often the term "mutation(s)" used and relates to both a single mutation and several mutations. Said mutations may result in a modified expressed protein due to the change in the coding sequence. However, the term mutation is well known to the person skilled in the art and the person skilled in the art can generate mutations without further ado.

Further, the term "inactivation" encompasses a reduced (or eliminated) expression of UL18 and/or UL8 RNA and/or protein. It is to be understood that reduced expression encompasses both reduced RNA transcription as well as reduced protein expression. Preferably, the expression of UL18 and/or UL8 RNA and/or protein is reduced by 5-10%, 10-20%, 20-30%, 30-40%, 40-50%, 50-60%, 60-70%, 70-80%, 80-90%, 90-95%, 95-99% or more by RNA and/or protein when compared to the expression of a wildtype EHV virus or the EHV virus of the present invention cultured in a complementing cell line. More preferably, the expression of UL18 and/or UL8 RNA and/or protein is reduced by 50-100%, 60-100%, 70-100% 80-100% or 90-100% by RNA and/or protein when compared to the expression of a wildtype EHV virus or the EHV virus of the present invention cultured in a complementing cell line. Even more preferably, the expression of UL18 and/or UL8 RNA and/or protein is reduced in the EHV of the present invention 80%, 81%, 82%, 83%, 84%, 85%, 86%, 87%, 88%, 89%, 90%, 91%, 92%, 93%, 94%, 95%, 96%, 97%, 98%, 99% or 100% by RNA and/or protein when compared to the expression of a wildtype EHV virus or the EHV virus of the present invention cultured in a complementing cell line.

The term "complete or partially deleted, substituted or inverted" encompasses a complete or partial deletion, a complete or partial substitution and a complete or partial inversion. The term "complete" means that the whole ORF (UL) is affected from the start codon to the stop of the ORF (UL). Preferably, the UL18 and/or UL8 is complete deleted, substituted or inverted. However, the term "partial" means that only a part of the whole ORF (UL) is affected. Preferably, UL18 and/or UL8 is partially deleted, substituted or inverted.

The term "from the 5'-Terminus of the start codon" refers to the deletion, substitution or inversion of the ORF (UL) at the 5'-Terminus. The term as used herein is to be understood that said deletion, substitution or inversion affects (includes) the start codon of the ORF. Thus, portions of the 3'-Terminus of the ORF are retained whereas portions of the 5'-Terminus region of the ORF are deleted. However, said deletion, substitution or inversion from the 5'-Terminus may result in the deletion of one or more amino acids within the corresponding protein or in a frameshift in the ORF which results in a coding region which is different from the protein of the wildtype. However, said deletion, substitution or inversion at the 5'-Terminus may result in the expression of no protein at all as the start codon is truncated.

The term "from the A, T or G of the start codon" as used herein is to be understood that said deletion, substitution or inversion may start with the A or T or G. In case the deletion starts with the A, the A is deleted. However, if the deletion from the A comprises the deletion of two or more nucleotides, the T is deleted as well. Further, if the deletion from the A comprises the deletion of three or more nucleotides the A, T, and G is deleted. However, it is to be understood that if the deletion starts with the T, the T is deleted, whereas the A of ATG still remains. Further, if the deletion starts with the G, the G is deleted, whereas the A and T of ATG still remain.

The term "within UL18" or "within UL8" as used herein is to be understood that said deletion, substitution or inversion of nucleotides may occur everywhere within said ORF (UL). Thus, said deletion, substitution or inversion of nucleotides may affect only the 5'-Terminus of UL8 (ORF54) and/or UL18 (ORF43), only the 3'-Terminus of UL8 (ORF54) and/or UL18 (ORF43) or the rest of the nucleotides of said ORF (UL) or any combinations thereof.

The term "replication defective" is well known to the person skilled in the art. In general, the term means that the virus has a reduced replication in the host (such as a mammalian cell or cell line). Preferably, the replication is reduced by at least 90%, preferably 95%, preferably 97.5%, even more preferably 99.5%, even more preferably 99.75% and most preferably by 100%. In case the replication is reduced by 100% the replication is completely abolished. Preferably, the replication is compared to a non-replication defective virus of the same species. Preferably, the replication is compared to the replication of the replication defective virus cultured in complementing cells or cell lines. Preferably, the replication defective EHV of the present invention is still infective and replicate, but can only be packaged as replication-competent virus in complementing cells or cell lines. Preferably, virus DNA and virus protein are still produced in the host and, thus, the replication defective EHV of the present invention still induces an immune response and/or protective immunity.

The term "complementing cell line" or "complementing cell" is well known to the person skilled in the art. In the context of the present invention a complementing cell line is a cell line in which the cells are expressing UL8 and/or UL18 (or functional parts thereof) of EHV (preferably EHV-1). As the replication defective EHV vector comprises an inactivation of UL8 and/or UL18 the replication defective EHV is not replication in a host cell (such as a mammalian cell or cell line), but in the corresponding complementing cell line expressing UL8 and/or UL18.

The term "$TCID_{50}$" is well known to the person skilled in the art. In general, this endpoint dilution assay quantifies the amount of virus required to kill 50% of infected hosts or to produce a cytopathic effect in 50% of inoculated tissue culture cells. Assays for measuring $TCID_{50}$ are well known to the person skilled in the art such as the Spearman-Karber or Reed-Muench method (Reed and Muench, 1938).

The term "infective" means the introduction of a virus into a host or a host cell.

Vaccine Definitions

An "immunogenic or immunological composition" refers to a composition of matter that comprises at least one antigen, or immunogenic portion thereof, that elicits an immunological response in the host of a cellular or antibody-mediated immune response to the composition.

The term "antigen" used herein is well understood in the art and includes substances which are immunogenic, i.e., immunogens, as well as substances which induce immunological unresponsiveness, or anergy, i.e., a lack of reactions by the body's defense mechanisms to foreign substances. As used herein, the term "antigen" is intended to mean full length proteins as well as peptide fragments thereof containing or comprising epitope.

The term "food producing animal" means animals which are used for human consumption such as swine, cattle, poultry, fish and the like, preferably food producing animal means swine and cattle, most preferably swine.

An "immunogenic composition" as used herein can refer to a polypeptide or a protein, such as for example a viral surface protein that elicits an immunological response as described herein. The term "immunogenic fragment" or "immunogenic portion" refers to a fragment or truncated and/or substituted form of a protein or polypeptide that includes one or more epitopes and thus elicits the immunological response described herein. In general, such truncated and/or substituted forms, or fragments will comprise at least six contiguous amino acids from a full-length protein. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

The term "immunizing" relates to an active immunization by the administration of an immunogenic composition to a food producing animal to be immunized, thereby causing an immunological response against the antigen included in such immunogenic composition.

The term "in need" or "of need", as used herein means that the administration/treatment is associated with the boosting or improvement in health or clinical signs or any other positive medicinal effect on health of the animals which receive the immunogenic composition in accordance with the present invention.

The term "vaccine" as used herein refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. By way of distinction the immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic material using suitable pharmaceutical compositions (polynucleotide vaccination). A vaccine may comprise one or simultaneously more than one of the elements described above. As used within specific aspects of the present invention "vaccine" refers to a live vaccine or live virus, also called recombinant vaccine. In another specific aspect of the present invention "vaccine" refers to an inactivated or killed virus including virus like particles (VLPs). Thus, a vaccine may be a subunit vaccine or a killed (KV) or inactivated vaccine.

The term "Multiplicity of Infection (M.O.I.)" describes how many infectious units, e.g. TCID50, of a virus preparation are used per cell to infect cultured cells. For example, a M.O.I. of 0.01 means that for every 100 cells in a culture vessel one infectious unit is inoculated.

The term "DNA vaccination" or "polynucleotide vaccination" means direct inoculation of genetic material using suitable pharmaceutical compositions.

Various physical and chemical methods of inactivation are known in the art. The term "inactivated" refers to a previously virulent or non-virulent virus or bacterium that has been irradiated (ultraviolet (UV), X-ray, electron beam or gamma radiation), heated, or chemically treated to inactivate or kill such virus or bacterium while retaining its immunogenicity. Suitable inactivating agents include beta-propiolactone, binary or beta- or acetyl-ethyleneimine, gluteraldehyde, ozone, and formalin (formaldehyde).

For inactivation by formalin or formaldehyde, formaldehyde is typically mixed with water and methyl alcohol to create formalin. The addition of methyl alcohol prevents degradation or cross reaction during the in activation process. One embodiment uses about 0.1 to 1% of a 37% solution of formaldehyde to inactivate the virus or bacterium. It is critical to adjust the amount of formalin to ensure that the material is inactivated but not so much that side effects from a high dosage occur.

More particularly, the term "inactivated" in the context of a virus means that the virus is incapable of replication in vivo or in vitro and, respectively, the term "inactivated" in the context of a bacterium means that the bacterium is incapable of reproduction in vivo or in vitro. For example, the term "inactivated" may refer to a virus that has been propagated in vitro, and has then been inactivated using chemical or physical means so that it is no longer capable of replicating. In another example, the term "inactivated" may refer to a bacterium that has been propagated, and then inactivated using chemical or physical means resulting in a suspension of the bacterium, fragments or components of the bacterium, such as resulting in a bacterin which may be used as a component of a vaccine.

As used herein, the terms "inactivated", "killed" or "KV" are used interchangeably.

The term "live vaccine" refers to a vaccine comprising either a living organism or a replication competent virus or viral vector.

A "pharmaceutical composition" essentially consists of one or more ingredients capable of modifying physiological, e.g., immunological functions, of the organism it is administered to, or of organisms living in or on the organism. The term includes, but is not restricted to, antibiotics or antiparasitics, as well as other constituents commonly used to achieve certain other objectives such as, but not limited to, processing traits, sterility, stability, feasibility to administer the composition via enteral or parenteral routes such as oral, intranasal, intravenous, intramuscular, subcutaneous, intradermal, or other suitable route, tolerance after administration, or controlled release properties. One non-limiting example of such a pharmaceutical composition, solely given for demonstration purposes, could be prepared as follows: cell culture supernatant of an infected cell culture is mixed with a stabilizer (e.g., spermidine and/or bovine serum albumin (BSA) and the mixture is subsequently lyophilized or dehydrated by other methods. Prior to vaccination, the mixture is then rehydrated in aqueous (e.g., saline, phosphate buffered saline (PBS) or non-aqueous solutions (e.g., oil emulsion, aluminum-based adjuvant).

As used herein, "pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John Wiley and Sons, NY, pp51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIM adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Attenuation" means reducing the virulence of a pathogen. In the present invention "attenuation" is synonymous with "avirulent". In the present invention, an attenuated virus is one in which the virulence has been reduced so that it does not cause clinical signs of infection but is capable of inducing an immune response in the target animal, but may also mean that the clinical signs are reduced in incidence or severity in animals infected with the attenuated virus, especially the EHV-1 RacH viral vector as claimed, in comparison with a "control group" of animals infected with non-attenuated virus or pathogen and not receiving the attenuated virus. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent pathogen such as for example an attenuated viral vector as claimed, especially the EHV-1 (preferably RacH) viral vector as claimed, is suitable for the generation of a modified live vaccine (MLV) or modified live immunogenic composition.

The term "treatment and/or prophylaxis" refers to the lessening of the incidence of the infection in a herd or the reduction in the severity of clinical signs caused by or associated with the particular infection. Thus, the term "treatment and/or prophylaxis" also refers to the reduction of the number of animals in a herd that become infected with the pathogen or to the reduction of the severity of clinical signs normally associated with or caused by the infection in a group of animals which animals have received an effective amount of the immunogenic composition as provided herein in comparison to a group of animals which animals have not received such immunogenic composition.

The "treatment and/or prophylaxis" generally involves the administration of an effective amount of the immunogenic composition of the present invention to an animal or herd of animals in need of or that could benefit from such a treatment/prophylaxis. The term "treatment" refers to the administration of the effective amount of the immunogenic composition once the animal or at least some animals of the herd is/are already infected with such pathogen and wherein such animals already show some clinical signs caused by or associated with such pathogen infection. The term "prophylaxis" refers to the administration to an animal prior to any infection of such animal with a pathogen or at least where such animal or none of the animals in a group of animals do not show any clinical signs caused by or associated with the infection by such pathogen. The terms "prophylaxis" and "preventing" are used interchangeable in this application.

The term "clinical signs" as used herein refers to signs of infection of an animal from the pathogen. The clinical signs of infection depend on the pathogen selected. Examples for such clinical signs include but are not limited to respiratory distress, otitis, roughened hair coat, slight fever, depression, and reduced appetite. However, the clinical signs also include but are not limited to clinical signs that are directly observable from a live animal. Examples for clinical signs that are directly observable from a live animal include nasal and ocular discharge, lethargy, coughing, wheezing, thumping, elevated fever, weight loss, dehydration, lameness, wasting, paleness of the skin, unthriftiness and the like.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount refers to colony forming units (CFU) per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

An "immune response" or "immunological response" means, but is not limited to, the development of a cellular and/or antibody-mediated immune response to the (immunogenic) composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

"Protection against disease", "protective immunity", "functional immunity", "reduction of clinical symptoms", "induction/production of neutralizing antibodies and/or serum conversion", and similar phrases, means a partial or complete response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection are lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of malaria. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

The term "reduction of viremia" induced by a virus means, but is not limited to, the reduction of virus entering the bloodstream of an animal, wherein the viremia level, i.e. the number of virus DNA or RNA copies per mL of blood serum or the number of plaque forming colonies per deciliter of blood serum, is reduced in the blood serum of animals receiving the composition of the present invention by at least 50% in comparison to animals not receiving the composition and may become infected. More preferably, the viremia level is reduced in animals receiving the composition of the present invention by at least 90%, preferably by at least 99.9%, more preferably by at least 99.99%, and even more preferably by at least 99.999%.

The term "pathogen" is well known to the person skilled in the art. However, the term "pathogen" comprises bacteria and viruses. The term "pathogen" comprises pathogens such as Schmallenberg virus, Influenza A Virus, Porcine Respiratory and Reproductive Syndrome Virus, Porcine Circovirus, Classical Swine Fever Virus, African Swine Fever Virus, Hepatitis E Virus, Bovine Viral Diarrhea Virus, Rabies Virus, Feline Morbillivirus, *Clostridium tetani, Mycobacterium tuberculosis, Actinobacillus Pleuropneumoniae.*

The term "food producing animal" means animals which are used for human consumption such as swine, cattle, poultry, fish and the like, preferably swine.

The term "companion animal" comprises animals such cat, Equine or dog.

As used herein, the term "viremia" is particularly understood as a condition in which virus particles reproduce and/or circulate in the bloodstream of an animal, in particular of a mammal, a bird, or of an insect.

"Safety" refers to the absence of adverse consequences in a vaccinated animal following vaccination, including but not limited to: potential reversion of a virus-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—, an immune response in said animal.

"Mortality", in the context of the present invention, refers to death caused by an infection, and includes the situation where the infection is so severe that an animal is euthanized to prevent suffering and provide a humane ending to its life.

Formulations

The subject to which the composition is administered is preferably an animal, including but not limited to cattle, horses, sheep, pigs, poultry (e.g. chickens), goats, cats, dogs, hamsters, mice and rats, most preferably the mammal is a swine.

The formulations of the invention comprise an effective immunizing amount of one or more immunogenic compositions and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Methods of Treatment

Preferred routes of administration include but are not limited to intranasal, oral, intradermal, and intramuscular. Administration in drinking water, most preferably in a single dose, is desirable. The skilled artisan will recognize that compositions of the invention may also be administered in one, two or more doses, as well as, by other routes of administration. For example, such other routes include subcutaneously, intracutaneously, intraperitnoeally, intracutaneously, and depending on the desired duration and effectiveness of the treatment, the compositions according to the invention may be administered once or several times, also intermittently, for instance on a daily basis for several days, weeks or months and in different dosages such as about $10^3$ to $10^8$TCID50 (see viral titre above). In a specific aspect of the present invention the dosage is about $10^3$ to $10^8$ TCID50, especially for live virus/live vaccine.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a mammal, especially a pig. Associated with such container(s) can be a notice in the form prescribed by a governmental agency regulating the manufacture, use or sale of pharmaceuticals or biological products, which notice reflects approval by the agency of manufacture, use or sale for human administration.

Antigen Definitions

The term "swine influenza virus" is known by the person skilled in the art. The term swine influenza virus refers to a type A or type C influenza virus from the family orthomyxovirus that causes swine influenza. While orthomyxovirus has three groups: type A, type B and type C, only type A and type C influenza viruses infect pigs. Preferably, the swine influenza virus is a Swine Influenza A virus. Subtypes of swine influenza virus include H1N1, H1N2, H3N2, and H3N1. H9N2 and H5N1 can also be found in pigs. Preferably, a swine influenza virus is an influenza virus that has been isolated from swine.

The terms "HA" or "H", "NA" or "N" and "NP" are known by the person skilled in the art. However, in general, type A influenza viruses are divided into 17 H (hemagglutinin) and 10 N (Neuraminidase) subtypes which can give rise to many possible combinations (designated as H1N1, H1N2 . . . H2N1, H2N2 . . . H5N1, H5N2 . . . and so on). H (hemagglutinin) and N (neuraminidase) are surface glycoproteins in influenza A viruses such as SIAV. Further, N is the major antigenic target of neutralizing antibodies. Furthermore, NP (nucleoprotein) forms the nucleocapsid.

Sequences Overview

The following sequences are detailed and disclosed hereby in the present invention:

SEQ ID NO:1 EHV-1 ORF43 (UL18) gene sequence
SEQ ID NO:2 EHV-1 ORF54 (UL8) gene sequence
SEQ ID NO:3 Codon optimized ORF43 (UL18) gene sequence
SEQ ID NO:4 Codon optimized ORF54 (UL8) gene sequence
SEQ ID NO:5 171 bases upstream of ORF43 (UL18) gene
SEQ ID NO:6 265 bases downstream of ORF43 (UL18) gene
SEQ ID NO:7 mCMV promoter driven RFP gene with a BGH poly A flanked by SEQ ID NO:5 and 6
SEQ ID NO:8 Kanamycin gene flanked by SEQ ID NO:5 and 6
SEQ ID NO:9 161 bases upstream of ORF43 (UL18) gene
SEQ ID NO:10 120 bases downstream of ORF43 (UL18) gene
SEQ ID NO:11 200 nucleotides upstream of ORF54 (UL8) gene
SEQ ID NO:12 200 nucleotides downstream of ORF54 (UL8) gene
SEQ ID NO:13 mCMV promoter driven RFP gene with a BGH poly A flanked by SEQ ID NO:5 and 6
SEQ ID NO:14 HA sequence cloned at ORF1/3 (UL56) site SEQ ID NO:15 Nucleotide sequence of transfer vector pU70-p455-71K71

SEQ ID NO:16 Nucleotide sequence of transfer plasmid pU70-p455-H3-71K7

SEQ ID NO:17 left (Up70) flanking region (417 bp)

SEQ ID NO:18 right (Up71) flanking region (431 bp)

SEQ ID NO:19 flanking region left (up orf70) in the wild-type EHV-1 strain ab4 (Genbank accession number AY665713.1), located at nucleotides 127264-127680

SEQ ID NO:20 flanking region right (up orf71) in the wild-type EHV-1 strain ab4 (Genbank accession number AY665713.1), located at nucleotides 128484-128913

SEQ ID NO:21 truncated flanking region in the RED system: left (Up70) flanking region (283 bp)=identical to the 3' 283 bp of the 417 bp "classical" flanking region SEQ ID NO:22 truncated flanking region in the RED system: right (Up71) flanking region (144 bp)=identical to the 5' 144 bp of the 431 bp "classical" flanking region SEQ ID NO:23 Deleted portion in the wild-type ab4 (Genbank accession number AY665713.1) genome sequence, nt 127681-128482

SEQ ID NO:24 Deleted portion in the RacH genome sequence (no nt numbers available because complete genome sequence not known)

CLAUSES

The following Clauses are described herein:

The invention provides the following clauses:

1. A replication deficient Equid Alphaherpesvirus (EHV) vector comprising an inactivation of UL18 and/or UL8.
2. The replication deficient EHV vector of clause 1, wherein UL18 is inactivated.
3. The replication deficient EHV vector of clause 1 or 2, wherein UL8 is inactivated.
4. The replication deficient EHV vector of any one of clauses 1 to 3, wherein UL18 and UL8 are inactivated.
5. The replication deficient EHV vector of any one of clauses 1 to 4, wherein the inactivation of UL18 is a complete or partial deletion, a complete or partial truncation, a complete or partial substitution, a complete or partial inversion, an insertion.
6. The replication deficient EHV vector of any one of clauses 1 to 5, wherein the inactivation of UL8 is a complete or partial deletion, a complete or partial truncation, a complete or partial substitution, a complete or partial inversion, an insertion.
7. The replication deficient EHV vector of any one of clauses 1 to 6, wherein the start codon of UL18 (ATG, nucleotides 1-3 of SEQ ID NO:1) is inactivated.
8. The replication deficient EHV vector of clause 7, wherein said inactivation of the start codon (ATG) of UL18 is a deletion, substitution, inversion or insertion.
9. The replication deficient EHV vector of any one of clauses 1 to 8, wherein the start codon of UL8 (ATG, nucleotides 1-3 of SEQ ID NO:2) is inactivated.
10. The replication deficient EHV vector of clause 9, wherein said inactivation of the start codon (ATG) of UL8 is a deletion, substitution, inversion or insertion.
11. The replication deficient EHV vector of any one clauses 1 to 10, wherein at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 925 nucleotides, at least 940 nucleotides from the 5'-Terminus of the start codon (ATG, nucleotides 1-3 of SEQ ID NO:1) of the UL18 are deleted, substituted or inverted.
12. The replication deficient EHV vector of any one clauses 1 to 11, wherein at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 925 nucleotides, at least 940 nucleotides from the A, T, or G of the start codon (ATG, nucleotides 1-3 of SEQ ID NO:1) of the UL18 are deleted, substituted or inverted.
13. The replication deficient EHV vector of any one clauses 1 to 12, wherein at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 925 nucleotides, at least 940 nucleotides are deleted, substituted, or inverted within the UL18.
14. The replication deficient EHV vector of any one clauses 1 to 13, wherein a DNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the DNA sequence as set forth in SEQ ID NO:1 is deleted, substituted, or inverted within the UL18.
15. The replication deficient EHV vector of any one clauses 1 to 14, wherein at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 300 nucleotides, at least 500 nucleotides, at least 800 nucleotides, at least 1000 nucleotides are inserted within the UL18.
16. The replication deficient EHV vector of any one clauses 1 to 15, wherein at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 1000 nucleotides, at least 1250 nucleotides, at least 1500, nucleotides, at least 1750 nucleotides, at least 2000 nucleotides, at least 2225 nucleotides from the 5'-Terminus of the start codon (ATG, nucleotides 1-3 of SEQ ID NO:2) of the UL8 are deleted, substituted or inverted.
17. The replication deficient EHV vector of any one clauses 1 to 16, wherein at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 1000 nucleotides, at least 1250 nucleotides, at least 1500, nucleotides, at least 1750 nucleotides, at least 2000 nucleotides, at least 2225 nucleotides from the A, T, or G of the start codon (ATG, nucleotides 1-3 of SEQ ID NO:2) of the UL8 are deleted, substituted or inverted.

18. The replication deficient EHV vector of any one clauses 1 to 17, wherein at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 1000 nucleotides, at least 1250 nucleotides, at least 1500, nucleotides, at least 1750 nucleotides, at least 2000 nucleotides, at least 2225 nucleotides are deleted, substituted, or inverted within the UL8.

19. The replication deficient EHV vector of any one clauses 1 to 18, wherein a DNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the DNA sequence as set forth in SEQ ID NO:2 is deleted, substituted, or inverted within the UL8.

20. The replication deficient EHV vector of any one clauses 1 to 19, wherein at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 300 nucleotides, at least 500 nucleotides, at least 800 nucleotides, at least 1000 nucleotides are inserted within the UL8.

21. The replication deficient EHV vector of any one of clauses 1 to 20, wherein the EHV comprises an expression cassette comprising:
   (i) at least one exogenous nucleotide sequence of interest, preferably a gene of interest, more preferably an antigen encoding sequence, wherein said nucleotide sequence of interest, preferably a gene of interest, more preferably an antigen encoding sequence is optionally operably linked to a promoter sequence, and
   (ii) at least one upstream UL18 flanking region selected from the group consisting of: SEQ ID NO:5 and a 70%, 80%, 85%, 90%, 91%, 92%, 93%, 94%, 95%, 96%, 97%, 98%, 99% homologous and/or identical sequence thereof, SEQ ID NO:9 and a 70%, 80%, 85%, 90%, 91%, 92%, 93%, 94%, 95%, 96%, 97%, 98%, 99% homologous and/or identical sequence thereof, and
   (iii) at least one downstream UL18 flanking region selected from the group consisting of: SEQ ID NO.: 6 and a 70%, 80%, 85%, 90%, 91%, 92%, 93%, 94%, 95%, 96%, 97%, 98%, 99% homologous and/or identical sequence thereof, SEQ ID NO:10 and a 70%, 80%, 85%, 90%, 91%, 92%, 93%, 94%, 95%, 96%, 97%, 98%, 99% homologous and/or identical sequence thereof.

22. The replication deficient EHV vector of any one of clauses 1 to 21, wherein the EHV comprises an expression cassette comprising:
   (i) at least one exogenous nucleotide sequence of interest, preferably a gene of interest, more preferably an antigen encoding sequence, wherein said nucleotide sequence of interest, preferably a gene of interest, more preferably an antigen encoding sequence is optionally operably linked to a promoter sequence, and
   (ii) at least one upstream UL8 flanking region selected from the group consisting of: SEQ ID NO:11 and a 70%, 80%, 85%, 90%, 91%, 92%, 93%, 94%, 95%, 96%, 97%, 98%, 99% homologous and/or identical sequence thereof, and
   (iii) at least one downstream UL8 flanking region selected from the group consisting of: SEQ ID NO:12 and a 70%, 80%, 85%, 90%, 91%, 92%, 93%, 94%, 95%, 96%, 97%, 98%, 99% homologous and/or identical sequence thereof.

23. The replication deficient EHV vector of clause 21 or 22, wherein the insertion of the expression cassette inactivates UL18 and/or UL8.

24. The replication deficient EHV vector of any one clauses 21 to 23, wherein the insertion of the expression cassette into UL18 is characterized by a deletion of an approximately 945 bp portion within UL18 for RacH (SEQ ID NO:1) or a 70%, 80%, 85%, 90%, 91%, 92%, 93%, 94%, 95%, 96%, 97%, 98%, 99% homologous and/or identical sequence thereof.

25. The replication deficient EHV vector of any one clauses 21 to 24, wherein the insertion of the expression cassette into UL8 is characterized by a deletion of an approximately 2256 bp portion within UL8 for RacH (SEQ ID NO:2) or a 70%, 80%, 85%, 90%, 91%, 92%, 93%, 94%, 95%, 96%, 97%, 98%, 99% homologous and/or identical sequence thereof.

26. The replication deficient EHV vector of any one clauses 1 to 25, wherein the EHV vector comprises at least one flanking region selected from the group consisting of: SEQ ID NO:5, SEQ ID NO:6, SEQ ID NO:9, SEQ ID NO:10, and a 70%, 80%, 85%, 90%, 91%, 92%, 93%, 94%, 95%, 96%, 97%, 98%, 99% homologous and/or identical sequence of any one of these sequences.

27. The replication deficient EHV vector of any one clauses 1 to 26, wherein the EHV vector comprises (i) at least one upstream UL18 flanking region selected from the group consisting of: SEQ ID NO:5 and SEQ ID NO:9, and (ii) at least one downstream UL18 flanking region selected from the group consisting of: SEQ ID NO:6 and SEQ ID NO:10.

28. The replication deficient EHV vector of any one clauses 1 to 27, wherein the EHV vector comprises at least one flanking region selected from the group consisting of: SEQ ID NO:11 and SEQ ID NO:12 and a 70%, 80%, 85%, 90%, 91%, 92%, 93%, 94%, 95%, 96%, 97%, 98%, 99% homologous and/or identical sequence of any one of these sequences.

29. The replication deficient EHV vector of any one clauses 1 to 28, wherein the EHV vector comprises (i) at least one upstream UL8 flanking region selected from the group consisting of: SEQ ID NO:11 and (ii) at least one downstream UL8 flanking region selected from the group consisting of: SEQ ID NO:12.

30. The replication deficient EHV vector of any one clauses 1 to 29, wherein said EHV vector is a non-naturally and/or recombinant EHV.
31. The replication deficient EHV vector of any one clauses 1 to 30, wherein replication deficient means that the replication rate is reduced at least by 90%.
32. The replication deficient EHV vector of any one clauses 1 to 31, wherein replication deficient means that the replication rate is reduced at least by 95%.
33. The replication deficient EHV vector of any one clauses 1 to 32, wherein replication deficient means that the replication rate is reduced at least by 99%.
34. The replication deficient EHV vector of any one clauses 1 to 33, wherein replication deficient means that the replication rate is abolished completely.
35. The replication deficient EHV vector of any one clauses 1 to 34, wherein the replication rate is measured by a $TCID_{50}$ assay.
36. The replication deficient EHV vector of any one clauses 1 to 35, wherein the replication deficient EHV vector is still infective.
37. The replication deficient EHV vector of any one clauses 1 to 36, wherein the EHV vector is still infective, can replicate in infected eukaryotic cell lines, but only be packaged as a replication-competent virus in complementing cell lines.
38. The replication deficient EHV vector of any one of clauses 1 to 37, wherein the EHV vector comprises at least one nucleotide sequence of interest, preferably a gene of interest, more preferably an antigen encoding sequence, inserted into an insertion site, preferably UL56 and/or US4.
39. The replication deficient EHV vector of any one of clauses 1 to 38, wherein the EHV vector comprises two or more nucleotide sequences of interest, preferably genes of interest, more preferably antigen encoding sequences inserted into two or more insertion sites.
40. The EHV vector of clause 38 or 39, wherein the insertion into US4 is characterized by a partial deletion, truncation, substitution, modification or the like in US4, wherein US5 remains functional.
41. The EHV vector of any one clause 38 to 40, wherein the insertion into US4 is characterized by the deletion of an approximately 801 bp portion within US4 for RacH (SEQ ID NO:24) or a 70%, 80%, 85%, 90%, 91%, 92%, 93%, 94%, 95%, 96%, 97%, 98%, 99% homologous and/or identical sequence thereof.
42. The EHV vector of any one of clauses 38 to 41, wherein the EHV vector comprises at least one flanking region selected from the group consisting of: SEQ ID NO:17, SEQ ID NO:18, SEQ ID NO:19, SEQ ID NO:20, SEQ ID NO:21, and SEQ ID NO:22 and a 70%, 80%, 85%, 90%, 91%, 92%, 93%, 94%, 95%, 96%, 97%, 98%, 99% homologous and/or identical sequence of any one of these sequences.
43. The EHV vector of any one of clauses 38 to 42, wherein the EHV vector comprises (i) at least one left US4 flanking region selected from the group consisting of: SEQ ID NO:17, SEQ ID NO:19, and SEQ ID NO:21, and (ii) at least one right US4 flanking region selected from the group consisting of: SEQ ID NO:18, SEQ ID NO:20, and SEQ ID NO:22.
44. The replication deficient EHV vector of any one of clauses 21 to 43, wherein said nucleotide sequence of interest is recombinant and/or heterologous and/or exogenous.
45. The replication deficient EHV vector of any one of clauses 21 to 44, wherein said antigen encoding sequence relates to a pathogen infecting a food producing animal such as swine, cattle or poultry or companion animals such as cat, Equine or dog.
46. The replication deficient EHV vector of any one of clauses 21 to 45, wherein the antigen encoding sequence is from a pathogen selected, but not limited to, from the list: Schmallenberg virus, Influenza A Virus, Porcine Respiratory and Reproductive Syndrome Virus, Porcine Circovirus, Classical Swine Fever Virus, African Swine Fever Virus, Hepatitis E Virus, Bovine Viral Diarrhea Virus, Rabies Virus, Feline Morbillivirus, *Clostridium tetani, Mycobacterium tuberculosis, Actinobacillus Pleuropneumoniae.*
47. The replication deficient EHV vector of any one of clauses 21 to 46, further comprising additional regulatory sequences such as a termination signal or polyadenylation sequence.
48. The replication deficient EHV vector of any one of clauses 21 to 47, wherein the gene of interest is operably linked to a regulatory sequence, preferably a promoter sequence.
49. The replication deficient EHV vector of any one of clauses 21 to 48, wherein the promoter sequence(s) operably linked to the sequence or gene of interest are selected from, but not limited to, the group consisting of: SV40 large T, HCMV and MCMV immediate early gene 1, human elongation factor alpha promoter, baculovirus polyhedrin promoter, a Polymerase II promoter, a functional fragment.
50. The replication deficient EHV vector of any one of clauses 21 to 49, wherein the promoter sequence operably linked to at least one gene of interest is MCMV or a functional fragment thereof or the complementary nucleotide sequences thereof.
51. The replication deficient EHV vector of any one of clauses 21 to 50, wherein the promoter sequence operably linked to at least one gene of interest is the endogenous promoter of UL8 or UL18.
52. The replication deficient EHV vector of any one of clauses 1 to 51, wherein the EHV vector is selected from the group consisting of EHV-1, EHV-3, EHV-4, EHV-8 and EHV-9.
53. The replication deficient EHV vector of any one of clauses 1 to 52, wherein the EHV vector is EHV-1, preferably RacH.
54. A mammalian host cell characterized in that it comprises a replication deficient EHV vector according to any one of clauses 1 to 53.
55. A cell line expressing UL8 and/or UL18 of EHV or functional parts thereof for culturing the replication deficient EHV vector of any one of clauses 1 to 53.
56. A cell line comprising a plasmid comprising an expression cassette comprising UL8 and/or UL18 of EHV or functional parts thereof, wherein the cell line is expressing UL8 and/or UL18 or functional parts thereof.
57. The cell line according to clause 55 or 56, wherein the cell is selected, but not limited from the group of: Vero cells, RK-13 (rabbit kidney), ST (Swine testicular), MDCK (Madin-Darby Canine Kidney), MDBK (Madin-Darby Bovine Kidney) and Equine dermal cells (NBL-6).
58. The cell line according to any one of clauses 55 to 57, wherein the cell line is an ST cell line.

59. A method for producing a replication deficient Equid Alphaherpesvirus (EHV) comprising inactivating UL18 and/or UL8 according to any one of clauses 1 to 53.
60. A method for producing a replication deficient Equid Alphaherpesvirus (EHV) comprising the steps of:
    a) providing a wild-type EHV or an attenuated EHV;
    b) inactivating UL18 and/or UL8 of the EHV of step a) and selecting for EHV clones which are not carrying complete or a functional part of UL18 and/or UL 8;
    c) providing a complementing cell line expressing UL18 and/or UL8 or functional parts thereof;
    d) obtaining the replication deficient Equid Alphaherpesvirus (EHV) by cultivating the EHV from step b) with the complementing cell line from step c).
61. An immunogenic composition comprising one or more EHV vectors according to any one of clauses 1 to 53.
62. The immunogenic composition of clause 61, wherein said immunogenic composition further comprises a pharmaceutically acceptable carrier.
63. The immunogenic composition of any one of clause 61 or 62, wherein said immunogenic composition is a vaccine.
64. A method for immunizing a subject comprising administering to such subject an immunogenic composition of any one of clauses 61 to 63.
65. A method of treating or preventing clinical signs caused by a pathogen in a subject of need, the method comprising administering to the subject a therapeutically effective amount of an immunogenic composition according to any one of clauses 61 to 63.
66. The immunogenic composition of any one of clauses 61 to 63 for use in a method for immunizing a subject comprising administering said immunogenic composition to such subject.
67. The immunogenic composition of any one of clauses 61 to 63 for use in a method of treating or preventing clinical signs caused by a pathogen in a subject of need, the method comprising administering to the subject a therapeutically effective amount of said immunogenic composition.
68. The method or use of any one of clauses 64 to 67, wherein said subject is selected from the list consisting of swine, cattle, poultry, cat, equine and dog.
69. The method or use of any one of clauses 64 to 68, wherein the immunogenic composition is administered once.
70. The method of any one of clauses 64 to 69, wherein the immunogenic composition is administered at two or more doses.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Generation Stable Cell Line Expressing EHV-1 ORF 43 (UL18) or ORF 54 (UL8) Genes Synthetic, codon-optimized ORF 43 (ORF 43(co)) gene, SEQ ID NO:3, (based on the nucleotide sequence of EHV-1 RacH strain ORF 43 gene, SEQ ID NO:1) was digested with XhoI/BamHI and ligated into pCEP vector (Invitrogen, Catalog #V044-50) digested with the same restriction endonucleases. The resulting plasmid, pCEP-ORF43 (co) (FIG. 1), was linearized and transfected into Swine testicular cells (ST). After two weeks of selection with hygromycin, stable cells expressing ORF43 (co) genes (ST-43-CO cells) were used to rescue replication defective EHV-1 virus.

Figure 2:
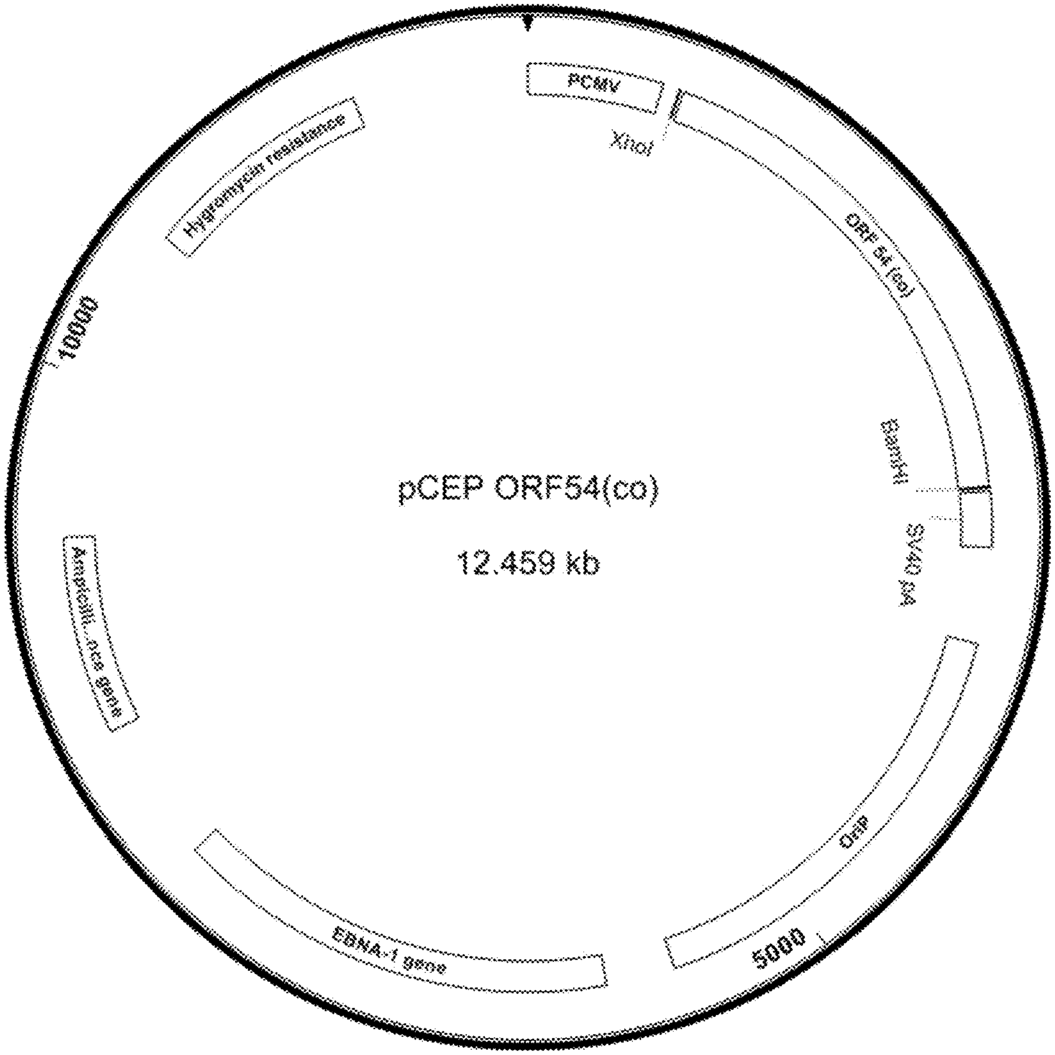
FIG. 2: Plasmid map of the expression plasmid, pCEP-ORF54(CO). This vector expresses a codon-optimized EHV-1 ORF54 gene through a CMV promoter and was used to generate one of the stable cell lines.

Synthetic, codon-optimized ORF 54 (ORF 54(co)) gene, SEQ ID NO:4 (based on the nucleotide sequence of EHV-1 RacH strain ORF 54 gene, SEQ ID NO:2) was digested with XhoI/BamHI and ligated into pCEP vector (Invitrogen, Catalog #V044-50) digested with the same restriction endonucleases. The resulting plasmid, pCEP-ORF54 (co) (FIG. 2), was linearized and transfected into Swine testicular cells (ST). After two weeks of selection with hygromycin, stable cells expressing ORF54 (co) genes (ST-54-CO cells) were used to rescue replication defective EHV-1 virus.

EXAMPLE 2

Vector Construction and Replication Defective EHV Virus Rescue EHV-1ΔORF43 Virus, with mCMV Promoter Driven RFP Replacing ORF 43

Figure 3:
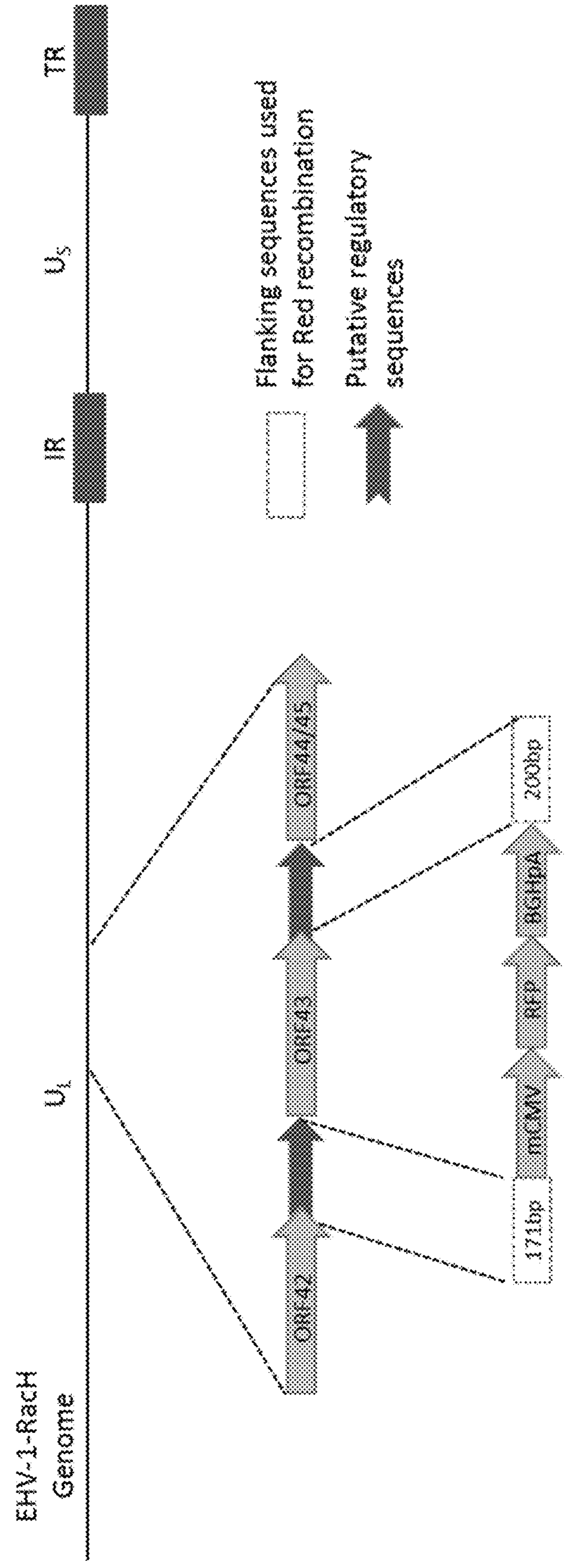
FIG. 3: Schematic illustration of Cloning of mCMV driven RFP into ORF 43 site in EHV-1 BAC DNA, with the ORF42-ORF45 region enlarged.

Synthetic DNA with a multiple cloning site (MCS) flanked by 171 nucleotides upstream (SEQ ID NO:5) and 265 nucleotides downstream (SEQ ID NO:6) of ORF 43 gene was designed. mCMV (murine CMV promoter) driven Red fluorescent protein (RFP/mCherry) (Shaner et al., 2004) was used as a reporter gene. As transcription termination signal and mRNA stabilizing function the bovine growth hormone polyadenylation sequence (BGHpA, Goodwin & Rottman, 1992) was used directly downstream at the 3' end of the reporter (RFP) gene. RFP gene digested with MluI/SalI restriction endonucleases was cloned into the MCS to generate the plasmid pUC43-mCMV-RFP. From this plasmid, DNA fragment with mCMV-RFP-BGH poly-A flanked by ORF 43 flanks (SEQ ID NO 7) was digested and cloned into EHV-1 RacH BAC DNA using the RED recombination system to generate EHV-1-43-mCMV RFP. Red recombination knocks-out ORF43 and replaces it with mCMV-RFP-BGH poly-A (FIG. 3). After a kanamycin selection, EHV-1-43-mCMV RFP BAC DNA was later transfected into ST-43-CO cells to rescue recombinant virus-rEHV-1-43-mCMV-RFP.

EXAMPLE 3

EHV-1ΔORF43 Virus, with Endogenous EHV-1 Promoter Driven RFP Replacing ORF 43

Figure 4:
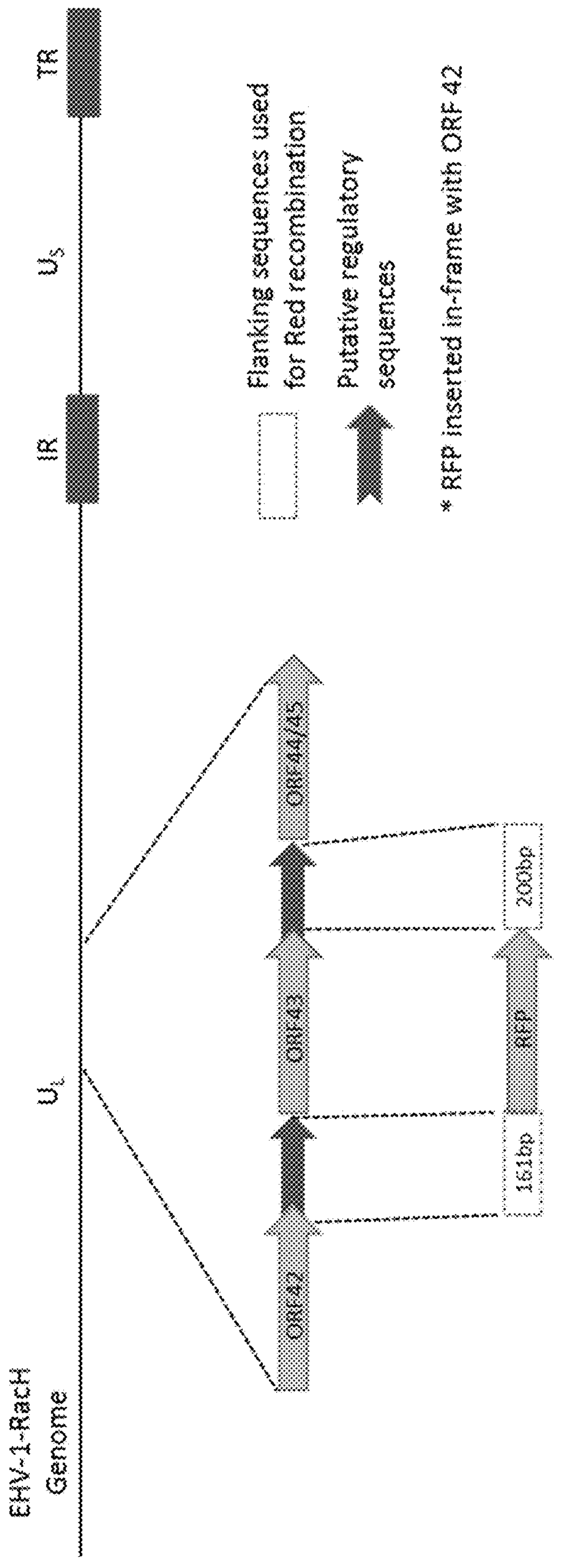
FIG. 4: Schematic illustration of Cloning of RFP into ORF 43 site in EHV-1 BAC DNA, with the ORF42-ORF45 region enlarged.
Figure 5:
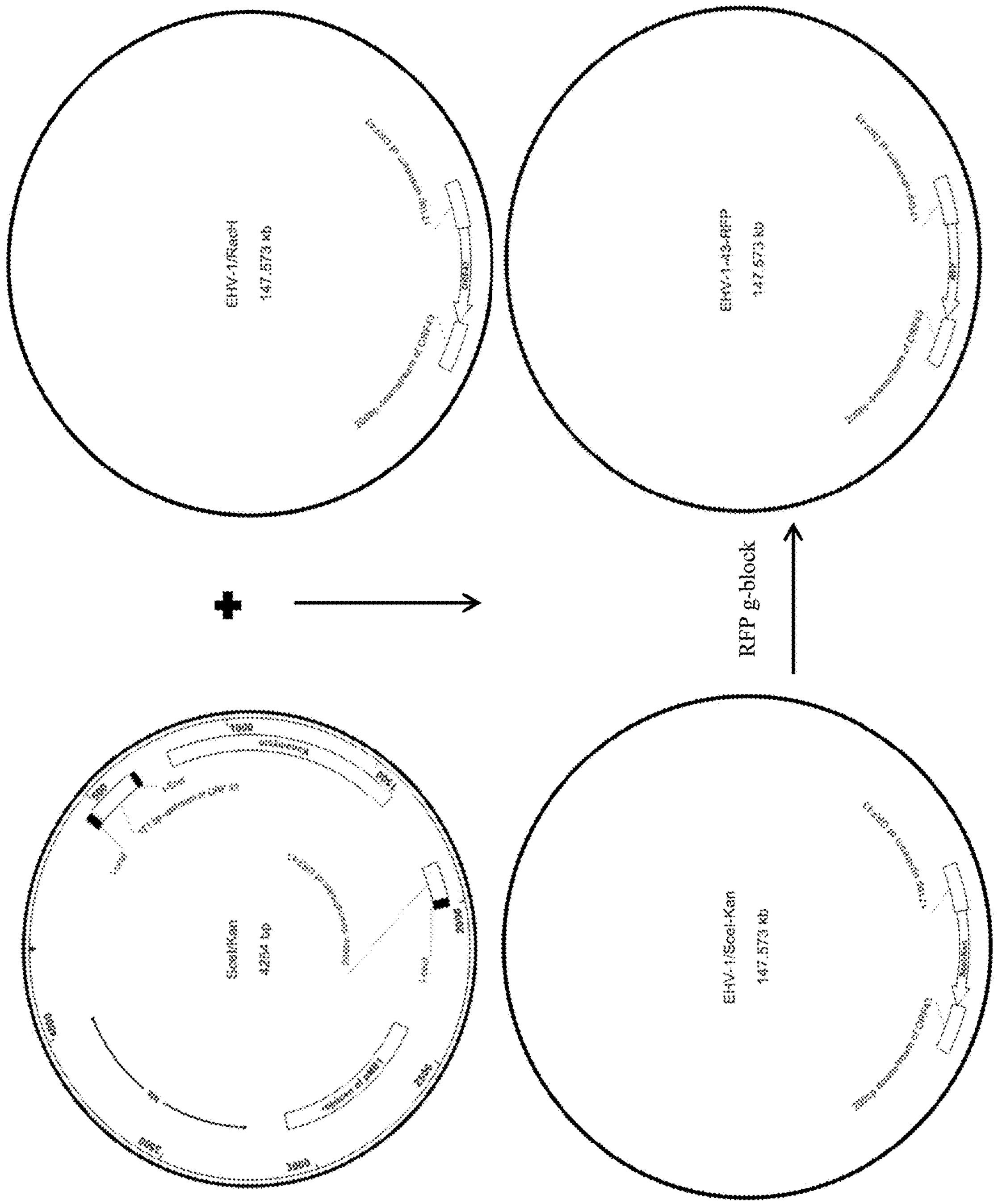
FIG. 5: Modified RED recombination used for cloning RFP into ORF43 region. Upper panel: Plasmids not to scale. SceI/Kan plasmid digested with I-CeuI restriction endonuclease. SceI/Kan fragment (flanked by ORF 43 sequences) transformed into GS183 cells carrying EHV-/RacH BAC DNA. Chloramphenicol and Kanamycin selection was used to select EHV-1/RacH clones where ORF43 was replaced by SceI/Kan. Intermediate clone designated EHV-1/SceI-Kan. Lower panel: Plasmids not to scale. RFP (flanked by ORF 43 sequences) g-block DNA was transformed into GS1783 cells carrying EHV-1/SceI-Kan, incubated with Arabinose and selected with Chloramphenicol/Arabinose. RFP DNA replaced SceI/Kan fragment at ORF43 in EHV-1/Sce-Kan clones generate EHV-1-43-RFP.

In another version of replacing replication defective EHV-1 virus, ORF 43 was replaced by RFP gene in frame using modified RED recombination protocol (FIG. 5). First, synthetic DNA SceI/Kanamycin DNA, flanked by 171 nucleotides upstream (SEQ ID NO:5) and 265 nucleotides downstream (SEQ ID NO:6) of ORF 43 gene was designed. This DNA fragment (SEQ ID NO:8) was transformed into *E. coli* K12 GS1783 carrying EHV-1 BAC DNA. Selection with Kanamycin resulted in intermediate EHV-1 clones where ORF 43 was replaced with SceI/Kanamycin fragment. Next, RFP gene flanked by 161 nucleotides upstream (SEQ ID NO 9) and 120 nucleotides downstream (SEQ ID NO:10) of ORF 43 gene was transformed into the above clones to select for EHV-1 BAC DNA clones where ORF43 gene was replaced with RFP in frame (EHV-1-43-RFP) (FIG. 4). EHV-1-43 RFP BAC DNA was transfected into ST-43-CO cells to rescue recombinant virus-rEHV-1-43-RFP. Because we did not include an external promoter, RFP expression in this scenario is dependent on the inherent EHV-1 gene expression by the endogenous ORF 43 promoter.

EXAMPLE 4

EHV-1ΔORF 54 Virus, with mCMV Promoter Driven RFP Replacing ORF 54

Figure 6:
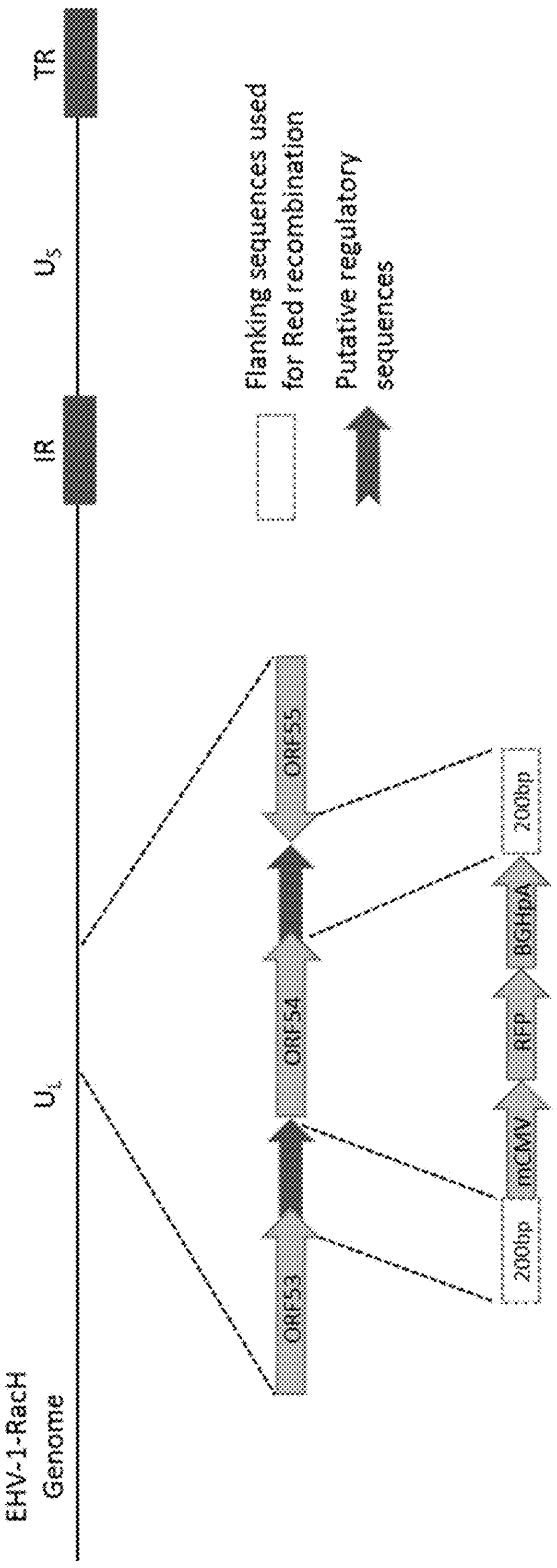
FIG. 6: Schematic illustration of Cloning of mCMV-RFP-pA into EHV-1 ORF 54 site in EHV-1 BAC DNA, with the ORF53-ORF55 region enlarged.
$U_L$=long unique segment
$U_S$=short unique segment
IR=inner inverted repeat
TR=terminal inverted repeat
orf=open reading frame
bp=base pairs

Synthetic DNA with a MCS flanked by 200 nucleotides upstream (SEQ ID NO:11) and 200 nucleotides downstream (SEQ ID NO:12) of ORF 54 gene was designed. mCMV driven RFP gene digested with MluI/SalI restriction endonucleases was cloned into the MCS to generate the plasmid pUC54-mCMV-RFP. From this plasmid, DNA fragment with mCMV-RFP-BGH poly-A flanked by ORF 54 flanks (SEQ ID NO:13) was digested with I-CeuI and cloned into EHV-1 RacH BAC DNA using the RED recombination system to generate EHV-1-54-mCMV RFP. Red recombination knock-out ORF54 and insert mCMV-RFP-BGH poly-A are in the same region (FIG. 6). After a kanamycin selection the EHV-1-54-mCMV RFP BAC DNA was later transfected into ST-54-CO cells to rescue recombinant virus-rEHV-1-54-mCMV-RFP.

EXAMPLE 5

Replication Defective EHV-1 Virus with Transgenes at ORF43 or ORF54

Regular ST cells, ST-43-CO cells and ST-54-CO cells were infected with different multiplicity of infection (MOI) of EHV-1/RacH, rEHV-1-43-mCMV-RFP, rEHV-1-43-RFP and rEHV-1-54-mCMV-RFP viruses. Infected cells were observed every 24h for gene expression and plaque formation by Fluorescence microscopy. Cytopathic effect (CPE) was monitored by light microscopy; virus was harvested at 70% CPE and tittered by TCID50.

Figure 7:
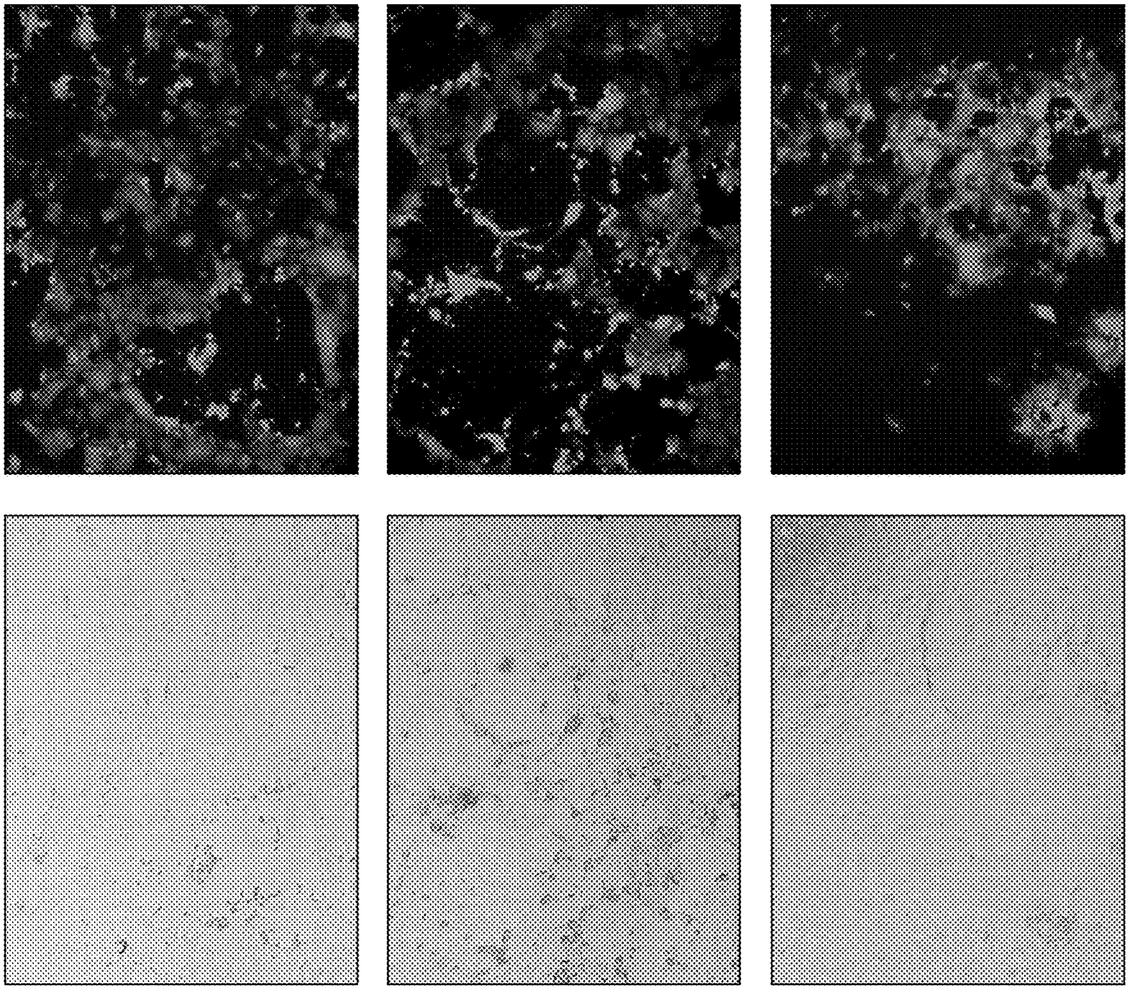
FIG. 7: ST (upper panel), ST-43-CO and (middle panel), ST-54-CO cells infected with EHV-1/RacH virus show similar CPE. Infected cells express GFP (right panel) but not RFP (data not shown)

As seen in FIG. 7, EHV-1/RacH virus causes significant CPE in all three cell lines. Distinctive plaques observed in all cells infected with EHV-1/RacH virus established that the stable cells generated in Example 1 and Example 2 support EHV-1 replication as well as regular ST cells.

Figure 8:
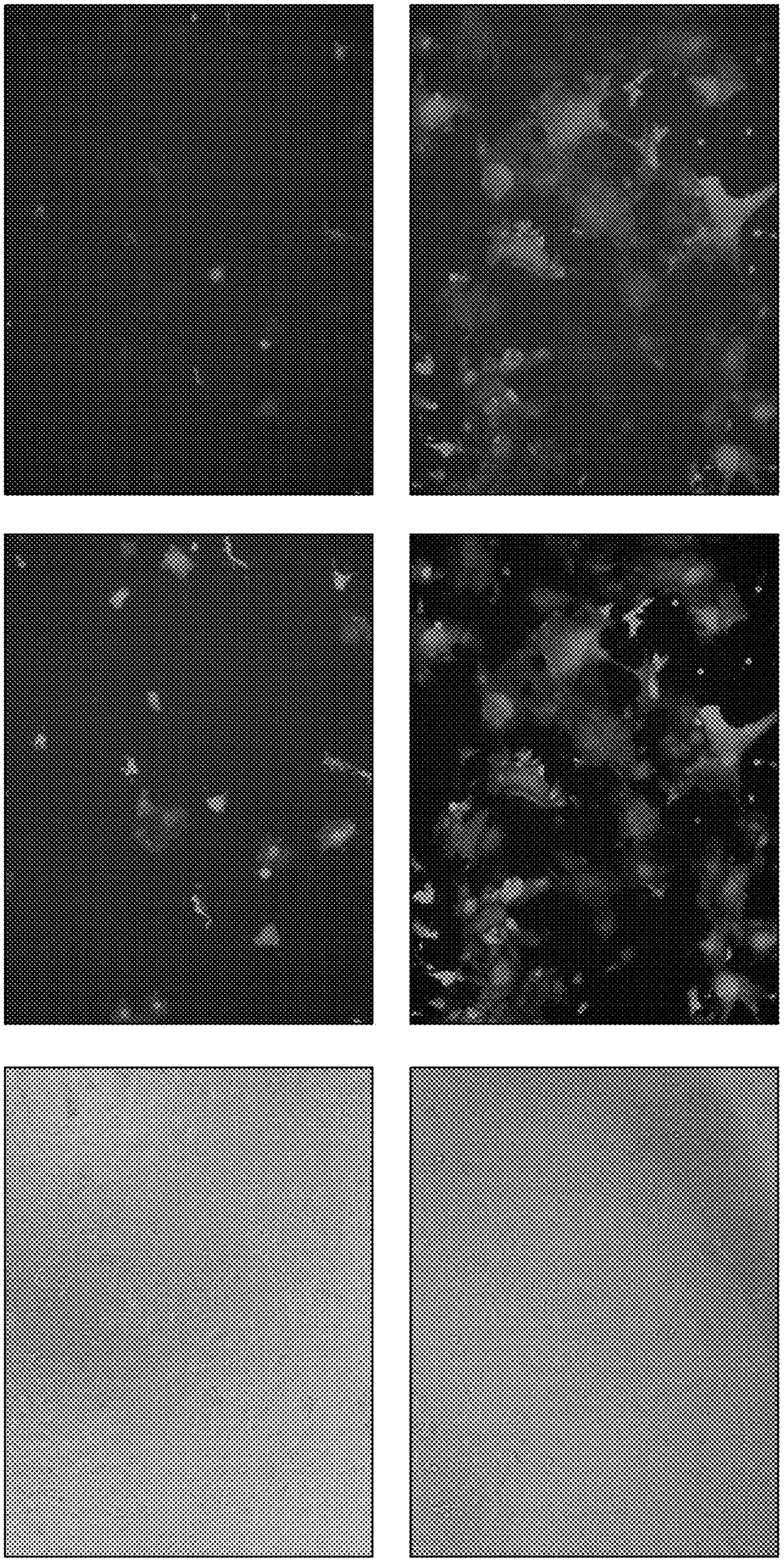
FIG. 8: ST (upper panel) and ST-43-CO and (lower panel) rEHV-1-43-RFP virus. Infected cells express GFP (middle panel) and RFP (right panel), but virus spread and CPE observed only in rEHV-1-43-RFP virus infected ST-43-CO cells.

Regular ST cells and ST-43-CO cells were infected with rEHV-1-43-RFP virus (FIG. 8). Although both cells were infected with rEHV-1-43-RFP virus (as seen from GFP expression), CPE and virus production was observed only in ST-43-CO cells. Transgene (RFP) expression was observed in all of the infected cells but visible CPE or plaques were only observed in only ST-43-CO cells.

Figure 9:
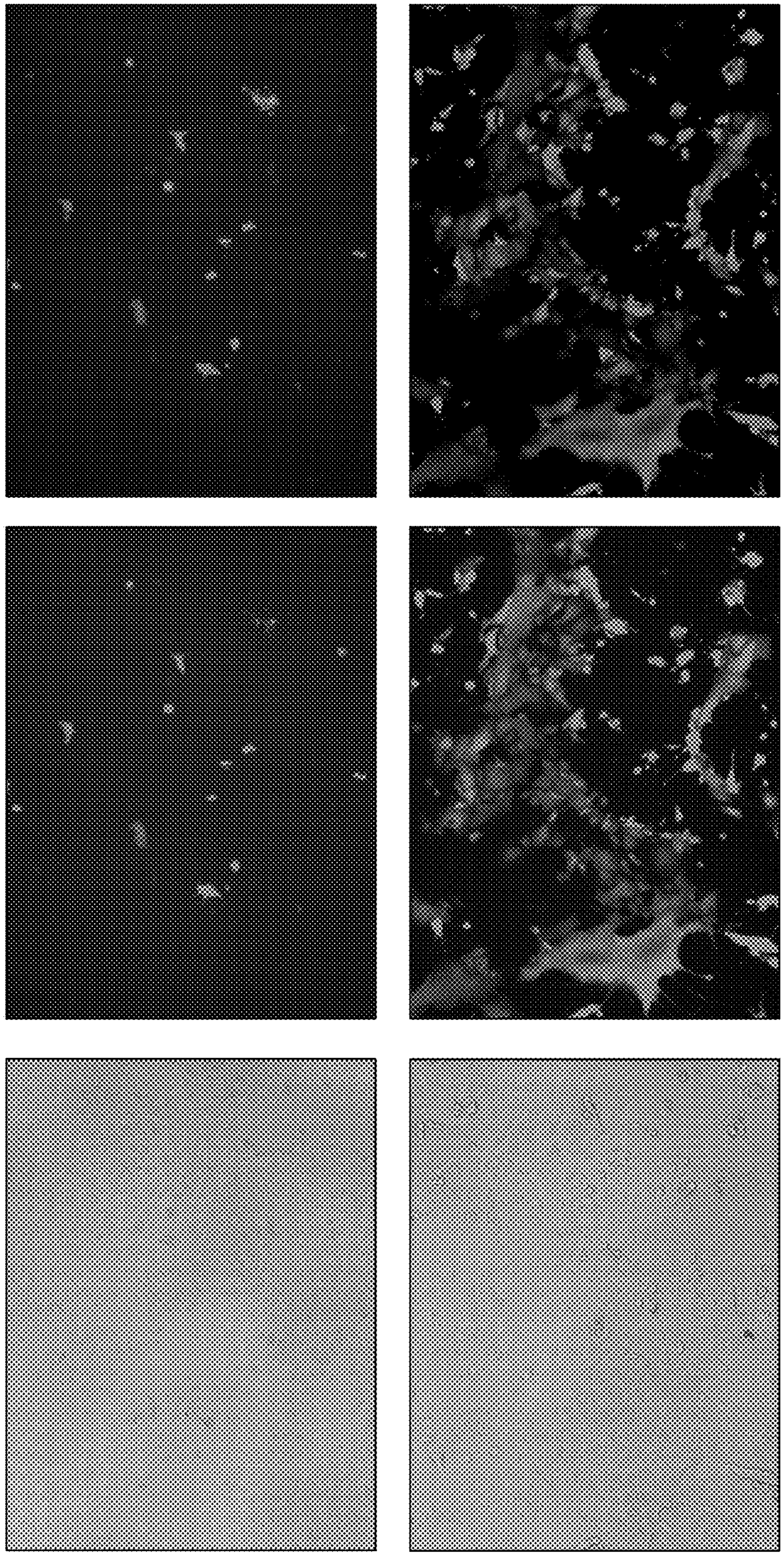
FIG. 9: ST (upper panel) and ST-43-CO and (lower panel) rEHV-1-43-mCMV-RFP virus. Infected cells express GFP (middle panel) and RFP (right panel), but virus spread and CPE observed only in rEHV-1-43-mCMV-RFP virus infected ST-43-CO cells.

Next, regular ST cells and ST-43-CO cells were infected with rEHV-1-43-mCMV-RFP virus (FIG. 9). Although both cells were infected with rEHV-1-43-mCMV-RFP virus (as seen from GFP expression), CPE and virus production was observed only in ST-43-CO cells. Transgene (RFP) expression was observed in all of the infected cells but visible CPE or plaques were only observed in only ST-43-CO cells.

The data above confirms that EHV-1 viruses lacking ORF43 gene can only replicate in cells expressing ORF 43 protein (as in ST-43-CO cells) and not in regular cells. The data also demonstrates ORF43 can be replaced with a different transgene that could be expressed in infected cells through an external promoter (such as mCMV) or as a part of EHV-1 genes (without an external promoter; with the endogenous promoter).

Figure 10:
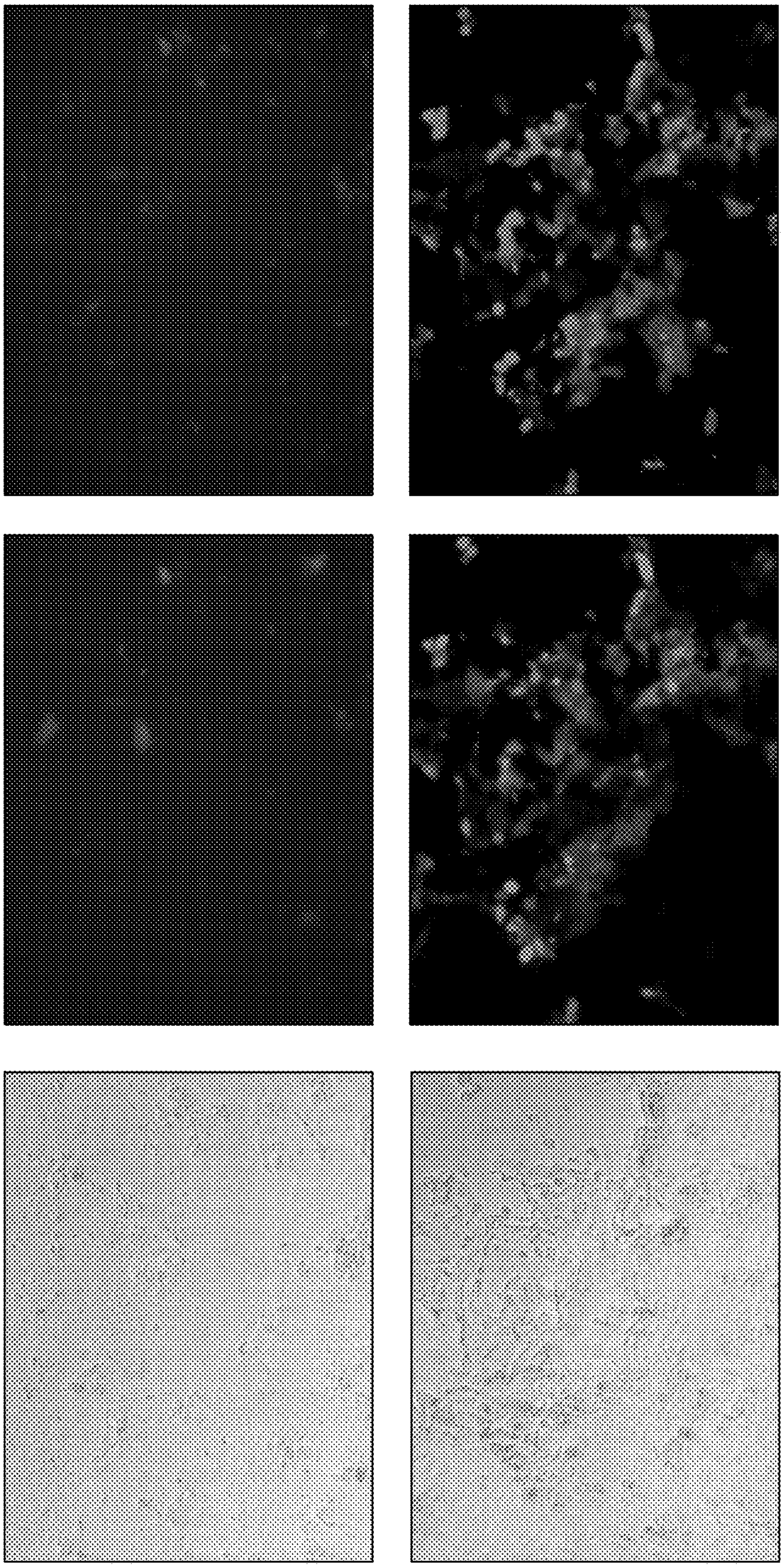
FIG. 10: ST (upper panel) and ST-54-CO and (lower panel) rEHV-1-54-mCMV-RFP virus. Infected cells express GFP (middle panel) and RFP (right panel), but virus spread and CPE observed only in rEHV-1-54-mCMV-RFP virus infected ST-54-CO cells.

Finally, regular ST cells and ST-54-CO cells were infected with rEHV-1-54-mCMV-RFP virus (FIG. 10). Although both cells were infected with rEHV-1-54-mCMV-RFP virus (as seen from GFP expression), CPE and virus production was observed only in ST-54-CO cells. Transgene (RFP) expression was observed in all of the infected cells but visible CPE or plaques were only observed in only ST-54-CO cells. This data above confirms that EHV-1 viruses lacking ORF54 gene can only replicate in cells expressing ORF 54 protein (as in ST-54-CO cells) and not in regular cells. The data also demonstrates ORF54 can be replaced with a different transgene that could be expressed in infected cells through an external promoter (such as mCMV).

We compared titers of various recombinant viruses produced on different cell lines (in triplicates). The data clearly demonstrates that viruses lacking ORF 43 or ORF 54 cannot replicate in regular cells (Table 1).

TABLE 1

| Sample No. | Virus | Produced in cells | Titer ($TCID_{50}$/ml) |
|---|---|---|---|
| 1 | rEHV-1-43-RFP | ST | 0 |
| 2 | rEHV-1-43-RFP | ST-43-CO | 6.49E+06 |
| 3 | rEHV-1-43-mCMV-RFP | ST | 0 |
| 4 | rEHV-1-43-mCMV-RFP | ST-43-CO | 5.99E+06 |
| 5 | rEHV-1-54-mCMV-RFP | ST | 0 |
| 6 | rEHV-1-54-mCMV-RFP | ST-54-CO | 1.24E+06 |

EXAMPLES 6

Replication Defective EHV-1 Virus with Transgenes at Other Insertion Sites

Synthetic DNA with flanks to knock out ORF 43 completely by two step red recombination are designed and transformed into GS1783 cells carrying EHV-1/HA BAC DNA (HA sequence, SEQ ID NO:14). After two step red recombination, ORF 43 is knocked out (confirmed by Sanger Sequencing, data not shown) to generate EHV-1-ΔORF43-HA. EHV-1-ΔORF43-HA BAC DNA (with a mCMV driven HA gene at ORF 1/3 site and lacking ORF 43) is transfected into ST-43-CO cells to rescue recombinant virus: rEHV-1-ΔORF43-HA.

Synthetic DNA with flanks to knock out ORF 54 completely by two step red recombination is designed and transformed into GS1783 cells carrying EHV-1/HA BAC DNA (HA sequence, SEQ ID NO:14). After two step red recombination, ORF 54 is knocked out (confirmed by Sanger Sequencing, data not shown) to generate EHV-1-ΔORF54-HA. EHV-1-ΔORF54-HA BAC DNA (with a mCMV driven HA gene at ORF 1/3 site and lacking ORF 54) is transfected into ST-43-CO cells to rescue recombinant virus: rEHV-1-ΔORF54-HA.

When regular ST and ST-43-CO cells are infected with rEHV-1-ΔORF43-HA at different MOI, CPE/virus production is observed only in infected ST-43-CO cells. HA expression in infected cells could be confirmed by IFA (Immunofluorescence Assay) using anti-HA antibody. When regular ST and ST-54-CO cells are infected with rEHV-1-ΔORF54-HA at different MOI, CPE/virus production is observed only in infected ST-54-CO cells. HA expression in infected cells could be confirmed by IFA (Immunofluorescence Assay) using anti-HA antibody.

EXAMPLE 7

Figure 11:
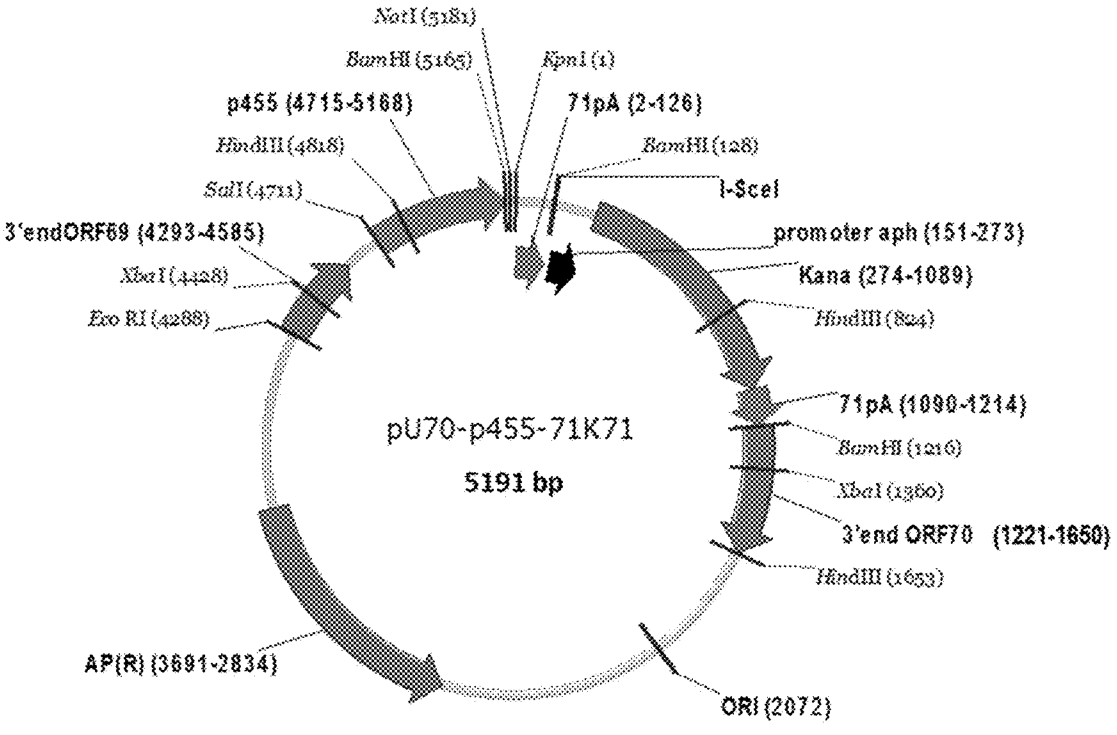
FIG. 11: Plasmid map of transfer vector pU70-p455-71K71
Figure 12:
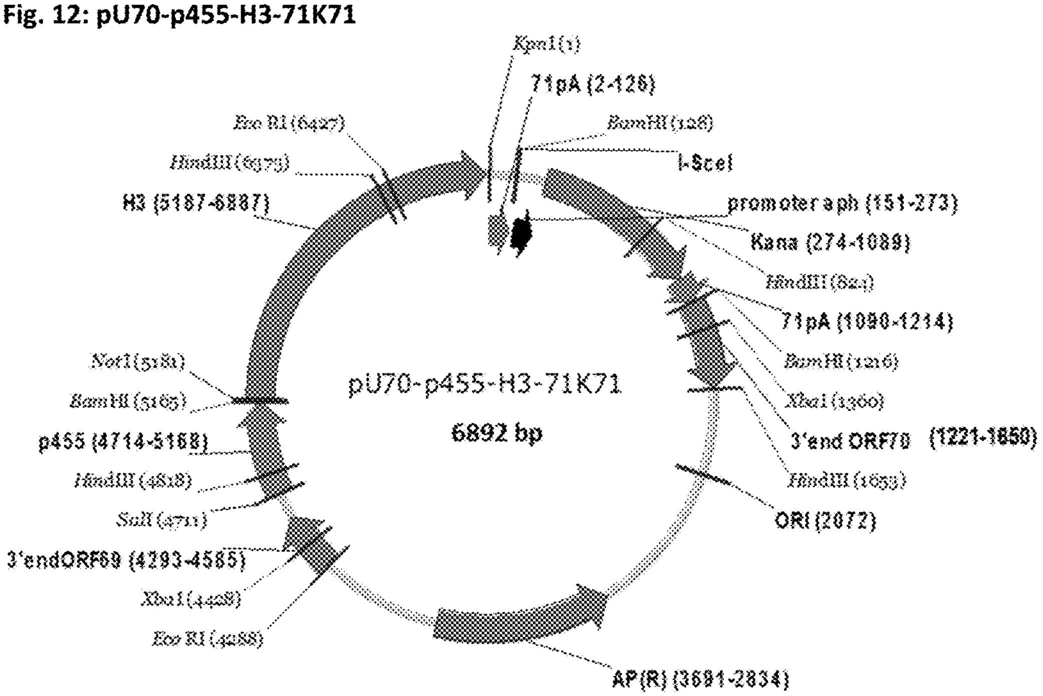
FIG. 12: Plasmid map of the transfer plasmid for insertion of expression cassette p455-H3-71 into ORF70 of EHV-1 RacH
Figure 13:
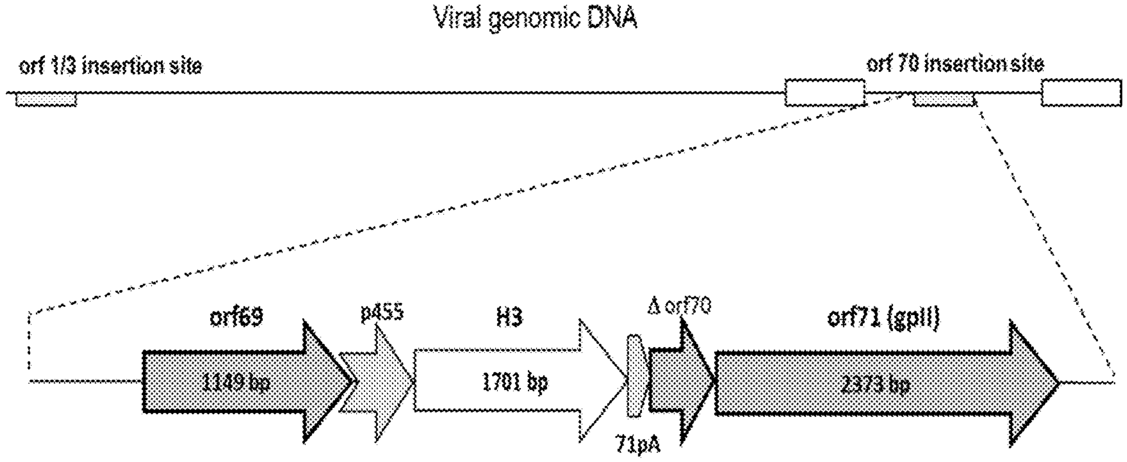
FIG. 13: Schematic illustration of the genome of rEHV-1 RacH-SE-70-p455-H3 with the orf70 insertion region enlarged. orf69: open reading frame number 69 upstream of the insertion site in orf70; p455: new promoter described herein, see e.g. example 1; H3: transgene Influenza Virus hemagglutinin; 71pA: new polyadenylation sequence; Δorf70: remainder of orf70 containing the promoter for orf71, which encodes the structural viral glycoprotein II (gpII).

Use of the ORF70 (US4) Insertion Site with p455 Promoter in Recombinant EHV-1 Vector Vaccines and Construction of a Recombinant Virus Influenza hemagglutinin subtype H3 (A/swine/Italy/7680/2001(H3N2), GenBank accession no.: ABS50302.2) was cloned into pU70-p455-71K71 (FIG. 11, SEQ ID NO. 15) to generate transfer plasmid pU70-p455-H3-71K71, placing H3 under control of the p455 promoter and the new 71pA polyadenylation signal and flanking the cassette with the recombination regions for insertion into ORF70 (FIG. 12, SEQ ID NO:16). RED recombination system (Tischer et al. 2006 Biotechnol. Tech. 40, 191-197) was used to clone the expression cassette p455-H3-71 at ORF70 of pRacH-SE to generate pRacH-SE70-p455-H3 (FIG. 13).

Figure 14:
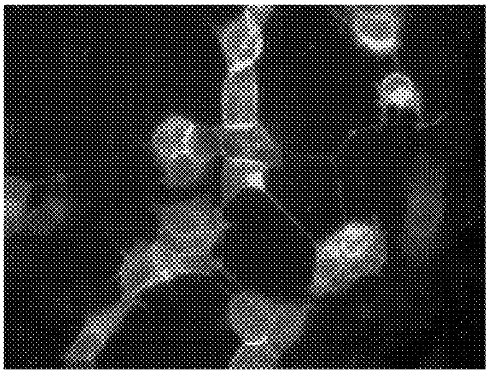
FIG. 14: Indirect immunofluorescence assay: Indirect immunofluorescence assay of VERO-cells infected with rEHV-1 RacH-SE-70-p455-H3 24 h p.i. cells were fixed with ethanol and air-dried. Using a commercial monoclonal antibody against H3 as primary antibody and a FITC-conjugated rabbit-anti mouse IgG as secondary antibody, H3 was shown in cells infected with the recombinant EHV-1 RacHSE-70-p455-H3 by fluorescence microscopy.

PK/WRL cells were transfected with pRacH-SE70-p455-H3, to rescue recombinant rEHV-1 RacH-SE70-p455-H3 virus. Insertion of the expression cassette was confirmed by sequencing of a high-fidelity PCR product of the insertion region. Expression of the transgene in infected cells was analyzed by indirect immunofluorescence assay (IFA, FIG. 14).

EXAMPLE 8

In Vivo Testing of a Monovalent EHV-1 Vectored Influenza a Virus Vaccine (H3 Vaccine) for Swine To test efficacy of rEHV-1 RacH-SE-70-p455-H3 as a potential vaccine, piglets without maternally derived immunity against Swine IAV (no maternal antibodies) were vaccinated twice with rEHV-1 RacH-SE-70-p455-H3 at a dose of 1×10^7 TCID50/mL intramuscularly at an age of two and five weeks respectively, or at an age of five weeks only (one-shot vaccination). Non-vaccinated group of piglets served as negative control and a group of animals that were vaccinated at two and five weeks of age with a commercially available inactivated Swine IAV vaccine according to the manufacturer's instructions (but for the time points of vaccination) served as positive control (euthanized). At an age of 8 weeks, all animals except the negative control group, were challenged by an intratracheally applied dosage of 1×10^7 TCID50/mL of an H3N2 Swine IAV challenge strain (European field virus isolate R452-14 whose H3 is being heterologous to the H3 vaccine antigen used in RacH-SE-70-p455-H3). Non-vaccinated and unchallenged animals served as negative control, while non-vaccinated but challenged animals served as challenge control. Body temperatures and blood samples were taken at selected time points. One day after challenge, half of the animals in each group were euthanized and the lungs were scored for lesions typical for Swine IAV infection, three lung samples per left and right lung were taken per animal, respectively, to determine infectious Swine IAV titers in lung homogenates, and bronchioalveolar lavage fluid (BALF) was sampled. The same procedure was performed with the remaining half on animals per group three days after challenge.

Figure 15:
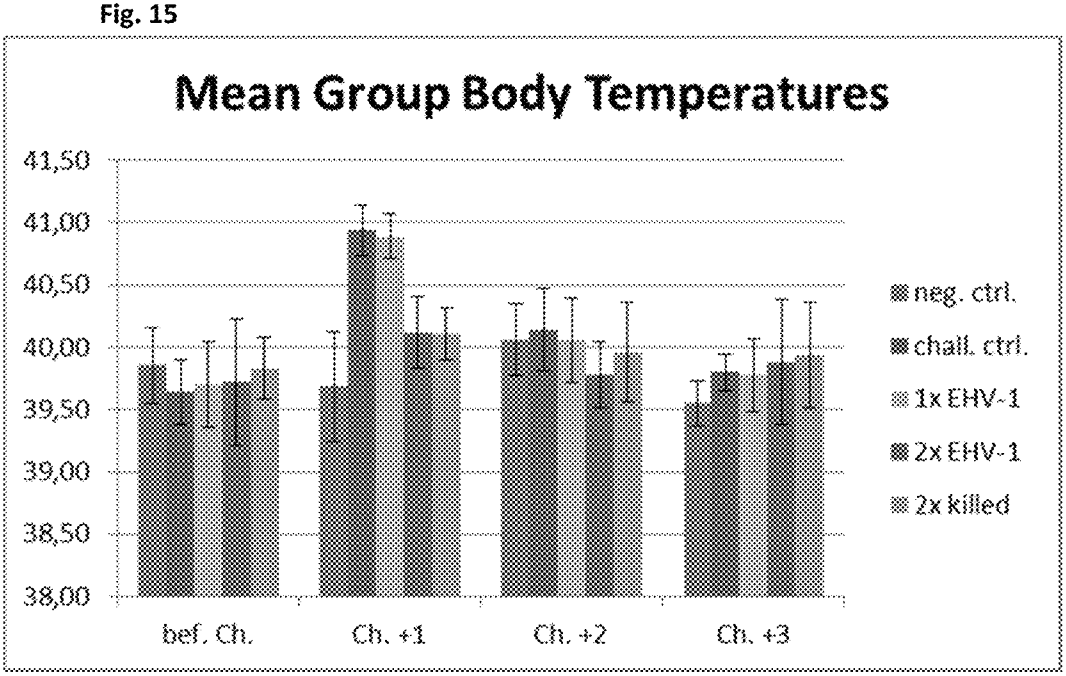
FIG. 15: Mean body temperatures of groups before and at 1,2, and 3 days after challenge. Error bars, standard deviations. From left to right per study day: negative control group (neg. ctrl.), challenge control group (chall. ctrl.), animals vaccinated once with RacH-SE-70-p455-H3 (1× EHV-1), vaccinated twice with with RacH-SE-70-p455-H3 (2× EHV-1), or twice with inactivated Swine IAV vaccine (2× killed).

When investigating the body temperature rise after Swine IAV challenge virus application, unlike piglets vaccinated twice with the rEHV-1 RacH-SE-70-p455-H3, non-vaccinated animals showed a body temperature increase of about 1° C. one day post-challenge (FIG. 15).

Figure 16:
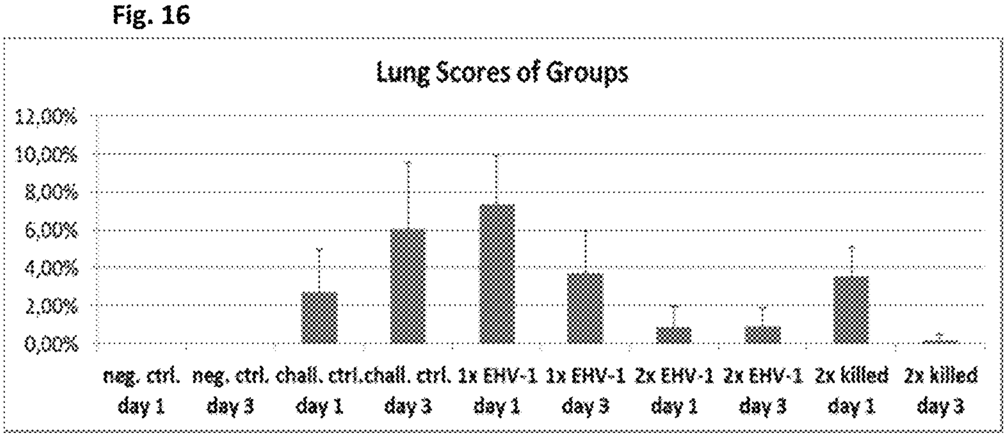
FIG. 16: Mean lung scores of groups one and three days after challenge. Error bars, standard deviations. Negative control group (neg. ctrl.), challenge control group (chall. ctrl.), animals vaccinated once with RacH-SE-70-p455-H3 (1× EHV-1), vaccinated twice with with RacH-SE-70-p455-H3 (2× EHV-1), or twice with inactivated Swine IAV vaccine (2× killed).

Lung scores were assessed in animals euthanized on 1 or 3 days post-challenge. Typical lung lesions associated with Swine IAV infection were absent in the negative control group piglets. But, lung lesions (in the mean range of 6 to 7%) were observed in the challenge control group. Finally, mean lung lesion scores were substantially lower (less than 4%) in piglets vaccinated twice with the rEHV1-RacH-SE-70-p455-H3 vaccine (FIG. 16).

Figure 17:
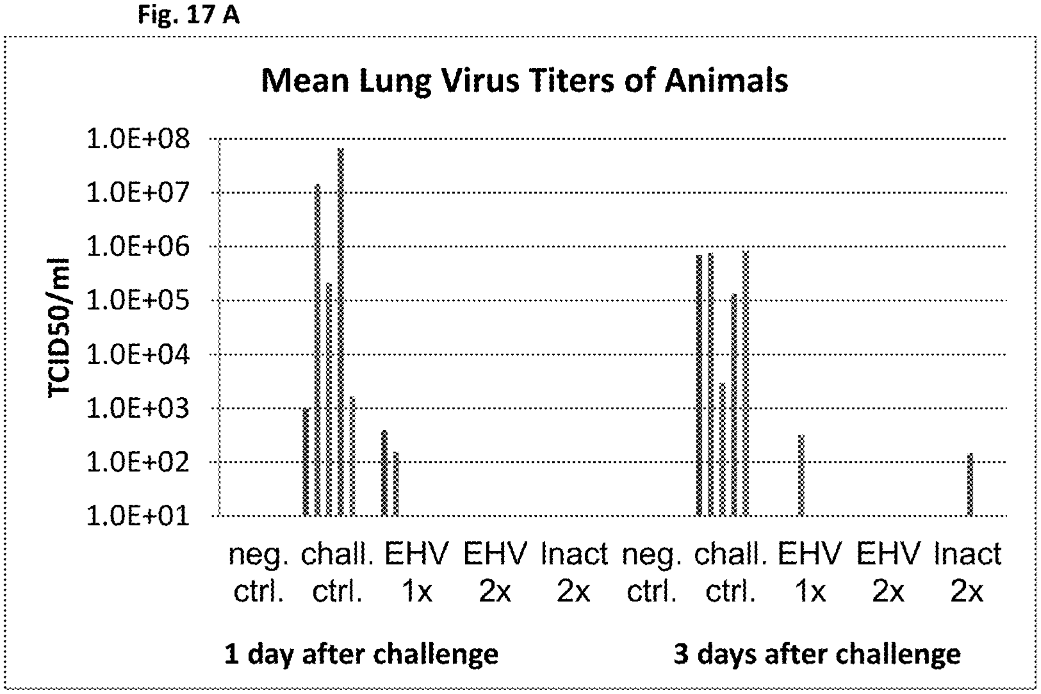
FIG. 17A: Virus Titers: Graph showing viral loads of lung samples of vaccinated or non-vaccinated pigs after challenge.
FIG. 17B Virus Titers: Graph showing viral loads of lung samples of vaccinated or non-vaccinated groups after challenge. Inact=commercially available inactivated vaccine. EHV=rEHV-1 RacH-SE-70-p455-H3
Figure 17B:
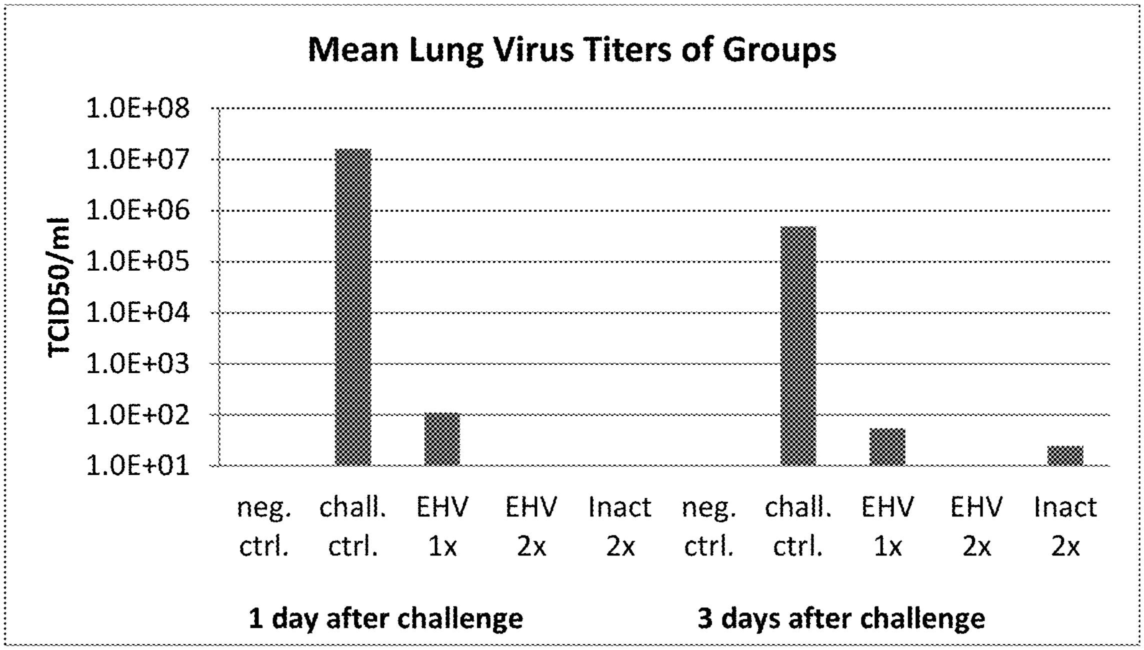

Mean Swine IAV lung titers were assessed in animals euthanized on 1 or 3 days post-challenge. While Swine IAV was absent in lung samples of the negative control group piglets, the challenge control group showed virus titers per g lung tissue in the range of more than 5 (day 3) to more than 7 logs (day 1). In stark contrast, the group mean values were strongly reduced to about two logs or less for the group vaccinated once with the rEHV1 RacH-SE-70-p455-H3 vaccine and reduced to undetectable levels for the group vaccinated twice with the rEHV-1 RacH-SE-70-p455-H3 vaccine (FIG. 17).

Figure 18:
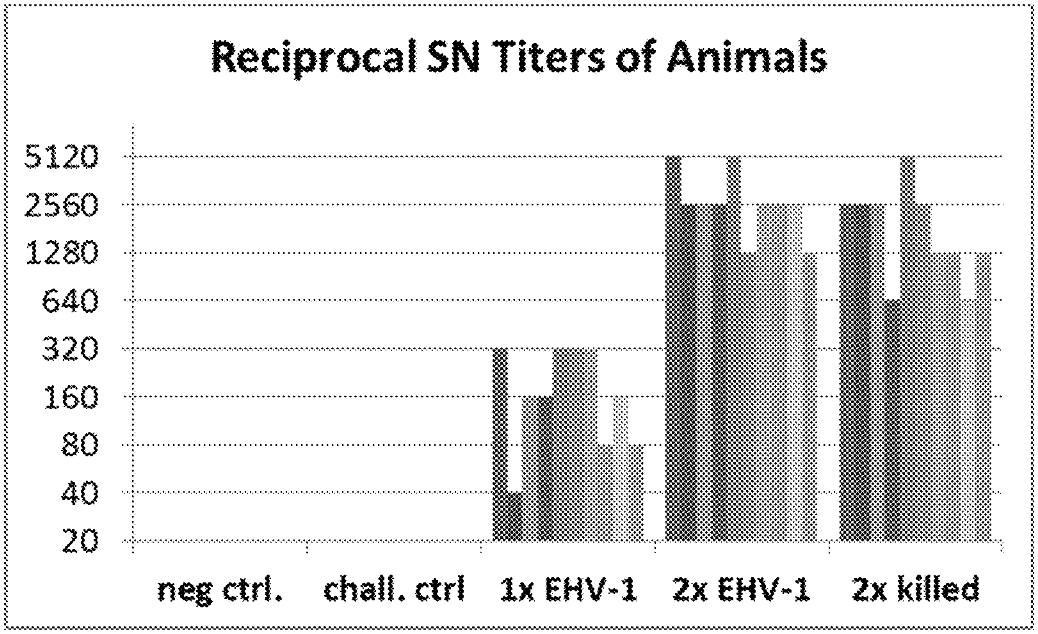
FIG. 18: Reciprocal serum neutralization (SN) titers of animal sera against Swine IAV H3 challenge strain R452-14 collected at day of challenge. 20, detection limit. Negative control group (neg. ctrl.), challenge control group (chall. ctrl.), animals vaccinated once with RacH-SE-70-p455-H3 (1× EHV-1), vaccinated twice with RacH-SE-70-p455-H3 (2× EHV-1), or twice with inactivated Swine IAV vaccine (2× killed).

When testing the induction of Swine IAV neutralizing antibodies after vaccination, sera from animals vaccinated once with the rEHV-1 RacH-SE-70-p455-H3 vaccine showed reciprocal neutralization titers in the range of about 160, three weeks after first vaccination and sera from animals vaccinated twice with the rEHV-1 RacH-SE-70-p455-H3 vaccine showed neutralizing titers of about 2560 three weeks after 2nd vaccination, while sera from the non-vaccinated groups had no detectable Swine IAV neutralizing antibody levels (FIG. 18).

Taken together, data from this example demonstrate that transgenes inserted at ORF70 in EHV-1 vector background can be expressed using an external promoter and the resulting recombinant EHV-1 vectors could be used in vivo as a potential vaccine candidate.

REFERENCES

The following references, to the extent that they provide exemplary procedural or other details supplementary to those set forth herein, are specifically incorporated herein by reference.

1. Bustin, S. 2000. Absolute quantification of mRNA using real-time reverse transcription polymerase chain reaction assays. Journal of Molecular Endocrinology 25(2): 169-193.
2. Goodwin, E. C. & Rottman, F. M. 1992. The 3' flanking sequence of the bovine growth hormone gene contains novel elements required for efficient and accurate polyadenylation. J. Biol. Chem. 267: 16330-16334
3. Hübert, P. H., Birkenmaier, S., Rziha, H. J. and Osterrieder, N. 1996, Alterations in the Equine Herpesvirus Type-1 (EHV-1) Strain RacH During Attenuation. Journal of Veterinary Medicine, Series B, 43: 1-14. doi: 10.1111/j.1439-0450.1996.tb00282.x
4. Luke, G A and Ryan, M D. 2013. The protein coexpression problem in biotechnology and biomedicine: virus 2A and 2A-like sequences provide a solution. Future Virology, Vol. 8, No. 10, Pages 983-996.
5. Ma, G., Azab, W., Osterrieder, N. 2013. Equine herpesviruses type 1 (EHV-1) and 4 (EHV-4)—masters of co-evolution and a constant threat to equids and beyond. Vet Microbiol. 167(1-2):123-34.

6. Nolan, T. Rebecca E Hands, R. E., and Bustin S. A. 2006. Quantification of mRNA using real-time RT-PCR Nature Protocols 1: 1559-1582
7. Osterrieder, N., Neubauer, A., Brandmüller, C., Kaaden, O. R., and O'Callaghan, D. J. 1996. The equine herpesvirus 1 IR6 protein influences virus growth at elevated temperature and is a major determinant of virulence. Virology 226:243-251.
8. Ptashne, M. 2014. *The Chemistry of Regulation of Genes and Other Things* The Journal of Biological Chemistry Vol. 289, (9) 5417-5435. Reed, L. J., and Muench, H. 1938. A simple method of estimating fifty percent endpoints. Am. J. Hyg. (27) 3; 493-497.
9. Reed L J and Muench H (1938). A simple method estimating fifty percent endpoints. The American Journal of Hygiene 27(3) 493-497
10. Rosas, C. T., Konig, P., Beer, M., Dubovi, E. J., Tischer, B. K., Osterrieder, N., 2007a. Evaluation of the vaccine potential of an equine herpesvirus type 1 vector expressing bovine viral diarrhea virus structural proteins. J. Gen. Virol. 88 (3), 748-757.
11. Rosas, C. T., B. K. Tischer, G. A. Perkins, B. Wagner, L. B. Goodman, N. Osterrieder. 2007b. Live-attenuated recombinant equine herpesvirus type 1 (EHV-1) induces a neutralizing antibody response against West Nile virus (WNV) Virus Research, 125, pp. 69-78.
12. Rosas, C. T., Van de Walle, G. R., Metzger, S. M., Loelzer, K., Dubovi, E. J., Kim, S. G., Parrish, C. R., Osterrieder, N., 2008. Evaluation of a vectored equine herpesvirus type 1 (EHV-1) vaccine expressing H3 haemagglutinin in the protection of dogs against canine influenza. Vaccine 26 (19), 2335-3234.
13. Said, A., Elke Lange, E., Beer, M. Damiani, A., Osterrieder, N. 2013. Recombinant equine herpesvirus 1 (EHV-1) vaccine protects pigs against challenge with influenza A(H1N1)pmd09 Virus Research 173: 371-376
14. Sambrook J and Russell D W (2001). Molecular Cloning, 3rd ed. Cold Spring harbor Laboratory Press, Cold Spring Harbor, N.Y; ISBN 978-087969-577-4
15. Shaner, N. C., Campbell, R. E., Steinbach, P. A., Giepmans, B. N., Palmer, A. E., Tsien, R, Y. 2004. Improved monomeric red, orange and yellow fluorescent proteins derived from Discosoma sp. red fluorescent protein. Nat Biotechnol. December; 22(12):1567-72. Epub 2004 Nov. 21.
16. Tischer, B. K., Kaufer, B. B., Sommer, M., Wussow, F., Arvin, A., and Osterrieder, N. A Self-Excisable Infectious Bacterial Artificial Chromosome Clone of Varicella-Zoster Virus Allows Analysis of the Essential Tegument Protein Encoded by *ORF*9. J. Virol.81 (23), 2007, 13200-13208.
17. Tischer, B. K, Smith, G. A., and Osterrieder, N. in: Jeff Braman (ed.), *In Vitro Mutagenesis Protocols: Third Edition*, Methods in Molecular Biology, vol. 634,DOI 10.1007/978-1-60761-652-8_30, © Springer Science+ Business Media, LLC 2010, Chapter 30: *En Passant* Mutagenesis: A Two Step Markerless Red Recombination System.
18. Trapp, S., von Einem, J., Hofmann, H., Kostler, J., Wild, J., Wagner, R., Beer, M., Osterrieder, N., 2005. Potential of equine herpesvirus 1 as a vector for immunization. J. Virol. 79, 5445-5454.
19. Wellington, J. E., Allen, G. P., Gooley, A. A., Love, D. N., Packer, N. H., Yan, J. X., Whalley, J. M. 1996. The highly O-glycosylated glycoprotein gp2 of equine herpesvirus 1 is encoded by gene 71. J Virol. 70(11):8195-8.

What is claimed is:

1. A replication deficient Equid Alphaherpesvirus (EHV) vector comprising an inactivation of UL18 and/or UL8, wherein the inactivation of UL18 and/or UL8 is a complete or partial deletion, a complete or partial truncation, a complete or partial inversion, or an insertion.

2. The replication deficient EHV vector of claim 1, wherein at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 925 nucleotides, at least 940 nucleotides are deleted, or inverted within the UL18.

3. The replication deficient EHV vector of claim 1, wherein at least 1 nucleotide, at least 2 nucleotides, at least 3 nucleotides, at least 4 nucleotides, at least 5 nucleotides, at least 10 nucleotides, at least 25 nucleotides, at least 50, nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900, nucleotides, at least 1000 nucleotides, at least 1250 nucleotides, at least 1500, nucleotides, at least 1750 nucleotides, at least 2000 nucleotides, at least 2225 nucleotides are deleted, or inverted within the UL8.

4. The replication deficient EHV vector of claim 1, wherein a DNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the DNA sequence as set forth in SEQ ID NO:1 is deleted or inverted within the UL18.

5. The replication deficient EHV vector of claim 1, wherein a DNA sequence having at least 70%, at least 75%, at least 80%, at least 85%, at least 90%, at least 91%, at least 92%, at least 93%, at least 94%, at least 95%, at least 96%, at least 97%, at least 98% or at least 99% identity to the DNA sequence as set forth in SEQ ID NO:2 is deleted, or inverted within the UL8.

6. The replication deficient EHV vector of claim 1, wherein the EHV vector comprises an expression cassette comprising:

(i) at least one exogenous nucleotide sequence of interest, preferably a gene of interest, more preferably an antigen encoding sequence, wherein said nucleotide sequence of interest, preferably a gene of interest, more preferably an antigen encoding sequence is optionally operably linked to a promoter sequence, and (ii) at least one upstream UL18 flanking region selected from the group consisting of: SEQ ID NO:5 and a 70%, 80%, 85%, 90%, 91%, 92%, 93%, 94%, 95%, 96%, 97%, 98%, 99% homologous and/or identical sequence thereof, SEQ ID NO:9 and a 70%, 80%, 85%, 90%, 91%, 92%, 93%, 94%, 95%, 96%, 97%, 98%, 99% homologous and/or identical sequence thereof, (iii) at least one downstream UL18 flanking region selected from the group consisting of: SEQ ID NO:6 and a 70%, 80%, 85%, 90%, 91%, 92%, 93%, 94%, 95%, 96%, 97%, 98%, 99% homologous and/or identical sequence thereof, SEQ ID NO:10 and a 70%, 80%, 85%, 90%, 91%, 92%, 93%, 94%, 95%, 96%, 97%, 98%, 99% homologous and/or identical sequence thereof.

7. The replication deficient EHV vector of claim 1, wherein the EHV vector comprises an expression cassette comprising:

(i) at least one exogenous nucleotide sequence of interest, preferably a gene of interest, more preferably an antigen encoding sequence, wherein said nucleotide sequence of interest, preferably a gene of interest, more preferably an antigen encoding sequence is optionally operably linked to a promoter sequence, and (ii) at least one upstream UL8 flanking region selected from the group consisting of: SEQ ID NO:11 and a 70%, 80%, 85%, 90%, 91%, 92%, 93%, 94%, 95%, 96%, 97%, 98%, 99% homologous and/or identical sequence thereof, and (iii) at least one downstream UL8 flanking region selected from the group consisting of: SEQ ID NO:12 and a 70%, 80%, 85%, 90%, 91%, 92%, 93%, 94%, 95%, 96%, 97%, 98%, 99% homologous and/or identical sequence thereof.

8. The replication deficient EHV vector of claim 6, wherein the insertion of the expression cassette into UL18 is characterized by a deletion of an approximately 945 bp portion within UL18 for RacH (SEQ ID NO:1) or a 70%, 80%, 85%, 90%, 91%, 92%, 93%, 94%, 95%, 96%, 97%, 98%, 99% homologous and/or identical sequence thereof.

9. The replication deficient EHV vector of claim 7, wherein the insertion of the expression cassette into UL8 is characterized by a deletion of an approximately 2256 bp portion within UL8 for RacH (SEQ ID NO:2) or a 70%, 80%, 85%, 90%, 91%, 92%, 93%, 94%, 95%, 96%, 97%, 98%, 99% homologous and/or identical sequence thereof.

10. The replication deficient EHV vector of claim 1, wherein the EHV vector comprises (i) at least one upstream UL18 flanking region selected from the group consisting of: SEQ ID NO:5 and SEQ ID NO:9, and (ii) at least one downstream UL18 flanking region selected from the group consisting of: SEQ ID NO:6 and SEQ ID NO:10.

11. The replication deficient EHV vector of claim 1, wherein the EHV vector comprises (i) at least one upstream UL8 flanking region selected from the group consisting of: SEQ ID NO:11 and (ii) at least one downstream UL8 flanking region selected from the group consisting of: SEQ ID NO:12.

12. The replication deficient EHV vector of claim 1, wherein replication deficient means that the replication rate is reduced at least by 90%.

13. The replication deficient EHV vector of claim 1, wherein the replication deficient EHV vector is still infective.

14. The replication deficient EHV vector of claim 1, wherein the EHV vector comprises at least one nucleotide sequence of interest, preferably a gene of interest, more preferably an antigen encoding sequence, inserted into an insertion site, preferably UL56 and/or US4.

15. The replication deficient EHV vector of claim 6, wherein said antigen encoding sequence relates to a pathogen infecting a food producing animal such as swine, cattle or poultry or companion animals such as cat, Equine or dog, preferably, the antigen encoding sequence is from a pathogen selected, but not limited to, from the list: Schmallenberg virus, Influenza A Virus, Porcine Respiratory and Reproductive Syndrome Virus, Porcine Circovirus, Classical Swine Fever Virus, African Swine Fever Virus, Hepatitis E Virus, Bovine Viral Diarrhea Virus, Rabies Virus, Feline Morbillivirus, *Clostridium tetani, Mycobacterium tuberculosis, Actinobacillus Pleuropneumoniae.*

16. The replication deficient EHV vector of claim 1, wherein the EHV vector is selected from the group consisting of EHV-1, EHV-3, EHV-4, EHV-8 and EHV-9.

17. A cell line expressing UL8 and/or UL18 of EHV or functional parts thereof for culturing the replication deficient EHV vector of claim 1.

18. An immunogenic composition comprising one or more EHV vectors according to claim 1.

19. A method for immunizing a subject comprising administering to such subject an immunogenic composition of claim 18.

* * * * *